(12) United States Patent
Cheng et al.

(10) Patent No.: US 7,186,245 B1
(45) Date of Patent: Mar. 6, 2007

(54) PERSONAL URINE MANAGEMENT SYSTEM FOR HUMAN MALES

(76) Inventors: Gordon C. Cheng, 222 Stoney Gate, Carlisle, MA (US) 01741; James R. Valentine, 166 Woburn St., Reading, MA (US) 01867; Daniel M. Beane, 52 Burr Rd., Hingham, MA (US) 02043; Richard M. Beane, 52 Burr Rd., Hingham, MA (US) 02043

( * ) Notice: Subject to any disclaimer, the term of this patent is extended or adjusted under 35 U.S.C. 154(b) by 889 days.

(21) Appl. No.: 09/606,721

(22) Filed: Jun. 29, 2000

Related U.S. Application Data

(60) Provisional application No. 60/141,439, filed on Jun. 29, 1999.

(51) Int. Cl.
*A61F 5/44* (2006.01)
(52) U.S. Cl. ...................... 604/350; 604/349
(58) Field of Classification Search ......... 604/349–352
See application file for complete search history.

(56) References Cited

U.S. PATENT DOCUMENTS

| | | | |
|---|---|---|---|
| 3,788,324 A | 1/1974 | Lim | 604/352 |
| 3,800,795 A | 4/1974 | Walker | 604/323 |
| 3,835,857 A * | 9/1974 | Rogers, III et al. | 604/349 |
| 3,863,638 A * | 2/1975 | Rogers, III et al. | 604/349 |
| 3,957,054 A | 5/1976 | McFarlane | 604/541 |

(Continued)

FOREIGN PATENT DOCUMENTS

WO   WO 91/04714   4/1991

(Continued)

*Primary Examiner*—Tatyana Zaukaeva
*Assistant Examiner*—C. Lynne Anderson
(74) *Attorney, Agent, or Firm*—George W. Dishong

(57) ABSTRACT

Novel component devices for urine management systems including a novel collection device, a novel conveyance tube, and a novel storage container. The collection device, a novel male catheter, comprises a waterproof, thin-walled conduction tube surrounding the penis, having wettable internal walls and containing a spacing wick. At one end, the conduction tube is connected to, or surrounded by, an elastic compression tube that provides a uniform compressive force around the girth of the penis for attachment and liquid seal to said penis, and at the other end is attached to a fitting that connects to the conveyance tube. The elastic compression tube is radially expanded prior to donning and, when in place over the penis, is allowed to elastically retract, providing radial compression for comfortable, and leak-free fit and use. The conveyance tube, which carries urine from collector to storage container, contains a spacer throughout its length to prevent the tube lumen from being completely closed and sealed off by kinks or twists in the tube. Said tube may be a thin-wall flat tube that can conform to the body shape of the wearer, can expand in cross-section as flow rate increases, and can shrink and flatten as flow rate drops off. Urine is retained as immobilized material in a storage container that can be either replaced and disposed of or emptied and reused with cleaning as needed. The storage container's internal structure also provides a means for unique fluid transfer and retention capabilities. A system comprised entirely of said novel devices, serially and contiguously connected, forms a continuous liquid pathway that enables removal of residual pools of urine, as well as transport and storage of urine at locations that are gravitationally higher than the source.

1 Claim, 20 Drawing Sheets

U.S. PATENT DOCUMENTS

| | | | |
|---|---|---|---|
| 3,967,645 A | 7/1976 | Gregory | 137/846 |
| 4,246,901 A | 1/1981 | Frosch et al. | 604/329 |
| 4,257,422 A | 3/1981 | Duncan | 604/266 |
| 4,317,452 A | 3/1982 | Russo et al. | 128/350 |
| 4,360,932 A | 11/1982 | Yoshida | 4/144.2 |
| 4,475,909 A * | 10/1984 | Eisenberg | 604/349 |
| 4,484,918 A | 11/1984 | Omley | 604/349 |
| 4,553,966 A | 11/1985 | Korteweg | 604/317 |
| 4,559,049 A | 12/1985 | Haan | 604/350 |
| 4,579,555 A | 4/1986 | Russo | 604/541 |
| 4,640,688 A * | 2/1987 | Hauser | 604/352 |
| 4,759,753 A * | 7/1988 | Schneider et al. | 604/352 |
| 4,769,099 A | 9/1988 | Therriault et al. | 156/230 |
| 4,813,943 A | 3/1989 | Smith | |
| 4,840,625 A * | 6/1989 | Bell | 604/352 |
| 4,846,816 A | 7/1989 | Manfredi | 604/323 |
| 5,002,541 A * | 3/1991 | Conkling et al. | 604/319 |
| 5,007,116 A | 4/1991 | Yamamoto | 4/144.2 |
| 5,053,027 A | 10/1991 | Manfredi | |
| 5,171,307 A | 12/1992 | Sanning | 604/327 |
| 5,318,550 A * | 6/1994 | Cermak et al. | 604/349 |
| 5,336,211 A * | 8/1994 | Metz | 604/352 |
| 5,354,132 A | 10/1994 | Young et al. | 383/49 |
| 5,380,312 A * | 1/1995 | Goulter | 604/352 |
| 5,496,300 A | 3/1996 | Hirsch et al. | 604/321 |
| 5,531,724 A | 7/1996 | Young et al. | 604/327 |
| 5,632,736 A | 5/1997 | Block | |
| 5,645,541 A * | 7/1997 | Bouser | 604/353 |
| 5,662,631 A * | 9/1997 | Marx | 604/352 |
| 5,676,688 A * | 10/1997 | Jaker et al. | 606/195 |
| 5,713,880 A * | 2/1998 | Anderson | 604/349 |
| 5,776,115 A | 7/1998 | Antoshkiw et al. | 604/327 |
| 5,797,890 A * | 8/1998 | Goulter et al. | 604/351 |
| 5,827,249 A * | 10/1998 | Jensen | 604/349 |
| 5,865,821 A | 2/1999 | Lowey | |
| 5,897,540 A * | 4/1999 | Grundke et al. | 604/352 |
| 5,926,858 A * | 7/1999 | Heller | 4/144.1 |
| 5,957,904 A | 9/1999 | Holland | 604/331 |
| 6,007,526 A * | 12/1999 | Passalaqua et al. | 604/349 |
| 6,068,618 A | 5/2000 | Anderson | 604/349 |
| 6,113,582 A * | 9/2000 | Dwork | 604/349 |
| 6,117,120 A * | 9/2000 | Heininger | 604/349 |
| 6,183,454 B1 | 2/2001 | Levine et al. | |
| 6,186,990 B1 | 2/2001 | Chen et al. | 604/349 |

FOREIGN PATENT DOCUMENTS

| | | |
|---|---|---|
| WO | WO 9739705 A1 | 10/1997 |

\* cited by examiner

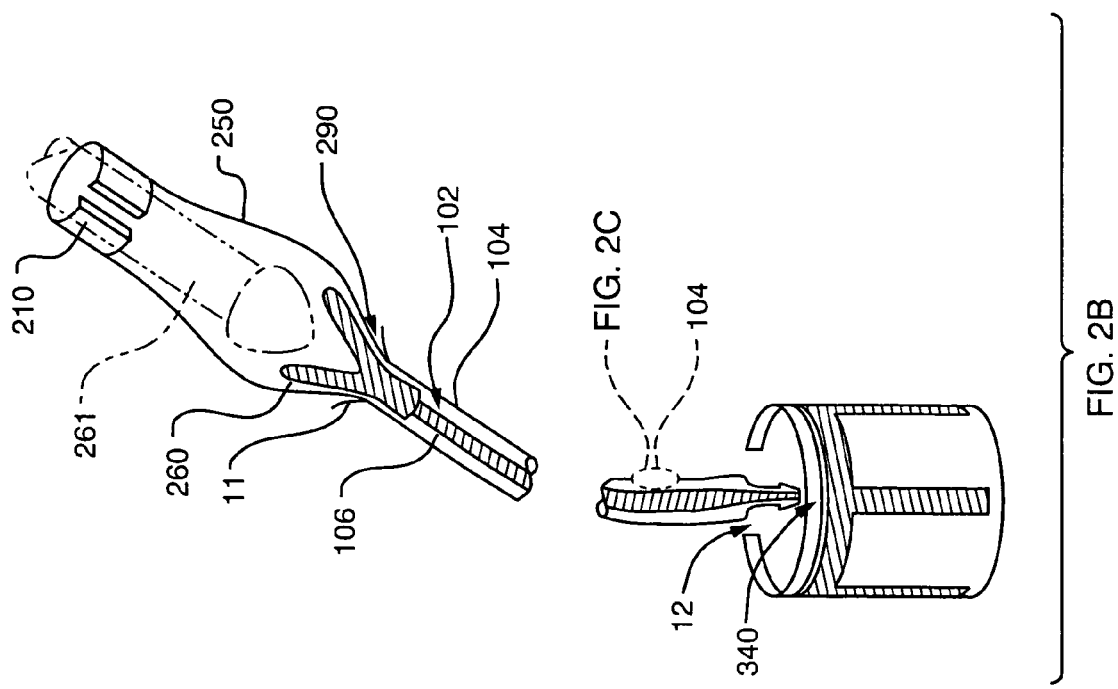
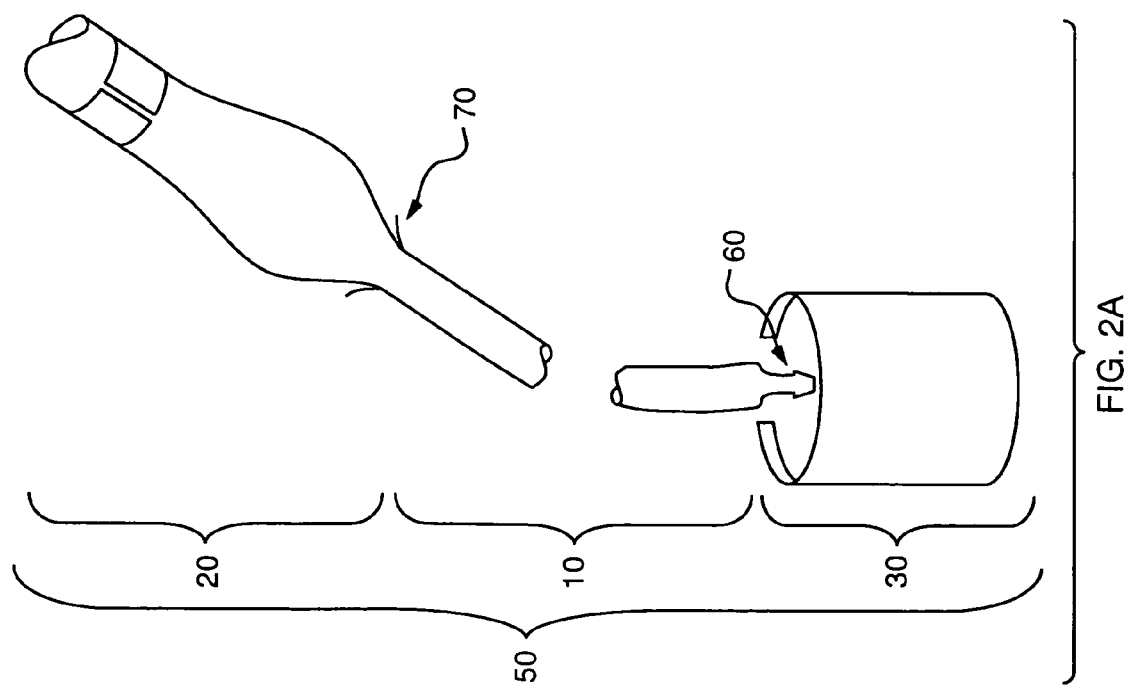

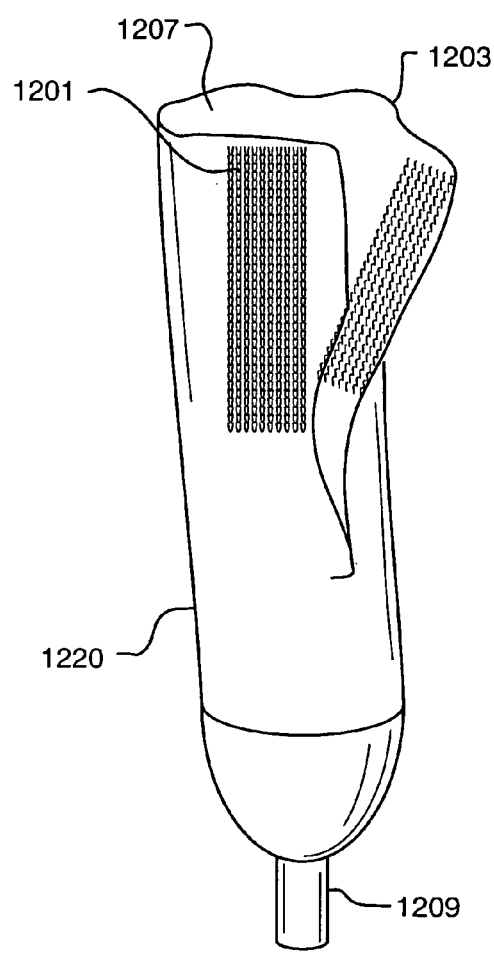
FIG. 12A
FIG. 12B

PERSONAL URINE MANAGEMENT SYSTEM FOR HUMAN MALES

CROSS-REFERENCE TO RELATED APPLICATIONS

This application relies on the priority date of U.S. Provisional Patent Application filed on Jun. 29, 1999, entitled URINE MANAGEMENT SYSTEM, Application No. 60/141,439.

STATEMENT REGARDING FEDERALLY SPONSORED RESEARCH OR DEVELOPMENT

Not Applicable.

BACKGROUND OF THE INVENTION

1. Field of the Invention

The present invention relates to the field of collecting urine and conveying it from point of collection to storage. More particularly, this invention relates to an apparatus for human urine collection, storage, and disposal, that addresses the problems associated with such devices of current art. Most particularly, this invention relates to an apparatus that addresses the problem of human incontinence.

2. Description of Related Art

Apart from finding some form of medical or surgical cure, ambulatory adult human males who are urine incontinent generally are faced with two alternatives to manage their condition: using a system of devices worn on the body to collect and store the urine for periodic disposal, or wearing an absorbent pad or undergarment which they must periodically change. The "system of devices" generally consists of a device for urine collection, a device for conveying the collected urine to storage, and a device for storing the conveyed urine with periodic draining into a toilet. Current urine collection and storage technology for urine incontinent males relies almost exclusively on the use of external or sheath catheters (also called condom catheters) that surround the penis with a waterproof tube to collect the urine and that are attached to a storage bag by means of a length of standard-wall rubber or vinyl polymer tubing. Said bag is often worn attached to the user's leg.

Unfortunately, these current "devices" are severely lacking in several key areas. For example, many of the current collection devices are difficult to apply and remove, and can lead to injurious and painful penile skin conditions. The conveyance tubing generally used is stiff, bulky, and often visible under clothing. Lastly, current leg-mounted storage bags are bulky, uncomfortable, and a potential source of leakage and consequent major embarrassment.

Suitable solutions for these problems are not obvious. For example, the relative stiffness of the conveyance tubing renders it resistant to kinking and bending movements that could crimp the tube lumen shut. Unfortunately, the same stiffness property also does not lend itself well to comfortable, discreet use because it does not easily conform to tight bends such as are needed in fitting closely to the human body.

Simply substituting a thinner-walled tube for the thicker-walled one, while providing more flexibility, conformation and movement, will likely result in significantly poorer performance with respect to collapsing and sealing off of periodic, low volume flows such as incontinence leakage. In addition, use of a simple open-lumen tube may result in drainage problems. While any open tube may be used as a conduit channel for gravity-driven, descendant fluid flow, that same tube will present difficulties in fluid transport situations where the drainage path involves some ascendant flow to a higher point prior to reverting to descendant flow to a point below the source (e.g., for a seated user, a flow path proceeding from the urethral opening up the thigh to the knee prior to flowing down to a storage vessel attached to the lower leg). In order to make the system work as described, the urine must accumulate in sufficient quantity to fill the tube to the highest point before it can overflow down to the storage bag. Such a situation is extremely detrimental to the health of the user's urethral tract as well as to the health of the penile skin, and is very likely to lead to significant leakage around the collection device and fittings. To avoid these problems, users must rise periodically to facilitate gravity flow.

Collector Background

Current art sheath catheters are very thin-walled tubes of latex or silicone rubber (often 0.002–0.004 inch) that are deliberately sized to be larger in diameter than the penis, have an opening in the proximal end for insertion of the penis, and have an opening in the distal end to conduct the urine away. They are usually packaged in an axially rolled condition. For use, they are unrolled directly onto the shaft of a penis that is in a flaccid condition. Virtually all current sheath catheters are attached to the penis using an adhesive that is either on a strip of double-sided adhesive tape pre-applied to the penis, or is a coating applied to a portion of the catheter's interior surface during manufacture. The adhesive is employed for two purposes; to hold the catheter in place on the penis; and to help to effect a seal between the catheter and the skin. Unfortunately, the adhesive makes the application and removal of the catheter from a flaccid organ difficult and irritating to the user. In order to reduce pain associated with removing the sheath catheter from adhered skin, users are often instructed to remove hairs in the bodily area surrounding the penis.

Although the over-sized diameter is necessary for current art sheath catheters to facilitate the application method of unrolling onto a flaccid penis, it is not at all conducive to achieving a good urine seal, because folds in both the excess condom material and the loose skin of the penis can create potential urine leakage pathways along the bends and seams of folded material. Current art sheath catheters use either the attachment adhesive coating described above or a mechanical ring as a means to attempt to compress the folds and to seal off these seams to prevent urine leakage at the proximal end of the catheter.

Examples of the current art include the following. A typical sheath catheter is in U.S. Pat. No. 4,769,099 which describes a tubular elastic sheath catheter having a band of adhesive on the internal wall, and means for applying the adhesive layer to the internal wall. A non-adhesive catheter is in U.S. Pat. No. 4,846,816 which describes a complete urine collection and containment system that includes a tubular elastic sheath which utilizes a compressive elastic rubber ring over the sheath near the proximal opening to provide an o-ring mechanical and liquid seal around the penis.

Current art condom catheters can suffer from incomplete drainage of urine (also known as "pooling"). The resulting prolonged exposure of the penile skin to liquid urine, urine decomposition products (e.g. ammonia, etc), and moisture frequently leads to skin irritation and breakdown. Flow blockage due to crimping of the catheter or catheter tube is one of the main causes of pooling. The catheter is 1-inch or larger diameter, very thin-walled tubing while the conveyance tube used to transport the urine from the catheter to the storage container is almost always of 0.25–0.31-inch inside diameter, thick-walled (0.06 inch) latex or vinyl polymer tubing. In order to connect the two very different forms of tubing it is therefore necessary to make a gradual reduction in diameter and thickening of the walls resulting in a "funnel-like" shape in the transition zone that will connect to the conveyance tube. In typical current art, the distal discharge end of the sheath catheter is thick-walled (often 0.06 inch), relatively stiff, and somewhat resistant to movements that could otherwise constrict and crimp the tube lumen and, thereby, impede the urine flow. This transition zone has been addressed in various modifications made to the catheter. For example, U.S. Pat. No. 3,788,324 describes a catheter having a thicker material used at the distal end, and U.S. Pat. No. 4,846,816 describes multiple convolutions in the tip region of the catheter that allow limited bending at each successive convolution thus affording adequate change in direction. Unfortunately, thick-walled tubing does not lend itself well to comfortable and discreet use.

Another cause for pooling in existent collection devices is their complete dependence on descending (gravity-driven) flow to convey the urine. When the wearer is in a seated position, urine must move along an ascending flow path (i.e., counter to gravity) from the collection point (i.e., the urethral opening) up the leg to the knee as a high point before flowing down to the storage bag which is generally attached to the user's calf. The conveyance tube must remain filled with urine to achieve overflow. Thus, with existent external catheters, such accumulation of urine in the existent art catheter and conveyance tube can be a major problem for a seated user because urine will completely fill the catheter-collector and conveyance tube, with serious risk of leakage and consequent embarrassment in addition to the health effects on skin. With current art devices, this problem can only be alleviated by rising from the seated position periodically to facilitate gravity drainage of the urine being held up in the collection device.

Conveyance Tube Background

Current devices used by ambulatory, incontinent males for collection and storage of their urine almost exclusively employ a length of a generic "laboratory-type" rubber or vinyl polymer tubing to convey the urine from the collection device (usually an external or internal catheter) to the storage bag (usually worn on the leg). The tubing used generally has a ¼- or ⁵⁄₁₆-inch internal diameter and a ¹⁄₁₆-inch wall thickness, Tubing of this type depends upon wall rigidity in the radial direction combined with limited longitudinal elasticity (i.e., relative "stiffness") to prevent the kinking, crimping or other lumen-collapsing actions that can occur during bending and that can seal off the fluid path, effectively stopping urine flow.

Unfortunately, because of the same stiffness property, the tubing does not easily conform to tight bends such as are needed in fitting closely to the human body. Because the tubing does not fit closely to the body, in urine conveyance use, such tubing can be visible beneath clothing, and thus does not lend itself well to discreet use. Some prior art applications have incorporated axial pleats or convolutions into this conventional-wall tubing to aid bending movements in the regions of connection to collectors or storage bags. For example, U.S. Pat. No. 4,846,816 describes a complete urine collection system that includes urine conduit tubing that is circumferentially pleated to enhance flexibility.

Simply substituting a thinner-walled tube for the "standard"-wall version, while possibly providing more flexibility, conformability, and movement, would likely result in significantly poorer performance because such a tube would be much more susceptible to crimping and blockage of periodic, low volume flows such as incontinence leakage.

The simple, open-lumen tube in current urinary incontinence use also has other limitations that can cause problems in liquid drainage under certain conditions. One limitation lies in the open tube's complete reliance on gravitational force to promote drainage. Any open tube may be used as a conduit channel for gravity-driven, descendant fluid flow from a collector source at one level to a receiver at a lower level. However, that same tube will present difficulties in fluid transport situations when the drainage path involves some ascendant flow to a higher point before reverting to descendant flow to a receiving point below the source. For example, for an incontinent user in the seated position, such a flow path would run from the urethral opening up the thigh to the knee (a location that is higher than the urethral opening) prior to flowing down to a storage vessel attached to the lower leg. In order to make the collector-to-storage "system" work as described, the urine must accumulate in sufficient quantity to fill the tube to the highest point before it can overflow down to the storage bag. Such a situation is very likely to lead to significant leakage around the collection device and tube connections. Moreover, such constant exposure to liquid urine is extremely detrimental to the health of the user's urethral tract as well as to the health of the urogenital skin in contact with the urine. To avoid these problems, seated users must rise periodically to facilitate gravity-dependant flow.

A second limitation lies in the potential for gas-bubble blockage. Drainage of liquid such as urine through a single tube lumen into a sealed, non-expandable receptor usually is expected to result in a simultaneous countercurrent flow of displaced air (atmosphere within the tube and connected storage bag) upward within the same tube lumen. The relatively narrow bore size, stiff wall structures, and wetting properties of the tube wall materials often cause conventional elastomeric urine conveyance tubes to be subject to the formation of liquid slugs where portions of the tube lumen become completely filled with urine. These slugs of urine prevent displaced air from rising in the lumen, thus creating a backpressure in the tube and storage container that slows flow into the bag. At the same time, gravitational force acting on the mass of the urine in the one or more slugs in the partially-filled column causes those slugs to be pulled further down the tube, thus creating a slight vacuum in the upper part of the tubing and in the connected collector. The slight vacuum can then result in in-leakage of air through imperfect seals in the collector with consequent formation of air bubbles and still more liquid plugs in the line. To counter this problem, means for venting the drainage tubing have been described, for example, U.S. Pat. No. 3,800,795.

Other means of avoiding crimping or kinking of similar tubing products include changing the tubing wall configuration. U.S. Pat. Nos. 4,579,555 and 5,776,115 disclose catheter drainage tubes having protuberances molded into the inner wall to prevent collapse of the tube lumen when the tube is crimped or kinked. Gravity is relied entirely upon for in-situ drainage. Incorporation of a protruding geometry into the inner wall of a tube requires relatively thick walls in order for the molded or extruded wall to maintain shape, and also generally implies that the resultant tube is similar to conventional tubes in terms of rigidity, weight and degree of discomfort in use.

In urinary drainage applications, connections to elastomeric conveyance tubing are generally accomplished utilizing the radial elasticity and the frictional properties of the tubing wall material. The end of the conveyance tube is pushed onto and over the opening of a rigid tube (often called the "tube fitting" or "connector") which is either a physical part of or connected to the urine collector or storage container. This fitting frequently has raised ridges (appearing on the fitting as a series of "rings" around the rigid tube circumference) and may also have an increasing outside diameter moving away from the opening. Both the ridges and the increasing diameter are intended to improve the frictional grip holding the conveyance tubing onto the fitting. Because of its frictional characteristics, the elastomer material can cause physical discomfort to the wearer during prolonged rubbing contact with the skin.

As noted above, current urine conveyance devices and prior art with few exceptions depend solely upon gravity-induced flow of urine for transfer. U.S. Pat. No. 4,246,901 describes a urine collection device for females that includes a conveyance tube that may contain some amount of wicking material to conduct the urine away from the collection area. The conveyance tube is of sufficient rigidity to resist crimping or kinking. No mention is made or implied regarding use of the wicking to enable ascendant (counter gravity) pumping of urine or siphoning urine over a hump.

Devices for removal of body and irrigation fluids during and after surgical procedures have made some use of wicking to induce fluid flow. For example, U.S. Pat. No. 4,553,966 discloses fluid irrigation drainage using wicking material. In this invention which focuses on aiding surgery on the brain and eye, the wick is placed at the site to be drained in situ, and it draws the fluid into a collection sack that, in turn, is connected via tubing to a disposal bag. U.S. Pat. No. 5,171,307 discloses an eye irrigation system, one component of that is a capillary tube for withdrawing waste solution during active irrigation of the eye. Both patents are focused on the application of capillary-aided and siphon-based fluid movement to effect careful in-situ drainage of delicate regions during surgical procedures, and both reflect the efficacy of the technology when the wicks and tubes have been carefully set in place by skilled practitioners as part of the surgical procedure. However, such processes have not been described for hygiene-related devices intended for use by the patient.

The patents noted herein provide considerable information regarding the developments that have taken place in this field of technology. However, improved means for conveying urine are needed, in particular because none of the prior art meets the objects of providing the following for ambulatory incontinent individuals.

Urine conveyance devices that can be worn unnoticed, thus preserving privacy.

Urine conveyance devices that incorporate separate components within their lumen that will ensure that the lumen cannot be completely sealed by a crimping or kinking action on the conveyance tube.

Urine conveyance devices that will enable ascendant flow of urine thus enabling conveyance of urine to take place while the user is in a seated position.

Urine conveyance devices that will transfer urine by means of a wicking and surface wetting action, thus enabling removal of pools and drops of liquid urine from regions within urine collection and conveyance devices that have components for such wicking or surface wetting deliberately included within them.

For conveying urine from point of collection to point of storage, simple substitution of a thin-walled tube for the thicker-walled ones such as are in current use would likely result in a poorer performance with respect to collapsing and sealing off of periodic, low volume flows such as urine incontinence leakage. Additionally, while any open tube may be used as a conduit channel for gravity-driven fluid flow, in order to provide active fluid transport in circumstances where the fluid path is ascendant to a higher point prior to reaching the descendent path, a simple open tube will not work (for example, when the user is seated, urine flow proceeding from the urethral meatus "up" the thigh to a higher point near the knee and thence flowing "down" to a storage container attached to the lower leg). Different technology is needed to accomplish these ends.

Storage Devices Background

In terms of storing collected urine in liquid form, the most widespread means in current use is a flexible-wall storage container that is connected to the collector via a conveyance tube and either is attached to the user's leg (hence the term, "leg bag") or is suspended from the waist. Such storage containers are designed to contain up to 450 cc of liquid urine (ca. 1-pint volume or one pound of weight). They are generally made from heavy-gauge film of latex rubber, vinyl, or similar polymer, made with a single storage chamber, and have some type of outlet valve at the bottom of the container for periodically draining the stored urine (e.g. into a toilet). They may also have a valve or inlet control at the conveyance tubing connection. The collected urine accumulates in the container to give a bulging, bulky volume of liquid that moves and sloshes around in response to the motions of the wearer. There are some containers with baffles or other internal attachments between the walls that are intended to limit the wall movement or bulging; however the overall container still bulges. In addition, the containers must be cleaned and disinfected regularly to avoid odor and buildup of microbiological contaminants when they are used for multiple collection cycles. Use patterns and user comments suggest that most containers are discarded after a short use period of 1–2 weeks. U.S. Pat. No. 4,846,816 describes a typical liquid urine storage container that is hung from the waist, and attached to the leg for stability, as part of a complete urine collection system for males. This container includes a manually operated drain valve to control urine discharge.

Storage devices containing liquid-absorbent materials are found in the prior art. For example, U.S. Pat. No. 4,246,901 discloses a urine collection system that includes a storage pouch container, which may be filled with a wicking material to store the collected urine. U.S. Pat. No. 4,360,932 discloses a disposable urine-collecting and storage device that incorporates an absorbent packed in cylindrical shapes that are packaged in a box-like container into which the user urinates.

Gel-forming polymeric absorbents are used in some urine-related applications. U.S. Pat. No. 5,007,116 discloses a urine collection container into which a healthy user may urinate and which contains a polymer to gel the urine. The polymer is initially confined in a teabag-like porous sack that will rupture and release the gel upon being wetted by the urine. U.S. Pat. Nos. 5,354,132 and 5,531,724 disclose bodily fluid containment bags that contain gelling materials to absorb bodily fluids, including urine, which the user transfers directly by urinating into the bags. These bags have inlet openings that also act as flapper closure devices to limit expulsion of the contained gelled fluids. The polymer absorbent, present in an amount that is described as capable of becoming fully gelled within 30 seconds and sufficient to essentially sequester the bodily fluids and to prevent them from being expelled from the bag, is placed in the bag without confinement to any area within the bag. Both U.S. Pat. No. 5,531,724 and related World Intellectual Property Organization # WO97/39705 disclose a fluid containment bag for gelling bodily fluids which has an opening for receiving those fluids from a catheter.

All of these describe the locus of the liquid absorption and gel formation in a single chamber envelope or bag with an inlet and containing gelling agent or absorbent either in a highly-confined mass or in an undefined shape. No provisions are described for deliberate distribution or mixing of the fluid to ensure rapid wetting and gel formation, nor are any provisions made for ensuring a particular shape or form of the absorbed or gelled fluid other than noting the geometrical shape of the envelope or bag. Moreover, placement of unconfined dry solids such as these absorbents in a bag with angular corners often results in accumulation in one corner or along one edge as a result of settling and movement during shipping and handling.

Based on these descriptions, prior art for absorptive gelling and solidification of urine in a storage container does not appear to recognize nor to make provision for "blinding", a physical characteristic of many chemical absorbents that can have a marked effect on their performance in the management of urine leakage for incontinent individuals. This is especially true for the gel-forming super-absorbent polymers. As absorbents begin to imbibe liquid, ones such as the gelling polymers are converted from solid particles to viscous, rubbery gels that swell as they absorb the liquid, developing an ever-thickening layer of gel that surrounds and coats the mass of as-yet unwetted material contained inside. The result is often seen as lumps or chunks of material, having an outer gel coating and containing much of the unused absorbent trapped inside, in a surrounding volume of unabsorbed liquid. Such partially or incompletely swollen gel materials take up liquid at a much slower rate than the dry materials because absorption of the additional liquid is slowed by a change in liquid absorption mechanism; the liquid being absorbed at a later time must move into the absorbent mass via diffusion, which is a much slower process than the surface absorption process initially operative. As a result, the outer layer of swollen gel absorbent becomes an impediment to rapid absorption of the liquid by the remainder of the unused absorbent, an effect frequently termed "blinding" or "blocking" of the incompletely wetted material. To a lesser extent, the same effect is seen in solid, inorganic water absorbents (such as calcium sulfate salts) which when absorbing water undergo changes in crystal structure while they remain in solid form. Such blinding can seriously delay the overall absorption of a liquid resulting in the inability of a given mass of solid absorbent to completely absorb an expected ratio of liquid, and consequently leaving free liquid remaining present for a much longer time than anticipated.

This blinding problem is common when liquid is added slowly without mixing to a mass of absorbent that is piled or packed in a shape that yields a minimum surface-to-volume ratio. This is just the situation that can occur for a urine-incontinent individual whose urine flow is generally delivered in small volume increments at moderate volumetric flow rates at frequent intervals. The result of the problem as perceived by the user can be a storage container filling with a fluid mixture of liquid urine and lumps of incompletely reacted absorbent which slowly absorb the free liquid urine.

If the solid and free liquid are subject to mixing, such as from mechanical stirring or even from the energy of the new liquid forcefully entering the absorption region, then the effect of blinding can be significantly reduced by the continuous break-up of the bulk of unreacted absorbent that exposes fresh dry surfaces before they become blinded. This is just the situation that occurs in single packages of absorbent materials when used by healthy individuals to collect and contain a full, forceful urination. Thus, the amount of absorbent added to the prior art urine gelling bags and the means of bringing the urine and absorbent together, while potentially sufficient to take up most of the urine from healthy individuals, may not be at all adequate to effectively immobilize the urine collected and confined in a storage container of undefined structure on the leg of an incontinent user.

Based on the above, the prior art absorption systems which are intended for healthy individual users and thus may require their urine flow rate and volume to provide the mixing forces required to ensure good absorption, are inadequate to ensure effective and acceptable performance when used by incontinent persons. The urine collection/disposal devices which are single chambers containing dry absorbents either in confined porous packages or distributed as solids in an undefined distribution such as appear in the prior art are all subject to potential blinding and blocking that will result in unpredictable liquid uptake performance and underutilization of absorbent.

The prior art approaches that employ a single envelope for all of the absorbent without means to control the end location of gelling absorption process also have no control on the distribution of the gelled solids after absorption of the urine. There are no means to ensure that the gelled solids will not end up mal-distributed with more of the material in one region such as the lower portion of the envelope, thus resulting in a container that is not of uniform shape or thickness and not at all conformable to body contours. Indeed, it may be less conformable than a current liquid leg bag without a gelling compound. A lumpy, non-conforming container may be useful as a one-time urinate-and-discard device, but it will not be acceptable for wearing for a finite time period by an incontinent user. In order to ensure effective performance, urine storage devices for incontinent users require more deliberate and uniform distribution of urine and of the absorbent materials than is disclosed in prior art. Different technology is needed to accomplish these ends.

Current liquid-storage leg bags rely on elasticized straps around the calf or suspension from a waist belt to maintain a desired position on the leg. Putting on these straps is tedious and time consuming. In addition, an improperly fastened leg bag may be more easily dislodged from the secure fastened position with consequent possible urine spillage. From the above, it is clear that the current-art technologies and products available to incontinent individuals who wish to use a system of devices to meet their personal urine management needs are inadequate. Improved means for storing and ultimately disposing of urine are needed.

The patents noted herein provide considerable information regarding the developments that have taken place in this field of technology. However, improved means for conveying urine are needed, in particular because none of the prior art meets the objects of providing the following for ambulatory incontinent individuals.

Urine collection and storage devices that accommodate the problems of ease of application, removal and changing.

Urine conduit devices that can be worn unnoticed, thus preserving privacy.

Urine collection, conveyance and storage devices that offer minimum potential for embarrassing leakage.

Urine storage devices that afford a convenient, discrete, and sanitary means for disposing of collected urine.

Accordingly, it is a primary object of the present invention to provide a urine management system that is comprised of a collection device, a conveyance tube, and a storage container, that accommodates ambulatory use, and that, in particular, addresses the problem of incontinence, overcoming the above-described limitations and disadvantages of the prior art.

A specific object of the present invention is to provide a urine conveyance tube that is readily adaptable to a range of routine human body motions and that will reliably conduct the flow of urine without blockage due to such motions. This tube connects a urine collection device with a urine storage device.

A further object of the present invention is to provide a urine conveyance tube that, can collapse to a flatter geometry when no fluid urine is in the lumen of the tube, and yet can also easily change in internal shape and dimensions so as to accommodate simultaneous, countercurrent flow of urine and atmospheric gases internal to the urine collection and storage devices.

A still further object of the present invention is to provide a urine conveyance tube whose internal lumen contains along its entire length a separating body that prevents complete blockage of fluid flow due to kinking, crimping, or otherwise collapsing.

A yet still further object of the present invention is to provide a urine conveyance tube that can, when desirable, accommodate ascending flow of urine, overcoming the force of gravity for a finite distance.

A yet still further object of this invention is to provide a urine conveyance tube that will have capability for limiting the growth of microbial organisms in that urine by maintaining antibacterial conditions at one or more locations along the urine flow path within the tube.

A yet still further object of the present invention is to provide a set of one or more devices for connecting this novel urine conveyance tube with novel collection devices and novel storage devices. These connecting devices can be combined with combinations of the novel urine conveyance tube and other urine handling devices to form kits of devices from which various urine management systems for incontinent individuals may be constructed.

A yet still further object of this invention is to provide an easy-to-use, secure, minimally protruding and comfortable means to store urine that has been conveyed from urine collection means.

A yet still further object of this invention is to provide a urine storage container that is readily adaptable to human body contours and movements, and that will reliably absorb urine conveyed to it, converting the urine to a form in which the urine no longer has liquid-like flow properties.

A yet still further object of the present invention is to provide a urine storage container that will provide a more uniform weight distribution than current urine storage leg bags. The container may be provided in flattened configuration which expands open only as it fills with urine. The container may be attached around the leg, worn attached and hanging from the waist, or worn attached to clothing.

A yet still further object of the present invention is to provide a urine storage container that can be shape-fitted around a limb and that can be self-tightening to maintain position as the container fills with urine.

A yet still further object of the present invention is to provide a storage container containing an absorbent or gel-forming polymer that will, when contacted with the conveyed urine, become partially or wholly filled with absorbed or gelled liquid that does not move or flow like a liquid when the container wearer moves.

A yet still further object of the present invention is to provide a storage container that will convey and distribute liquids to be absorbed such as urine by wicking or other distributive means into the immediate vicinity of unused or partially used absorbent material so as to facilitate fluid transfer to the absorbent materials which are intended to absorb that increment of liquid.

A yet still further object of this invention is to provide a storage container that ill have the capability for limiting the growth of microbial organisms in that urine by maintaining antibacterial conditions at one or more locations along the urine flow path within the storage container.

A yet still further object of the present invention is to provide a single-use storage container that may be made of lightweight materials. Without the need to withstand multiple cycles of cleaning and reuse, the wall structure of the storage container does not need to be especially heavy or rugged. A single-use storage container eliminates cleaning of the storage container and assures cleanliness and freedom from residual urine odor. The storage container may be provided in internally sterile condition, if so desired.

A yet still further object of the present invention is to provide a storage container that, together with its content of absorbed or gelled urine, can be disposed of as sanitary solid waste.

A yet still further object of the present invention is to provide a storage container in which no drain opening for liquids is needed, thus avoiding that significant source of accidental leakage from liquid storage containers.

A yet still further object of the present invention is to provide a storage container that will facilitate absorption of liquids delivered from other storage containers.

A yet still further object of the present invention is to provide a set of one or more devices for connecting this novel urine storage container with currently existent devices for collecting, conveying, and storing urine. These connecting devices can be combined with combinations of this novel urine storage container and existent urine handling devices to form kits of devices from which various urine management systems for incontinent individuals may be constructed.

A yet still further object of the present invention is to provide an easy-to-use, secure, leak-free, minimally visible, and health-promoting urine collection device for human males.

A yet still further object of the present invention is to provide a urine collection device for human males that is easy to put on and remove, that provides a urine-resistant leak seal, and that will reliably transfer urine emitted from the penile urethral opening to a conveyance device for transfer to storage.

A yet still further object of the present invention is to provide a urine collection device that will remove residual drops and pools of urine, especially those in contact with the users skin, and will promote the exchange of atmosphere next to the penile skin, thus promoting the health of those skin surfaces.

A yet still further object of the present invention is to provide a urine collection device for human males that can be easily and conveniently applied to the penis.

A yet still further object of the present inventions is to provide a urine collection device for human males that will adhere to the penis in any condition of the organ without the need for adhesives or similar adherent materials.

A yet still further object of the present inventions is to provide a urine collection device for human males that will remove any freestanding pools or drops of urine from the collection device and transport that urine to the conduit tube for removal.

A yet still further object of this invention is to provide a urine collection device that will have the capability for limiting the growth of microbial organisms in that urine by maintaining antibacterial conditions at one or more locations along the urine flow path within the collection device.

A yet still further object of the present invention is to provide a set of one or more devices for connecting this novel urine collection device with currently existent devices for conveying and storing urine. The connecting devices can be combined with combinations of this novel urine collection device and the existent urine handling devices to form kits of devices from which various urine management systems for incontinent individuals may be constructed.

A yet still further object of this invention is to provide a novel urine management system that, in addition to performing its functions of urine collection, conveyance, and storage, will also provide capability to remove residual liquid urine remaining in the collector and conveyance devices after the aforementioned functions are completed.

A yet still further object of this invention is to provide a novel urine management system that will provide enhanced capability to remove residual liquid urine that is not removed from the collection device and the conveyance device by gravity drainage. Removal of this residual urine will minimize excessive exposure of penis skin to the moisture and decomposition products from this residual urine can result in injury to that skin.

A yet still further object of this invention is to provide a novel urine management system that will have capability for gathering residual urine and for limiting the growth of microbial organisms in that urine, thereby minimizing the potential for introduction of any system-generated microorganisms into the urinary tract of the user. By facilitating the gathering of isolated pools of residual liquid urine into the wicking, and by maintaining antibacterial conditions at one or more locations along the urine flow path within the management system, both the growth of such infectious agents and transport into the urethral region will be discouraged.

A yet still further object of this invention is to provide a set of one or more devices for serially-connecting the novel devices for collecting, conveying, and storing urine such that the several contiguous connections of wicking and wetting components are maintained.

A yet still further object of this invention is to provide a system for collecting, conveying, and storing urine discharged from a human male comprising means for collection of urine from a human male comprising proximal and distal ends and outer and inner surfaces; means for storage of urine before disposal of urine comprising proximal and distal ends and outer and inner surfaces; means for conveying urine from the means for collection of urine to means for storage of urine comprising proximal and distal ends and outer and inner surfaces; and means for wicking urine away from a human male wherein the means for wicking moves urine away from a human male through the means for collection and the means for conveyance, and deposits the urine in the means for storage. The system further comprises a first means of connection which connects the means for collection with the means for conveying and which comprises an outer surface and an inner surface; and a second means of connection which connects the means for conveying with the means for storage and which comprises an outer surface and an inner surface, wherein the first means of connection is selected from a group consisting of fixed and removable, and the second means of connection is selected from a group consisting of fixed and removable, and wherein the distal end of the means for collection is connected to the proximal end of the means for conveyance through the first means for connection, and the distal end of the means for conveyance is connected to the proximal end of the storage device through the second means for connection. The first means for connection further comprises a collector-conveyance connector; and a conveyance-collector connector; and the second means for connection comprises a storage-conveyance connector; and a conveyance-storage connector, wherein the conveyance-collector connector forms the proximal end of the means for conveyance, the collector-conveyance connector forms the distal end of the means for collection, the conveyance-storage connector forms the distal end of the means for conveyance, and the storage-conveyance connector forms the proximal end of the means for storage.

A yet still further object of this invention is to provide a system for collecting, conveying, and storing urine discharged from a human male wherein the means for wicking comprises a first wicking spacer disposed within the means for collection; and a second wicking spacer disposed within the means for conveying, and a third wicking spacer disposed within the means for storage of the urine; wherein the first wicking spacer piece forms contiguous wicking connections between the first wicking spacer and the second wicking spacer; and the second wicking spacer piece forming contiguous wicking connections between the second wicking spacer and the third wicking spacer, wherein the first wicking spacer, the first wicking spacer piece, the second wicking spacer, the second wicking spacer piece, and the third wicking spacer collectively form a complete wicking path from the means for collection to the means for storage that can transmit urine both anti-gravitationally.

A yet still further object of this invention is to provide a system for collecting, conveying, and storing urine discharged from a human male comprising at least one continuous urine impervious shell disposed on the outer surface of the means for collection, the outer surface of the means for storage, and the outer surface of the means of conveying.

A yet still further object of this invention is to provide a system for collecting, conveying, and storing urine discharged from a human male wherein the means for wicking comprises a material selected from a group consisting of rayon acetate needled felting; single component fibers selected from a group consisting of wool, cotton, rayon, nylon, and polyester; blended fibers selected from a group consisting of wool, cotton, rayon, nylon, and polyester; the single component and the blended fibers fabricated into a form selected from a group consisting of yarns, woven fabrics, mats, and felts; open-cell foamed polymers, elastomers such as polyurethane foams; open-mesh materials such as steel wool; meshes of synthetic polymers such as polypropylene; and flexible solids such as latex.

A yet still further object of this invention is to provide a system for collecting, conveying, and storing urine discharged from a human male wherein the means for collection comprises a means for wicking the urine away from the penis; a thin-wall hollow conduction tube having proximal and distal ends and a cavity sufficiently large to surround the penis; and a compression tube having proximal and distal ends and sufficient size to be disposed around and provide radial compression contact upon the penis at the proximal end of the conduction tube, wherein the means for wicking is disposed within the conduction tube.

A yet still further object of this invention is to provide a system for collecting, conveying, and storing urine discharged from a human male wherein the compression tube for securing a liquid collection device onto the penis of a human male comprises a thin-wall material having exterior and interior surfaces from which the compression tube is constructed; means for expanding the compression tube wherein the means for expanding is attached to the thin-wall material for opening the compression tube to insert the penis; collection device interface; and wherein the compression tube is properly sized to provide an area of radial compression contact on the conduction tube that is sufficient to minimize the slippage of the conduction tube and to seal against leakage of the urine from the means for collection, and further wherein the means for securing the sheath tube to the penis shaft comprises elastic-like material from which the sheath tube is fabricated.

A yet still further object of this invention is to provide a system for collecting, conveying, and storing urine discharged from a human male wherein the compression tube proximal end is connected to the conduction tube proximal end and is properly sized to provide an area of radial compression contact on the penis that is sufficient to minimize the slippage of the compression tube and to seal against leakage of the urine between the penis and the compression tube.

A yet still further object of this invention is to provide a system for collecting, conveying, and storing urine discharged from a human male wherein the conduction tube comprises a material selected from a group consisting of thin-wall PE "lay-flat" tubing, rubbery polymer, silicone rubber, latex rubber, polyolefin, flexible film material, fabrics, elastic, and elasticized fabric wherein the material is physically flexible, facilitates liquid sealing, and enables frictional stability of the collection device when worn by the human male.

A yet still further object of this invention is to provide a system for collecting, conveying, and storing urine discharged from a human male wherein the thin-wall material of the compression tube comprises at least one layer and is selected from a group consisting of woven elastomeric fabric, non-woven elastic fabric, elastic fiber-containing fabric, elastomeric sheeting made from latex rubber, and elastomeric sheeting made from silicone rubber wherein the material is adaptable to waterproof coating and wherein the material, after waterproof coating, can still allow evaporation of water vapor from the penis.

A yet still further object of this invention is to provide a system for collecting, conveying, and storing urine discharged from a human male wherein the compression tube distal end is connected to the collection device interface proximal end and the conduction tube proximal end is connected to the collection device interface distal end, the compression tube is properly sized to provide an area of radial compression contact on the penis that is sufficient to minimize the slippage of the compression tube and to seal against leakage of the urine between the penis and the compression tube.

A yet still further object of this invention is to provide a system for collecting, conveying, and storing urine discharged from a human male wherein the means for expanding the compression tube comprises at least two tube-spreading tools each having at least one leg and at least one tip; and at least two receiving openings disposed upon the perimeter of the thin-wall material for holding in place the tube-spreading tool, wherein the tool-spreading tool tips fit into the receiving openings to be used in opposition for expanding the compression tube.

A yet still further object of this invention is to provide a system for collecting, conveying, and storing urine discharged from a human male wherein the tube-spreading tool tip is long enough to enlarge the entire length of the compression tube.

A yet still further object of this invention is to provide a system for collecting, conveying, and storing urine discharged from a human male wherein the receiving openings have a form selected from a group consisting of one or more recesses along the perimeter of the compression tube and loops of fabric or fiber.

A yet still further object of this invention is to provide a system for collecting, conveying, and storing urine discharged from a human male wherein each the tube-spreading tool is disposed with two handles that are connected to and operate in scissors-like cooperation with the tube-spreading legs in mated pair such that when one the handle is moved towards the other the handle, one the leg moves away from the other the leg.

A yet still further object of this invention is to provide a system for collecting, conveying, and storing urine discharged from a human male wherein the tube-spreading tool is an integral part of the compression tube.

A yet still further object of this invention is to provide a system for collecting, conveying, and storing urine discharged from a human male further comprising a human ale penis tip inserted into the means for collection wherein the first wicking spacer disposed within the means for collection is located between the penis tip and the first means of connection.

A yet still further object of this invention is to provide a system for collecting, conveying, and storing urine discharged from a human male wherein the means for wicking comprises first wicking spacer disposed within the means for collection; second wicking spacer disposed within the means for conveying, third wicking spacer disposed within the means for storage of the urine; first wicking spacer piece forming contiguous wicking connections between the first wicking spacer and the second wicking spacer; and second wicking spacer piece forming contiguous wicking connections between the second wicking spacer and the third wicking spacer, wherein the first wicking spacer, the first wicking spacer piece, the second wicking spacer, the second wicking spacer piece, and the third wicking spacer collectively form a complete wicking path from the means for collection to the means for storage, and further comprising a human male penis tip inserted into the means for collection wherein the first wicking spacer disposed within the means for collection is located between the penis tip and the collector-conveyance connector.

A yet still further object of this invention is to provide a system for collecting, conveying, and storing urine discharged from a human male wherein the first wicking spacer comprises a y-shape having a tail and two legs such that the legs of the y-shape lie in proximity to the interior surface of the means for collection.

A yet still further object of this invention is to provide a system for collecting, conveying, and storing urine discharged from a human male wherein the means for collection comprises slitted sheath tube having left and right slit flaps and a tube cavity sufficiently large to surround the penis; means for securing the left slit flap to the right slit flap; and means for wicking the urine away from the penis that is disposed within the slitted sheath tube, wherein the slitted sheath tube is held in place on the penis by the means for securing, and wherein the means for securing the left slit flap to the right slit flap comprises multiple hook-and-loop fasteners or a zip-lock-type fastener.

A yet still further object of this invention is to provide a system for collecting, conveying, and storing urine discharged from a human male wherein the means for collection comprises sheath tube having a tube cavity sufficiently large to surround the penis and an opening radial edge; means for covering the penis with the sheath tube; means for securing the sheath tube to the penis; and means for wicking the urine away from the penis that is disposed within the sheath tube, wherein the sheath tube is held in place on the penis by the means for securing.

A yet still further object of this invention is to provide a system for collecting, conveying, and storing urine discharged from a human male wherein the means for covering the penis, having tip and shaft, with the sheath tube comprises a ring of expandable tubing sized to fit the penis shaft, wherein the ring is fixedly connected to the sheath tube opening radial edge, the sheath tube is rolled upon the expandable tubing, and the sheath is rolled off of the expandable tubing starting from the penis tip and traveling up the penis shaft until the sheath is fully extended, and wherein the means for securing the sheath tube to the penis shaft comprises the ring of expandable tubing.

A yet still further object of this invention is to provide a system for collecting, conveying, and storing urine discharged from a human male wherein the means for covering the penis, having tip and shaft, with the sheath tube comprises a rigid plastic bellows expandable to fit the penis shaft, wherein the bellows is removably connected to the sheath tube opening radial edge, the sheath tube is rolled upon the expandable bellows, the sheath is rolled off of the expandable bellows starting from the penis tip and traveling up the penis shaft until the sheath is fully extended, and the bellows are removed from the sheath tube, and wherein the means for securing the sheath tube to the penis shaft comprises elastic-like material from which the sheath tube is fabricated.

A yet still further object of this invention is to provide a system for collecting, conveying, and storing urine discharged from a human male wherein the means for covering the penis, having tip and shaft, with the sheath tube comprises a spring expandable to fit the penis shaft; and a toothed plastic strap disposed within the spring that allows the spring to expand but not contract, wherein the spring/strap combination is removably connected to the sheath tube opening radial edge, the sheath tube is rolled upon the expandable spring/strap, the sheath is rolled off of the expandable spring/strap starting from the penis tip and traveling up the penis shaft until the sheath is fully extended, and the spring/strap is removed from the sheath tube, and further, the means for securing the sheath tube to the penis shaft comprises elastic-like material from which the sheath tube is fabricated.

A yet still further object of this invention is to provide a system for collecting, conveying, and storing urine discharged from a human male wherein the means for covering the penis having tip and shaft with the sheath tube comprises a jaw ring expander for extending the sheath the length of the penis shaft comprising hand rest having hand end and ring end wherein a user grasps the hand rest at the hand end; expandable jaw ring having means for connection to the ring end of the hand rest; and lever having means of connection to the hand end of the hand rest, wherein the expandable jaw ring expands when the lever is depressed by the user, the sheath is draped over the expandable jaw ring, the sheath is moved longitudinally up the penis shaft by the expandable jaw ring, the sheath contracts to fit the penis, and the lever is depressed to expand the expandable jaw ring sufficiently to remove the expandable jaw ring from the penis, and further, the means for securing the sheath tube to the penis shaft comprises elastic-like material from which the sheath tube is fabricated.

A yet still further object of this invention is to provide a system for collecting, conveying, and storing urine discharged from a human male wherein the means for conveyance comprises waterproof conveyance tube film layer; conveyance tube having an exterior surface upon which the waterproof conveyance tube film layer is disposed and a hollow interior into which the penis is placed; means for wicking the urine through the conveyance tube wherein the means for wicking prevents the interior of the conveyance tube from becoming blocked when crimped or kinked; wherein the means for wicking is disposed within the conveyance tube film layer and the combination of the means for wicking with the film layer is sufficiently flexible to conform to normal bodily movement and position.

A yet still further object of this invention is to provide a system for collecting, conveying, and storing urine discharged from a human male wherein the means for wicking comprises a material, having internal structure and external surface, wherein the internal structure is flexible, of low density so as not to add substantial weight to the conveyance tube, open/porous, and relatively more wettable by water than polyolefins, and wherein the surface is rough.

A yet still further object of this invention is to provide a system for collecting, conveying, and storing urine discharged from a human male wherein the means for wicking is selected from a group consisting of rayon felt having a width from approximately 15 to 50 mm (0.6 to 2 inch) and a thickness from approximately 2.54 to 5.08 mm (0.1 to 0.2 inch); bonded cellulose acetate fiber bundle; nylon mesh; and polyethylene films in 3- to 10-mil thickness.

A yet still further object of this invention is to provide a system for collecting, conveying, and storing urine discharged from a human male wherein the waterproof conveyance tube film layer is selected from a group consisting of a wettable material and a material that has been subjected to surface treatments to render that the conveyance tube film layer wettable for holding liquid.

A yet still further object of this invention is to provide a system for collecting, conveying, and storing urine discharged from a human male wherein the means for storage comprises means for wicking the urine into and within the means for storage; means for directing the urine into specific parts of the means for storage; means for absorbing the urine within the means for storage; and means for retaining the urine within the means for storage, the means for wicking, the transport channel, the barrier wall, and the urine absorption element are all enclosed in the urine impervious outer walls wherein the outer edges of the urine impervious outer walls are sealed by a means selected from a group consisting of folding, thermal bonding, and adhesive bonding, and further, wherein the means for directing the urine into specific parts of the means for storage comprises barrier walls and compartment-defining lines, and still further, wherein the means for storage comprises straps connected to the means for storage for mounting the means for storage onto the human male.

A yet still further object of this invention is to provide a system for collecting, conveying, and storing urine discharged from a human male further comprising means for mounting the means for storage onto the human male.

A yet still further object of this invention is to provide a system for collecting, conveying, and storing urine discharged from a human male wherein the conveyance tube comprises thin-wall material.

A yet still further object of this invention is to provide, in creating an opening for inserting a human male penis into an expandable urine collection tube disposed with receiving openings along the perimeter of the urine collection tube, a method for using a tube-spreading tool having at least two legs each attached to at least one tip comprising inserting the tips of the tube-spreading tool into the receiving openings; applying pressure to the legs to expand the expandable urine collection tube to form a cavity within the urine collection tube; inserting the penis into the cavity; releasing the pressure on the legs wherein the urine collection tube compresses on the penis; and removing the tips of the tube-spreading tool from the receiving openings.

A yet still further object of this invention is to provide a urine collection device for collecting urine from the penis of a human male comprising thin-wall hollow conduction tube having proximal and distal ends and a cavity sufficiently large to surround the penis; means for wicking the urine away from the penis that is disposed within the conduction tube; and compression tube having proximal and distal ends and sufficient radial size at the proximal end to be disposed around and provide radial compression contact upon the penis and the proximal end of the conduction tube, and further, wherein the means for wicking is disposed primarily within the distal end of the conduction tube, and still further wherein the compression tube is properly sized to provide radial compression contact on the conduction tube that is sufficient to minimize the slippage of the conduction tube and to seal against leakage of the urine between the penis and the conduction tube, and yet still further, wherein the compression tube distal end is connected to the conduction tube proximal end and is properly sized to provide an area of radial compression contact on the penis that is sufficient to minimize the slippage of the compression tube and to seal against leakage of the urine between the penis and the compression tube, and yet still further, wherein the conduction tube comprises a material selected from a group consisting of thin-wall PE "lay-flat" tubing, rubbery polymer, silicone rubber, latex rubber, polyolefin, flexible film material, fabrics, elastic, and elasticized fabric wherein the material is physically flexible, facilitates liquid sealing, and enables frictional stability of the collection device when worn by the human male, and yet still further, wherein the wicking comprises a material selected from a group consisting of rayon felt, and yet still further, comprising a means for expanding the compression tube comprising at least two tube-spreading tools each having at least one leg and at least one tip; and at least two receiving openings disposed upon the perimeter of the thin-wall material for holding in place the tube-spreading tool, wherein the tool-spreading tool tips fit into the receiving openings to be used in opposition for expanding the compression tube, and yet still further, wherein the tube-spreading tool tip is long enough to enlarge the entire length of the compression tube, and yet still further, wherein the receiving openings have a form selected from a group consisting of one or more recesses along the perimeter of the compression tube and loops of fabric or fiber, and yet still further, wherein each the tube-spreading tool is disposed with two handles that are connected to and operate in scissors-like cooperation with the tube-spreading legs in mated pair such that when one the handle is moved towards the other the handle, one the leg moves away from the other the leg, and yet still further, wherein the tube-spreading tool is an integral part of the compression tube, and yet still further, wherein the first wicking spacer comprises a y-shape having a tail and two legs such that the legs of the y-shape lie in proximity to the interior surface of the conduction tube.

A yet still further object of this invention is to provide a urine collection device for collecting urine from the penis of a human male comprising slitted sheath tube having left and right slit flaps and a tube cavity sufficiently large to surround the penis; means for securing the left slit flap to the right slit flap; and means for wicking the urine away from the penis that is disposed within the slitted sheath tube, wherein the slitted sheath tube is held in place on the penis by the means for securing, and further, wherein the means for securing the left slit flap to the right slit flap comprises multiple hook-and-loop fasteners, and yet further, wherein the means for securing the left slit flap to the right slit flap comprises a zip-lock-type fastener.

A yet still further object of this invention is to provide a urine collection device for collecting urine from the penis of a human male comprising sheath tube having a tube cavity sufficiently large to surround the penis and an opening radial edge; means for covering the penis with the sheath tube; means for securing the sheath tube to the penis; and means for wicking the urine away from the penis that is disposed within the sheath tube, wherein the sheath tube is held in place on the penis by the means for securing, and further wherein the means for covering the penis, having tip and shaft, with the sheath tube comprises a ring of expandable tubing sized to fit the penis shaft, wherein the ring is fixedly connected to the sheath tube opening radial edge, the sheath tube is rolled upon the expandable tubing, and the sheath is rolled off of the expandable tubing starting from the penis tip and traveling up the penis shaft until the sheath is fully extended, and further wherein the means for securing the sheath tube to the penis shaft comprises the ring of expandable tubing, and yet further, wherein the means for covering the penis, having tip and shaft, with the sheath tube comprises a rigid plastic bellows expandable to fit the penis shaft, wherein the bellows is removably connected to the sheath tube opening radial edge, the sheath tube is rolled upon the expandable bellows, the sheath is rolled off of the expandable bellows starting from the penis tip and traveling up the penis shaft until the sheath is fully extended, and the bellows are removed from the sheath tube, and yet still further, wherein the means for securing the sheath tube to the penis shaft comprises elastic-like material from which the sheath tube is fabricated.

A yet still further object of this invention is to provide a urine collection device wherein the means for covering the penis, having tip and shaft, with the sheath tube comprises a spring expandable to fit the penis shaft; and a toothed plastic strap disposed within the spring that allows the spring to expand but not contract, wherein the spring/strap combination is removably connected to the sheath tube opening radial edge, the sheath tube is rolled upon the expandable spring/strap, the sheath is rolled off of the expandable spring/strap starting from the penis tip and traveling up the penis shaft until the sheath is fully extended, and the spring/strap is removed from the sheath tube, and further, wherein the means for securing the sheath tube to the penis shaft comprises elastic-like material from which the sheath tube is fabricated.

A yet still further object of this invention is to provide a urine collection device wherein the means for covering the penis having tip and shaft with the sheath tube comprises a jaw ring expander for extending the sheath the length of the penis shaft comprising hand rest having hand end and ring end wherein a user grasps the hand rest at the hand end; expandable jaw ring having means for connection to the ring end of the hand rest; and lever having means of connection to the hand end of the hand rest, wherein the expandable jaw ring expands when the lever is depressed by the user, the sheath is draped over the expandable jaw ring, the sheath is moved longitudinally up the penis shaft by the expandable jaw ring, the sheath contracts to fit the penis, and the lever is depressed to expand the expandable jaw ring sufficiently to remove the expandable jaw ring from the penis, and further, wherein the means for securing the sheath tube to the penis shaft comprises elastic-like material from which the sheath tube is fabricated.

A yet still further object of this invention is to provide a compression tube having proximal and distal ends for securing a liquid collection device onto the penis of a human male comprising thin-wall tube having interior and exterior surfaces; means for expansion; and collection device interface, wherein the thin-wall tube surrounds the penis through the means for expansion and secures the collection device onto the penis through the collection device interface, and further, wherein the thin-wall material comprises at least one layer and is selected from a group consisting of woven elastomeric fabric, non-woven elastic fabric, elastic fiber-containing fabric, elastomeric sheeting made from latex rubber, and elastomeric sheeting made from silicone rubber wherein the material is adaptable to waterproof coating and wherein the material, after waterproof coating, can still allow evaporation of water vapor from the penis, and further, wherein the compression tube distal end is connected to the collection device interface proximal end and the conduction tube proximal end is connected to the collection device interface distal end, the compression tube is properly sized to provide an area of radial compression contact on the penis that is sufficient to minimize the slippage of the compression tube and to seal against leakage of the urine between the penis and the compression tube, and yet further, wherein the means for expanding the compression tube comprises at least two tube-spreading tools each having at least one leg and at least one tip; and at least two receiving openings disposed upon the perimeter of the thin-wall material for holding in place the tube-spreading tool, wherein the tool-spreading tool tips fit into the receiving openings to be used in opposition for expanding the compression tube, and yet still further, wherein the tube-spreading tool tip is long enough to enlarge the entire length of the compression tube, and yet still further, wherein the receiving openings have a form selected from a group consisting of one or more recesses along the perimeter of the compression tube and loops of fabric or fiber, and yet still further, wherein each the tube-spreading tool is disposed with two handles that are connected to and operate in scissors-like cooperation with the tube-spreading legs in mated pair such that when one the handle is moved towards the other the handle, one the leg moves away from the other the leg, and yet still further, wherein the tube-spreading tool is an integral part of the compression tube, and yet still further, comprising a human male penis tip inserted into the means for collection wherein the first wicking spacer disposed within the means for collection is located between the penis tip and the first means of connection.

A yet still further object of this invention is to provide a method for pretreating with rayon felt and liquid cleaner a urine collection tube having an interior surface for collecting urine from human males comprising wetting the rayon felt with the liquid cleaner; wiping the interior surface completely with the wetted rayon felt; and allowing the interior surface to dry for at least one hour at room temperature so that the interior surface enabled the urine collection device to draw the urine away from the point of collection of the human male, and yet further, comprising inflating the urine collection tube with air in order to break the wall-to-wall adhesion of the tube.

A yet still further object of this invention is to provide a process for rendering the interior surface of a urine collection tube wettable by water selected from a group consisting of pretreatment by corona discharge, pretreatment by flame, and retreatment by liquid cleaner.

A yet still further object of this invention is to provide a method for manufacturing a compression tube, having interior and exterior surfaces, for stabilizing and securing the location of a urine collection tube and liquid sealing the compression tube using liquid rubber cement, spandex fabric, latex rubber, and rayon felt comprising connecting a rectangle of the spandex fabric to itself along its short edges; lightly coating portions of the interior surface of the compression tube with the liquid rubber cement; allowing the interior surface coating to dry; coating the exterior surface of the compression tube with the liquid rubber cement; bonding a sheet of the latex rubber to the exterior surface of the compression tube where the exterior surface was coated with the liquid rubber cement; and attaching a strip of the rayon felt to the interior surface of the compression tube.

A yet still further object of this invention is to provide a method for use of a urine collection system for a human penis having a conduction tube having interior and exterior surfaces and a compression tube having interior and exterior surfaces comprising applying friction enhancer coating to portions of the compression tube; applying at least one circumferential ring of fluid impervious coating to the surface of the penis and not coincident with the friction enhancer coating wherein the coating is a material selected from a group consisting of urine resistant cream and urine resistant jelly product; extending the conduction tube proximally along the shaft of the penis; extending the compression tube adjacent to the conduction tube proximally along the shaft of the penis wherein the compression tube overlays the conduction tube for a distance sufficient such that the compression tube is completely underlain by the conduction tube and the compression tube provides compression onto the conduction tube so that both the tube and the tube remain in position on the penis, and further, wherein the friction enhancer coating is latex rubber, and yet further, wherein the fluid impervious coating is a material selected from a group consisting of silicone rubber of low durometer and foamed polymer having elastomeric properties.

A yet still further object of this invention is to provide a method for use of a urine collection system for a human penis having a conduction tube having interior and exterior surfaces and a compression tube having interior and exterior surfaces and proximal and distal ends comprising attaching the conduction tube to the compression tube forming a conduction tube/compression tube combination; applying friction enhancer coating to portions of the compression tube; applying at least one circumferential ring of fluid impervious coating to the surface of the penis and not coincident with the friction enhancer coating wherein the fluid impervious coating is a material selected from a group consisting of urine resistant cream and urine resistant jelly product; extending the conduction tube/compression tube combination proximally along the shaft of the penis wherein the compression tube provides compression onto the penis so that the conduction tube/compression tube combination remains in position on the penis, and further, wherein the friction enhancer coating is latex rubber, and further, wherein the fluid impervious coating is a material selected from a group consisting of silicone rubber of low durometer and foamed polymer having elastomeric properties, and yet further, comprising enlarging the compression tube to fit over the penis wherein the enlarging step is accomplished by applying outward tension forces to open the compression tube at the proximal end.

A yet still further object of this invention is to provide a method of use for a system for collecting, conveying through a tube, and storing urine discharged from a human male comprising collecting the urine from incontinence leakage from the human male; conveying the urine through said tube; storing said urine in immobilized form in a means for storage; filling said first means for storage to its capacity; replacing said first means for storage when it has reached said capacity with second means for storage; and disposing of said first means for storage as solid sanitary waste.

A yet still further object of this invention is to provide a conveyance tube for conveying urine from a human male collection device to a urine storage device comprising a conduction tube having walls of any thickness and an interior cavity within said walls; and wicking spacer disposed within said conduction tube wherein said wicking spacer wicks said urine away from said collection device and prevents said conveyance tube from completely collapsing when said interior cavity is empty, and further, wherein said conduction tube comprises a material having thin walls of varying cross-section selected from a group consisting of rubbery polymer such as silicone rubber, latex rubber, elastic or elasticized fabric coated; polyolefins; latex; and Polymeric film, and further, wherein said wicking spacer comprises knitted nylon, and further, wherein said conduction tube is flat tube when said interior cavity is empty of said urine and inflated when said interior cavity is filled with said urine, and yet further, wherein said wicking spacer is connected to said interior cavity of said conduction tube, and yet still further, wherein said interior cavity of said conduction tube comprises a wettable material.

A yet still further object of this invention is to provide a means for storage of liquid urine collected through a means for collection from an incontinent and mobile human male comprising storage container for said liquid urine having an outer shell and an inner cavity; and spacer wicking disposed within said storage bag to store said urine within said storage container, and further, wherein said inner cavity of said storage container is divided into areas to facilitate immobilization of said urine within said storage container and is coated with a gel selected from a group consisting of polyacrylamide, polyacrylic acid: Na+ salt, polyacrylic acid: Na+ salt on starch, resin fine particles in paper fiber matrix, needled felt pads, absorbent paper towels, and gel resin combined with inorganic absorbent, and yet further, comprising absorbent material disposed within said inner cavity of said storage container selected from a group consisting of super absorbent polymers, cellulose, cellulose-derived materials, and wettable, fibrous materials, and yet still further, comprising a means for distributing said urine throughout said inner cavity of said storage container, and yet still further, comprising a means for attaching said storage container to said human male, and yet still further, wherein said means for attaching said storage container comprises leg straps attached to said outer shell of said storage container for wrapping around the leg of said human male, and yet still further, comprising a means for connecting said storage container to said means for collection, and yet still further, wherein the material of said outer shell of said storage container is selected from a group consisting of thin polymer film and heavy polymer film, and yet still further, wherein said storage container is disposable as sanitary waste.

A yet still further object of this invention is to provide a system for collecting, conveying, and storing urine discharged from a human male wherein said urine is transported upgradient from said urine collection device through said conveyance tube.

A yet still further object of this invention is to provide a method for use of a human urine management system comprising a urine collection device, a thin-walled flat tube containing wicking and spacers, a means for attaching said tube to said human, a storage container, a means for attaching said storage container to said human, and a means for presenting a fresh storage container, said method comprising attaching said urine collection device to said human; attaching said tube to said urine collection device; attaching said tube to said human via said means for attaching said tube; attaching said storage container to said tube; attaching said storage container to said human via said means for attaching said storage container; depositing urine into said urine collection device; and changing said storage container when said container is full, and yet further, wherein said storage container is disposable, and yet still further, wherein said storage container is reusable.

Additional objects, advantages, and other novel features of the invention will be set forth in part in the description that follows and in part will become apparent to those skilled in the art upon examination of the invention. The objects and advantages of the invention may be realized and obtained by means of the instrumentalities and combinations particularly pointed out in the appended claims.

DESCRIPTION OF THE INVENTION

To achieve the foregoing and other objects, and in accordance with the purposes of the present invention as described herein, an improved urine management system for incontinent human males is disclosed. The improved urine management system is formed by the serial connection of functional devices comprising a novel urine collection device, a novel urine conveyance device and a novel urine storage device. The system is intended to provide for collection of incontinent urine leakage, for conveyance of said collected urine to the storage device, and for conversion of said urine to an immobilized form and storage of same prior to disposal of said immobilized urine as a sanitary waste.

None of the prior art examples cited heretofore are as effective or as efficient as the instant invention in meeting the needs of incontinent persons, and especially ambulatory ones, because of the combination of novel technologies and approaches provided through this invention, including:

Thin-walled or any thickness, flat tube for conducting urine from collection to storage: expands only when conducting urine flow, and contains spacer device to prevent crimping blockage of flow;

Wicking mechanism within the tube and system to draw the fluid up to a point of collection that is higher than the source;

Wettable surfaces and continuous wicking in collection and conveyance system enables more complete and effective removal of urine wetness and products injurious to sensitive skin;

Regions in the wicking flow path of each device that are treated with suitable antibacterial materials to limit the growth of undesirable microorganisms in urine passing through the region;

Novel uniform compression tube in collection device provides more secure attachment and better seal between collector tube and penis with minimum irritation during application, use, or removal;

Multicompartment storage package with urine distribution system;

Thin, flat, multicompartment storage package gives more uniform weight distribution than current liquid leg bag, expanding open only as it fills with urine;

Tubing and Storage package that can be attached to leg or clothing;

Single-use storage package made of lightweight, thin polymer film, that is waterproof and gas tight to ensure cleanliness and lack of odor;

Storage package that minimizes movement of immobilized, stored liquid when the wearer moves;

Storage package disposable as solid sanitary waste;

Storage package that has no vent or drain valve, thus avoiding significant sources accidental leakage in liquid storage packages;

Storage packages of various sizes and capacities to suit various needs; and

Minimal disturbance to the wearer's skin surfaces.

Collection Device

A urine collection device for human males that can be used in the urine management systems of incontinent individuals to collect and transfer the urine to a conveyance device for subsequent conveyance to storage is disclosed. The collection device comprises a flexible conduction tube to confine emitted urine while that urine is being transferred to the conveyance device, an elastic compression tube to hold and to seal the conduction tube onto the penis, wicking components and wettable surfaces to aid urine transfer within the conduction tube, and a spacer component to prevent cutoff of the urine flow through the conduction tube due to crimping of the tube walls. The conduction tube may be joined distally to the elastic compression tube, or it may be separate from the elastic compression tube being located between the penis surface and the compression ring and of sufficient length to enclose the penis past the distal end of the elastic compression ring.

The conduction tube wall can be any thickness, and in one embodiment is a thin-walled tube whose cross-sectional area can vary at various locations along the length. Within the conduction tube are an open-channel lumen for collecting and transferring free-flowing liquid urine to the conveyance device, and wicking and urine-wettable inner surfaces for collecting and transferring drops or pools of urine from within the region between the penis and the distal interior end of the collection device to the conveyance device. The conduction tube may also have within its lumen, a spacer (a separating element) to prevent the open channel from being completely closed off to fluid flow by kinks or crimps in the sidewall of the conduction tube.

The wall of the conduction tube, any thickness but can be thin-walled, can be made of a rubbery polymer such as silicone rubber or latex rubber or an elastic or elasticized fabric when said fabrics are coated with a material that will prevent urine leakage. The conduction tube can also be made from less elastic materials such as polyolefins or other flexible polymeric film materials and fabrics provided that the connection with the elastic compression tube is made using a joining band of an elastic material interposed between and bonded to the conduction and compression tubes.

Spacer components can be located within the lumen of the conduction tube distal to the distal end of the penis so as to prevent crimping and kinking of the tube walls, due to folding or bending of said tube, that could result in a blockage of the urine flow. The spacer may be made from various types of materials, for example, loosely knitted nylon or polyolefin fibers, porous wicking materials such as needled felts of rayon or cellulose acetate fiber bundles, or a flexible solid strips or shapes of polyolefins, silicone rubber, selected for the performance desired of the conduction tube. The width, thickness, and material of the spacer are selected to accommodate the expected liquid flow situation. For example, when the walls are pressed together by a crimping bend in the tube, the narrow openings between the edges of the spacer and the tube walls will still accommodate only relatively low volumetric flow rates. In contrast, the relatively open interior region of a mesh spacer (which remains unimpeded by a crimping bend) will accommodate much higher volumetric flows.

A spacer made of a porous wicking material can act as a means to promote the flow of urine from one point to another in the system. A bed of fine, interconnected capillary spaces will spontaneously imbibe ("wick") a fluid that effectively wets the walls of those capillaries. Provided that the wick is on a level plane, it will continue to take up the liquid until all the spaces are filled or until the liquid reservoir is empty. Once filled, the wick will form a "drip" from the lowest point responding to gravitational forces. In addition, as a result of the "capillary wicking" action, a wetting fluid can travel "up" into narrow-diameter capillaries a distance of several centimeters in ascendant flow against the force of gravity. The height of this "capillary rise" is governed by the size and wetting properties of the capillaries and the properties of the liquid. If the as-yet-unwetted upper portion of a liquid-imbibing capillary wick is bent to a horizontal or a downward direction at a point below the maximum capillary rise then the wick will be filled with liquid. If the wick is extended in a downward direction to a point below the level of the liquid reservoir, then descending flow of the liquid, induced by gravity, will empty the reservoir to the level of the wick inlet in a siphoning action. Thus, the wick can provide the necessary fluid "lift" via the capillary wetting function to commence the siphoning action.

The capillary wicking function can also be utilized if the capillary spaces are provided in and on the walls of the conduction tube. Thus, conduction tubing which itself is made from a capillary-containing material such as fabrics, fiber mats, or open cell foams having a waterproof coating on the outer walls can function as both tube and wick, as can conduction tubes made from non-porous film materials whose interior surfaces have been previously coated with materials having the required wicking properties. Thus, a wick or surface that is well-wetted by urine can act as a siphon channel causing the urine to flow from a source initially in an ascending direction (against the influence of gravity) and thence descending to a receptor or conveyance region for transport to storage. Wicking components and components having wettable surfaces can be located on or near to the interior wall of the conduction tube so as to form a continuous wicking and wetting channel along the length of the collection device from the penis-gripping region to the conveyance device. By extending the area having wettable surface properties around the entire interior surface of the tube from the edge of the compression tube to the conveyance device connection, drops of urine forming anywhere within the region will be subject to wicking collection and transport to the conveyance connection.

Wicks from different components or devices when placed in contiguous connection, i.e., they are touching but not necessarily mechanically bonded together, will transfer wicked liquids via formation of a liquid "bridge", effectively forming a continuous wicking flow through the contiguous junction. Thus a series of contiguously connected wicks will form a continuous liquid flow path.

Elastic Compression Tube

In the preferred embodiment, the collection device is fastened onto the penis of a user by means of an elastic compression tube comprised of one or more layers of elastic fabric, elasticized fabric, or elastomer sheet having dimensions such that the material of the tube, when stretched in the radial plane to fit over the penis, is stretched within the elastic limits of said material. For application, the lumen of the elastic compression tube is stretched in more than one dimension until the lumen is enlarged sufficiently to allow a flaccid penis to be placed into the urine collection device without interference from the wall of the elastic tube. When the collection device is dimensionally fitted for an individual user such that the perimeter of the unstressed compression tube is 5 to 20% smaller than that of the individual user's penis, the retracted compression tube will grip the shaft of the penis with uniform compressive pressure within the gripping region, thus provides a unique means for attachment to and sealing to the penis. The male urine collection device has a urine conduction tube that can be any thickness, but in one embodiment here disclosed has thin walls, having a diameter sufficient to surround but not constrict the distal end of a penis and any nearby wicking or spacer components, if present, and ending in a connection to a urine conveyance device. The conduction tube is attached directly to the distal outer wall of the elastic compression tube along a band of sufficient length to ensure adequate mechanical connection and seal against urine leakage between the tubes. The inner surfaces of the elastic compression tube provide the frictional characteristics for gripping the penile skin and the sealant characteristics for providing a urine seal.

The proximal interior surface or portions thereof of the elastic compression tube can be coated with one or more materials to provide an enhanced frictional grip on the adjacent penile skin. Alternatively, one or more strips of elastomeric material, separate from or bound to the interior surface of said compression tube, may be interposed between the compression tube and the penile skin to provide additional frictional grip. When the elastic compression tube is made of a fabric material, the fabric material can be treated with one or more materials to render parts or all of the compression tube urine/water repellent so as to prevent liquid urine from wetting and penetrating the fabric, and thus escaping from the collection device. The weave of the fabric and the spaces between any strips of elastomeric material are such that the tube will allow moisture on the penile skin surfaces that are within the confines of the compression tube to evaporate and for atmospheric gases to contact that skin.

Alternatively, the said fabric material to be used for constructing the elastic compression tube can be substituted with a thin layer of rubbery polymer such as silicone rubber or latex rubber. In this alternate embodiment, all of the objectives sought in this invention will still be accomplished with the exception of the ability to allow vapors to escape the device.

Operation of the Collection Device

In operation, free-flowing urine is directed through the open channel to the conveyance connection. Small volume emissions of urine that are too small to constitute a continuous flow will be absorbed into the wick or will wet the interior wall and spread out until they contact a wicking surface that will then collect and convey them. Drops of urine that may drip from the urethral opening from time to time will be absorbed by the nearby wick or surface-wetting materials and transferred to the conveyance connection.

To put on this device, the cross-sectional area of the compression tube needs be stretched open. This can be accomplished, for an example, by pulling a pair of tube-spreading tools inserted into pockets attached to the exterior surface of the compression tube. The proximal ends of the pockets are in-line with the proximal end of the compression tube. The pockets are open both at the top and the bottom. The pockets can be made to attach to the surface of the compression tube by a variety of suitable means selected based on the specific material of construction for the compression tube. The total width of the two pockets should desirably cover approximately 50% of the perimeter of the compression tube. The height of the pockets can range from 0.75 to 1.50 inches, preferably 1 inch. The tube-spreading tool consists of a pair of rod-shaped instruments connected at one end. The legs of the instrument are bent at approximately 1 to 1.25 inches from the end to form a plane perpendicular to the instrument. The two legs of the said instrument are distanced to each other approximately 1.00 to 1.25 inches. With an inwardly opposing force applied to the outwardly facing sides of the two legs, the distance of the two legs can be reduced to such an extent to allow insertion of the ends of the tube-spreading tool into the pocket of the compression tube. When the opposing force applied to the outwardly facing sides of the two legs removed, the distance between the two legs will increase in a spring-like manner returning to the unstressed condition of being approximately 1.00 to 1.25 inches. If a tube-spreading tool is placed in each pocket of the compression tube, the removal of the opposing force applied to the outwardly facing sides of the two legs will increase the width of the pocket along with the portion of the surface of the compression tube to which the pocket is connected. Using two fingers of one hand holding one of the two tube-spreading tools and two fingers of the other hand holding the other tube-spreading tool, a person can increase the distance between the two tube-spreading tools. Therefore, aided by the tube-spreading tool, a person can easily spread open the cross-sectional area of the compression tube into a shape approximating a square of suitable dimension to allow placing a flaccid penis into the urine collection device. After the penis is completely immersed into the compression tube, the tension exerted by two hands is slowly reduced to allow the compression tube to retract. Subsequently, pressure is reapplied to the two legs of the tube-spreading tool one at a time to remove the tube-spreading tool from the pockets. The tube-spreading tool could be made from a plastic material, a metallic material or any other suitable material pure or composite materials.

In order to facilitate use of the urine collection system, several embodiments are possible that make donning and wearing the urine collector easy and comfortable. In one embodiment, the collection device comprises a tubular sheath whose diameter decreases from the point where the collection device interfaces with the conveyance device to the opening in the collection device that forms the cavity into which the penis is inserted. At the top of the cavity, the sheath contains a longitudinal slit for easy donning, and after it is snugly in place, the slit flaps are fastened with multiple-hook-and-loop closure and the sheath maintains its own position. In another embodiment, in the same slitted fashion, the sheath is easily drawn up to cover the penis and the slits are fastened with a zipper or zip-lock-type closure. In yet another embodiment, a ring of elastic tubing is fixedly attached to the top of a non-slit sheath. Then the sheath is rolled downward around the ring. When the sheath is donned, the ring is rolled upward along the shaft of the penis until the sheath is fully extended. The elastic ring serves to maintain the sheath in position on the penis.

In yet still another embodiment, a rigid plastic expandable bellows ring, in its non-expanded or compressed state, is removably attached to the top of a sheath and is rolled downward within the sheath from the top penis entry point to the bottom of the sheath near the conveyance device. In this embodiment, the user pulls the rolled sheath and enclosed bellows ring to cause said bellows ring to assume its expanded state, and then unrolls the sheath onto the penis by rolling the bellows and sheath roll longitudinally up the shaft of the penis. When the sheath is fully extended, the expanded bellows can be returned to its compressed state, detached from the sheath, and expanded again for removal from the penis. The sheath will remain in place through its inherent elasticity. Similarly, a spring ring which houses a toothed plastic strap, can be removably attached, in its unexpanded state, to the top of a sheath and rolled downward within the sheath. The user pulls the rolled sheath and enclosed spring ring to cause the ring to assume its expanded shape, and then unrolls the sheath onto the penis prior to removal of the ring. In this embodiment, the toothed strap prevents the spring ring from returning to its original size, and the ring is in the expanded state when detached from the sheath. Otherwise, it is used in the same way as the rigid plastic bellows.

Finally, a hand-held jaw ring expander for extending the sheath over the penis is disclosed. This lever-operated device responds to compression of the lever by increasing the diameter of an attached expansion ring. In use, the end of the sheath attached to the conveyance device is inserted into the expansion ring, in its inactivated compressed state, and the penis entry end of the sheath is draped over the ring. Then the device lever is compressed, causing the expansion ring and surrounding sheath end to increase in diameter. Expanded ring and sheath are then moved longitudinally up the shaft of the penis. When the sheath is nearly fully extended, the device lever is released, allowing the ring and expanded sheath to contract. The remaining sheath length is then unrolled onto the penis leaving the sheath self-secured through its own elasticity. The device lever is again compressed, which enlarges the ring and allows it to be removed from the penis.

Conveyance Device

Conveyance Tube

A urine conveyance tube is disclosed that contains, within the tube lumen and throughout its length, one or more materials that are capable of wicking urine. The conveyance tube is fitted with a first connecting end that will provide a secure connection with a urine collection device such as an external catheter and a second connecting end that will provide a secure connection with a urine storage device such as a leg-mounted drainage container.

In a second embodiment, a thin-walled conveyance tube is disclosed that is capable of easily conforming to various contours and shapes, that may be nearly flat in cross-section, and that contains, within the tube lumen and throughout its length, a spacer (a separating element) to prevent the lumen from being completely closed and sealed by kinks or crimps in the tube. The thin-walled conveyance tube is fitted with a first connecting end that will provide a secure connection with a urine collection device such slide independently over one another thus retaining the flexibility of thin films while providing added mechanical protection for the urine-carrying tube elements.

Also in either embodiment, the walls of such conveyance tubes can be fabricated by a variety of manufacturing techniques such as, for example, edge sealing of cut sheets by thermal welding or by adhesive, or by extruding one or more bonded or unbonded layers of suitable polymer materials through a heated die or series of dies to form a continuous length of tubing.

Spacer

In order to prevent complete closure of the thin-wall tube lumen by crimping and kinking actions such as might occur due to extreme bending or folding of the tube, a spacer or separating element having finite thickness and width dimensions is placed within and along the entire length of the tube lumen. For proper operation, a more-or-less separate spacer body, whose movement is essentially separate from and thus not effecting that of the tube wall is required. A protrusion molded into and thus continuously attached to the tube wall will have an adverse limiting effect on the desired flexibility of the wall because of the continuous attachment of the protrusion to the thin-walls. However, any spacer produced by a molding process combined with a cutting or breaking process that produces a protrusion which is only partially attached to the wall and which thus does not deleteriously change the desired flexibility of the wall, is included within the scope and intent of this invention.

The spacer may be made from various types of materials including open mesh (e.g., nylon or polyolefin fibers loosely knitted, etc), a porous wicking material (e.g. rayon acetate needled felts, cellulose acetate fiber bundles, etc,), or a flexible solid (e.g., as an external catheter and a second connecting end that will provide a secure connection with a urine storage device such as a leg-mounted drainage container.

In the second embodiment, the thickness of the film layer used in a thin-walled conveyance tube is in the range 0.0127 to 0.127 mm (0.0005 to 0.005 inch) and preferably in the range of 0.025 to 0.076 mm (0.001 to 0.003 inch), which is thinner by orders of magnitude than that of the rubber or polymeric elastomer tubes used with current urine management system, which are typically in the range of 1.7 to 3.3 mm (0.067 to 0.13-inch). The "flat" property of such flat conveyance tubes can be characterized as having a thickness-to-width ratio (i.e., the ratio of the minor-to-major axes of the ellipse formed by the cross-section of the partially flattened tube) of from less than 1.0 to a low value limited only by the presence of the spacer and the lumen left open to accommodate urine flow, and preferably in the range of 0.05 to 0.5. Such thin-walled, flat conveyance tubes are considerably more flexible than the current thick-wall tube in conforming to fit contours of the human body. Thin-wall tubes may be most conveniently deployed in a "nearly-flattened" form that will "inflate" when free liquid passes through them and then return to the "nearly-flattened" shape when flow subsides.

In either embodiment, the tube walls that contact the urine are made from waterproof materials while other walls, or portions of other walls, may be fabricated from other materials to suit other purposes such as, but not limited to, providing resistance to puncture and tearing, or providing comfort for skin contact surfaces. The conveyance tube may be formed with the tube wall comprising a single layer or a multiplicity of layers of thin films. Multiple layers of thin films that are substantially unbonded can polyolefin film strips, silicone rubber shapes, etc), depending the functionality desired of the conveyance tube in specific applications. The width, thickness, and material of the spacer are selected to accommodate the expected liquid flow situation. For example, when they are pressed together by a crimping bend in the tube, the narrow openings between the edges of the spacer and the tube walls will still accommodate low volumetric flow rates. In contrast, the relatively open interior region of a mesh spacer (which remains unimpeded by a crimping bend) will accommodate much higher volumetric flows.

Wicking Spacer

A spacer made of a porous wicking material can act as a means to promote the flow of urine from one point to another in the system. A bed of fine, interconnected capillary spaces will spontaneously imbibe ("wick") a fluid that effectively wets the walls of those capillaries. Provided that the wick is on a level plane, it will continue to take up the liquid until all the spaces are filled or until the liquid reservoir is empty. Once filled, the wick will form a "drip" from the lowest point responding to gravitational forces. In addition, as a result of the "capillary wicking" action, a wetting fluid can travel "up" into narrow-diameter capillaries a distance of several centimeters in ascendant flow against the force of gravity. The height of this "capillary rise" is governed by the size and wetting properties of the capillaries and the properties of the liquid. If the as-yet-unwetted upper portion of a liquid-imbibing capillary wick is bent to a horizontal or a downward direction at a point below the maximum capillary rise then the wick will be filled with liquid. If the wick is extended in a downward direction to a point below the level of the liquid reservoir, then descending flow of the liquid, induced by gravity, will empty the reservoir to the level of the wick inlet in a siphoning action. Thus, the wick can provide the necessary fluid "lift" via the capillary wetting function to commence the siphoning action.

The capillary wicking function can also be utilized if the capillary spaces are provided in and on the walls of the conduction tube. Thus, conduction tubing which itself is made from a capillary-containing material such as fabrics, fiber mats, or open cell foams having a waterproof coating on the outer walls can function as both tube and wick, as can conduction tubes made from non-porous film materials whose interior surfaces have been previously coated with materials having the required wicking properties. Thus, a wick or surface that is well wetted by urine can act as a siphon channel causing the urine to flow from a source initially in an ascending direction (against the influence of gravity) and thence descending to a receptor or conveyance region for transport to storage. Wicking components and components having wettable surfaces can be located on or near to the interior wall of the conduction tube so as to form a continuous wicking and wetting channel along the length of the collection device from the penis-gripping region to the conveyance device. By extending the area having wettable surface properties around the entire interior surface of the tube from the edge of the compression tube to the conveyance device connection, drops of urine forming anywhere within the region will be subject to wicking collection and transport to the conveyance connection.

Wicks from different components or devices when placed in contiguous connection, i.e., they are touching but not necessarily mechanically bonded together, will transfer wicked liquids via formation of a liquid "bridge", effectively forming a continuous wicking flow through the contiguous junction. Thus a series of contiguously connected wicks will form a continuous liquid flow path.

Wicking Means within Conveyance Tube

A urine-wicking means is placed within and along the entire length of the tube lumen. Said wicking means can be a more-or-less separate wicking body having finite thickness and width dimensions, whose movement is essentially separate from and thus not effecting that of the tube wall. A protrusion molded into and thus continuously attached to the tube wall can be employed, but may have an adverse limiting effect on the desired flexibility of the wall because of the continuous attachment of the protrusion to the wall. However, any wicking body produced by a molding process combined with a cutting or breaking process that produces a protrusion which is only partially attached to the wall and which thus does not deleteriously change the desired flexibility of the wall, is included within the scope and intent of this invention.

A body or layer of a porous wicking material can act as a means to promote the flow of urine from one point to another in the system. A bed of fine, interconnected capillary spaces will spontaneously imbibe ("wick") a fluid that effectively wets the walls of those capillaries. Provided that the wick is on a level plane, it will continue to take up the liquid until all the spaces are filled or until the liquid reservoir is empty. As a result of this "capillary action", a wetting fluid can travel "up" into narrow-diameter capillaries a distance of several centimeters against the force of gravity; the height of this "capillary rise" is governed by the size and wetting properties of the capillaries and the properties of the liquid. If the as-yet unwetted upper portion of a liquid-imbibing capillary wick is bent to a horizontal or a downward direction at a point below the maximum capillary rise, then the wick will fill with liquid. If the wick is extended in a downward direction to point below the level of the liquid reservoir, then descending flow of urine, induced by the influence of gravity, will empty the reservoir to the level of the wick inlet in a siphoning action. The wick provides some fluid "lift" via the capillary wetting function to enable the fluid to reach the point where gravity-induced flow will carry the fluid down the remainder of the wick to the discharge outlet. Flow through such a wicking channel can follow an ascending path.

The wicking function provided through the properties of the spacer can be equally utilized if the capillary spaces are provided in and on the walls of the tube. Thus, flat thin-wall tubing which itself is made from a capillary-containing material such as fabrics, fiber mats, or open cell foams having a waterproof coating on the outer walls can be used as wicks. Additionally, conveyance tubes whose interior surfaces are coated with materials having the required wicking properties can also provide the wicking function.

The two ends of the conveyance tube can be fitted with suitable adapters chosen from a variety of styles, shapes and sizes available from suppliers of fittings and adapters. These ends can also be fitted with short stub lengths of conventional elastomer tubing to enable connection to collection and storage devices.

Storage Device

Storage Container

With respect to the urine storage container, urine conveyed to the storage container is distributed and rapidly converted to a form (solid, gelled-solid, or absorbed in capillary spaces) that no longer has fluid properties. The storage container incorporates a novel liquid distribution and absorption means to ensure that the urine is immobilized quickly, efficiently, and in a predetermined location. This distribution/absorption means also effectively prevents the reverse flow of urine out of the container. The container has a low-profile, and uses thin-film wall structures to provide outer walls and internal compartments that flex and conform to body contours and movements, resulting in comfortable fit to the user both when empty and when filled with immobilized urine. This storage container can be attached to the user's body or clothing by a variety of attachment means. One embodiment of the storage container is intended for disposal together with the contained immobilized urine, and replacement with a fresh, unused container.

The urine storage container is relatively uniform in cross-section, is comprised of at least one compartment for distribution, absorption and subsequent storage of urine, is capable of conforming to various contours and shapes, affords uniform distribution of incoming and absorbed urine, has a unique means for the separation of liquid and absorbed urine which acts to prevent absorbed urine from contaminating the site of collection, and is well-suited for disposal together with the absorbed urine. The urine storage container has a connecting end that will ensure a secure connection with a urine conveyance tube. The urine storage container is suitable for use by ambulatory incontinent humans, for example when attached to the leg or waist or when attached to their clothing at suitable point, and by non-ambulatory humans when attached to a suitable location in their immediate vicinity.

Distribution of Urine in Storage Container

The urine storage container is fitted with a wick that, when wetted with liquid, contains and retains that liquid in relation to the physical nature of the capillary spaces available to the liquid. Capillary distribution coupled with absorptive storage effectively prevents urine from returning to the collection site from any point protected by the capillary wicking mechanism. When there is ample liquid supply and little removal from the wick, then some excess of loosely bound liquid over the capacity of the wick for capillary-bound liquid may accumulate in said wick. When the liquid moves through and is removed from the wick, eventually only that liquid is left that is so tightly bound that it cannot be taken up by the physical or chemical absorption energies of the absorption sites. Such tightly bound liquid cannot be easily removed from the wick by the absorbent materials, nor can it spontaneously flow up the wick and return to the site of collection.

The external and internal walls and supporting structure of the storage container are made from thin films of polymeric materials to provide needed properties such as physical strength and liquid resistance while contributing only minimal weight from the container structure itself. The thickness of the film layers used in the walls is in the range of 0.013 to 0.25 mm (0.0005 to 0.010 inch) and preferably in the range of 0.025 to 0.10 mm (0.001 to 0.004 inch), which is significantly thinner than that of the rubber or polymer wall materials used in current urine storage containers which are typically in the range of 0.17 to 1.0 mm (0.0065 to 0.040-inch) thick.

The storage container may be formed with the tube wall comprising a single layer or a multiplicity of layers of such thin films. Multiple layers of thin films that are substantially unbonded can slide independently over one another thus retaining the flexibility of thin films while providing added mechanical protection for the urine-contacting surfaces. The container walls that contact the urine are made from waterproof materials while other walls may be fabricated from other materials to suit other purposes such as providing resistance to puncture and tearing, or providing comfortable skin contact surfaces.

The wall structures of such storage containers can be fabricated by a variety of manufacturing techniques such as, for example, edge sealing of cut sheets by thermal welding or by adhesive, or by extruding one or more bonded or unbonded layers of suitable polymer materials through a heated die or series of dies to form a continuous length of thin-walled tubes.

The container of subject invention can comprise a single compartment or multiple compartments, connected together with associated distribution channels to convey the urine to the absorbent. Since the solid or gelled materials do not move as freely as liquid urine, distributing the dry absorbing media among multiple compartments in the storage container prior to use can provide a means to enable more uniform distribution of the absorbed urine. The absorbent may be placed in the absorption compartments in the form of a mass of non-woven fibers, or as solid materials held in or on a physical structure such as a woven textile or non-woven mat of fibers, or as absorbent materials coated onto the compartment wall in partially gelled form or by means of suitable attachment means, or as a material suitable for confining liquids by capillary force, or a combination of the above. In addition, the absorbent may be placed in the compartment or compartments in loose form provided that the number and shape of the compartments and the liquid distribution means are such that the liquid will be distributed more or less uniformly to the overall mass of absorbent.

The absorbent is arranged in multiple compartmentalized regions to facilitate uniform and rapid uptake, to ensure more uniform distribution of weight over the entire container, and to impart a unique mechanical flexibility to the container. The multiplicity of compartments enables the individual compartments to fold more easily at the joining edges than in the absorbent bed region. The deliberate use of thin-layer geometry for the absorbent beds enables the absorption process to be completed rapidly so as to hold the wet absorbent in place and to impart some mechanical flexibility to the absorbent bed itself, further enhancing the capability of the container to conform to a variety of surface contours, and to change its shape rapidly as dictated by movement of the user.

Urine Absorbent Materials

A wide range of absorbent materials can be used for the purpose, including but not limited to the following. Hydrophilic polymers, often termed superabsorbent polymers, that swell and form gels with absorbed aqueous solutions are formed from a variety of synthetic polar polymeric materials both alone and chemically combined with natural polymers such as starches. Inorganic compounds react with aqueous liquids to form solid hydrate compounds (silica gel, calcium sulfate, etc). Organic fiber masses, both woven and non-woven, that take up the aqueous liquid through combined chemical and physical forces, include such absorbent solids as cellulose fiber and other natural fiber products. Blinding of unused absorbent particles is common when liquid is added slowly without mixing to a mass of absorbent particles that is piled or pocketed. It is particularly important to take steps to assure that there is adequate surface area to assure rapid and complete liquid absorption in situations where the mass of absorbent will not be stirred or mixed by the force of inflowing liquid, as is the situation with the oftentimes slow and discontinuous flows of urine from incontinent individuals. Some test results from use of various materials follow.

| Material Type | Specific Material | Liquid Absorption - (g liquid/g solid after 5 minutes) |
| --- | --- | --- |
| Gel resin - polyacrylamide | Allied Colloids ™, ALCOSORB AB3C ™ | 20 water |
| Gel resin - polyacrylic acid, Na⁺ salt | Allied Colloids ™, SALSORB CL15 ™ (ALCOSORB G1 ™) | 50 water |
| Gel resin - polyacrylic acid Na⁺ salt on starch | Clarient Sanwet IM-7200 ™ | 36 water |
| Gel resin on paper - resin fine particles in paper fiber matrix | Gelok 3025 ™ | 35 saline (9 g NaCl/L) |
| Needled felt pads | National Nonwovens ™, PRT005F000478 ™, rayon, 7.2 oz/sq yd | 9.0 (= 2.6 g water/ 3 cm³ of felt) |
| Absorbent paper towels | Low cost commercial service towel | 3.7 |
| Absorbent paper towels | High quality/cost consumer roll | 9.3 |
| Gel resin + inorganic absorbent | $CaSO_4 \cdot 1/2H_2O$ + polyacrylic acid, (Na⁺ salt) | When $CaSO_4$ crystals added to swollen gel, gel collapses by ca. 50%, releasing free liquid |

Distribution/Absorption Interaction

The container structure provides means of liquid distribution that combines wicking means with an adjoining unfilled tube or compartment volume which channel can accommodate liquid volumes that are in excess of the momentary capacity of the wicking material. The liquid urine transport and distribution pathway contains a wick throughout its working length. The wick may lie within or in contact with the channel. Urine to be absorbed is conveyed by wicking, either alone or in combination with free fluid flow of urine in the channel adjoining the wick, into the immediate vicinity of unused or partially used absorbent material or even into fluid transfer contact with said absorbent materials which are intended to absorb that increment of liquid.

Transfer of the urine from the wicking material to the absorbent can take place in one of two ways: either by formation of a drop or volume of free liquid urine which leaves the wick due to pressure in the liquid column within the wick (gravitational force), moves some distance independent of the wick, and then subsequently contacts and flows into the absorbent; or by a "bridging" transfer to the absorbent brought about by close physical proximity of the wick to the absorbent. Transfer from a channel resembles the movement of a volume of free liquid urine that moves independent of the wick.

Controlled distribution of the solid materials will provide more uniform weight distribution in the filled container than is attainable with current leg bags. For the same volume of contained liquid, a flat container that conforms to the body surface can provide a more uniform distribution of the weight of collected urine, and thus a lower pressure against the body surface, than current liquid urine leg bags which generally have a rounded contact surface. The container may be provided in a thin, flattened form that expands more or less uniformly away from the fastening wall primarily as it fills with urine. The wearer perceives a lower weight-per-unit-area as less pressure on his or her skin surface. In addition, rapid liquid absorption and product formation minimizes the presence of free liquid, thus calming the sensation of fluid material (liquid or loose gel) moving in the urine container in response to the wearer's motion.

In this invention, the liquid distribution and corresponding adjacent absorbent regions are separated by a thin film barrier wall that has flow-limiting properties. Flow limitation can be accomplished by various means, for example through use of a barrier that is pierced by an array or arrangement of small penetrations, or use of barrier film that is permeable to urine in selected areas. Movement of urine into the absorbent takes place only through these holes or areas. The location and fluid transport characteristics of these penetrations thus will act to limit the urine flow into the absorbent at each point, and thereby to direct a more uniform distribution of the urine into the absorbent than would occur in the absence of the barrier. Any excess liquid urine that begins to accumulate near a penetration, which is in a flow-limited condition, will tend to induce urine movement through the fluid pathway to another penetration region, which can accommodate the flow. Such flow-limited conditions can result from buildup of liquid or gelled material in the immediate vicinity of the hole that will give rise to an increased resistance to the inflow of additional urine. In the absence of such a flow-limiting barrier, contact-transfer of liquid into the absorbent region is initiated near to the liquid distributor inlet followed by virtually unlimited inflow in the same region, which will result in a large excess of liquid and a mass of blinded, partially used absorbent material moving around in the absorber region for a certain period of time.

The barrier flow-limiting action can be accomplished by interposing the barrier as a layer between a distribution channel and the layer of absorbent materials, or by interposing the barrier as a layer wrapped around a distribution channel that is surrounded by absorbent in contiguous portions or a single portion, or by interposing the barrier as a layer wrapped around a mass of absorbent that is surrounded by a distribution channel or network of channels. The same intent to limit and to distribute the urine flow can also be accomplished through the use of barrier films that have selective permeability to the urine in some or all regions in place of some or all of the arrayed penetrations. Likewise, use of a wicking medium having a surface condition that tends to limit the penetration by the absorbent materials, whether dry or wetted with liquid, into the interior of the wicking medium will also accomplish the same limiting and distribution function. Likewise, use of an absorbent or liquid-imbibing material having a surface condition that tends to limit the penetration of liquids to be absorbed or imbibed into the interior of the absorbent or imbibing material will also accomplish the same limiting and distribution function.

The fine hole size in or the permeability characteristics of the barrier will deter the gelled urine, which is much more resistant to flow through small holes than liquid urine, from flowing back into the distribution ducts even when pressure is applied to the compartment containing the gelled urine. The number of holes and their spacing is computed for each application based on expected flow patterns in the liquid distribution system. On average, expected flow is in the range of 0.02 to 3 mL/sec, with a total volume from each incident in the range of 3–30 mL. These ranges are computed from typical incontinence properties as follows. A completely incontinent person has a relatively constant urine flow rate—usually 1–3 mL/min with some periodic swings from recent intake of fluids or food—set by kidney performance and some slight storage capability in his/her unsealable bladder and the urethral passage. A stress-incontinent person with a moderately full bladder delivers a relatively small volume (10–30 mL) at a high rate (3–5 mL/sec) for a few seconds before she/he can shut it off. An urge incontinent person, one who is unable to retain the urine until a toilet can be reached after the urge to urinate is felt, has a high volume (e.g. 625 mL) and a high flowrate (e.g. 25 mL/sec on average). In summary, the following flow rates can be expected as boundaries upon which to base the design of the barrier hole sizes and spacings:

a) 1–3 mL/min every minute (actual rate=0.02 mL/sec) for the completely continent person, b) 30 mL during 10 seconds every 10–15 minutes (actual rate=3 mL/sec) for the stress incontinent person, and c) 300–400 mL during 1 minute every 120–180 minutes (actual rate=5 mL/sec) for the urge incontinent person.

All three cases result in urine collection of about 60–180 mL per hour, which varies over the day.

Thus, by knowledgeable selection of the type and dimensions of a barrier films or barrier surfaces having known liquid flow controlling characteristics for use as the flow-limiting means, the flow rate of urine into any region of absorbent can be deliberately limited to the rate at which the urine can be effectively absorbed so as to avoid the presence of any substantial excess of free liquid in the absorbent region during the absorption process. Likewise, the gelled urine cannot easily travel into and through the capillary spaces of the wicking material used in the liquid distribution system. Since the transfer of the urine from a distribution wick into the absorbent is a spontaneous process that is driven by lower water activity in the absorbent, the urine that has been absorbed cannot retrace the absorption path to reappear in the distributor. Thus, the distribution barrier will act as a barrier to return of the urine that has passed into the absorption region.

Utility of Storage Container Operation

The storage container, provided in a thin, flattened form that expands in thickness as it fills with urine, can be worn attached to the user's body, e.g., worn on or around a leg, or attached to clothing. The storage container can be mounted or held in place in a number of ways, including but not limited to, elastic bands, woven elastomeric fabric bands, hook and loop attachment, adhesive dots or bands, or in the pouch or pocket of apparel.

If the storage container is not intended for reuse, then it, together with the physically stabilized urine, can be disposed of as a unit without need for removing stored urine. Alternatively, the container can be equipped with an opening through which the stored urine in solid or semi-solid form can be removed for disposal, possibly in a separate bladder insert for that purpose. Following removal of the urine, the container can be disposed of separately, or it can be cleaned and resupplied with urine absorbent for reuse.

Co-disposal of both container and urine eliminates the need for a drain outlet or opening. Absence of such an opening assures that no unexpected leakage can come from that point. Use of a disposable container also eliminates the necessity of emptying and cleaning the used one after each usage in order to ensure cleanliness and freedom from residual urine odor. If desirable, each fresh container can be provided in an internally sterile condition or pretreated with substances for bacterial or odor control.

The inlet opening of the flat thin-walled storage container can be fitted with suitable adapters chosen from a variety of styles, shapes and sizes available from suppliers of fittings and adapters. These ends can also be fitted with short stub lengths of conventional elastomer tubing to enable connection to current devices for collection, conveyance, and storage of urine.

BRIEF DESCRIPTION OF THE SEVERAL VIEWS OF THE DRAWING

FIGS. 2A, 2B, and 2C illustrate perspective and diagrammatic views of the serially-connected male collection device, conveyance tube, and storage container;

FIG. 12 illustrates a first alternate embodiment of the sheath collection device with slitted application and hook-and-loop fastening;

DETAILED DESCRIPTION OF THE INVENTION

Figure 1:
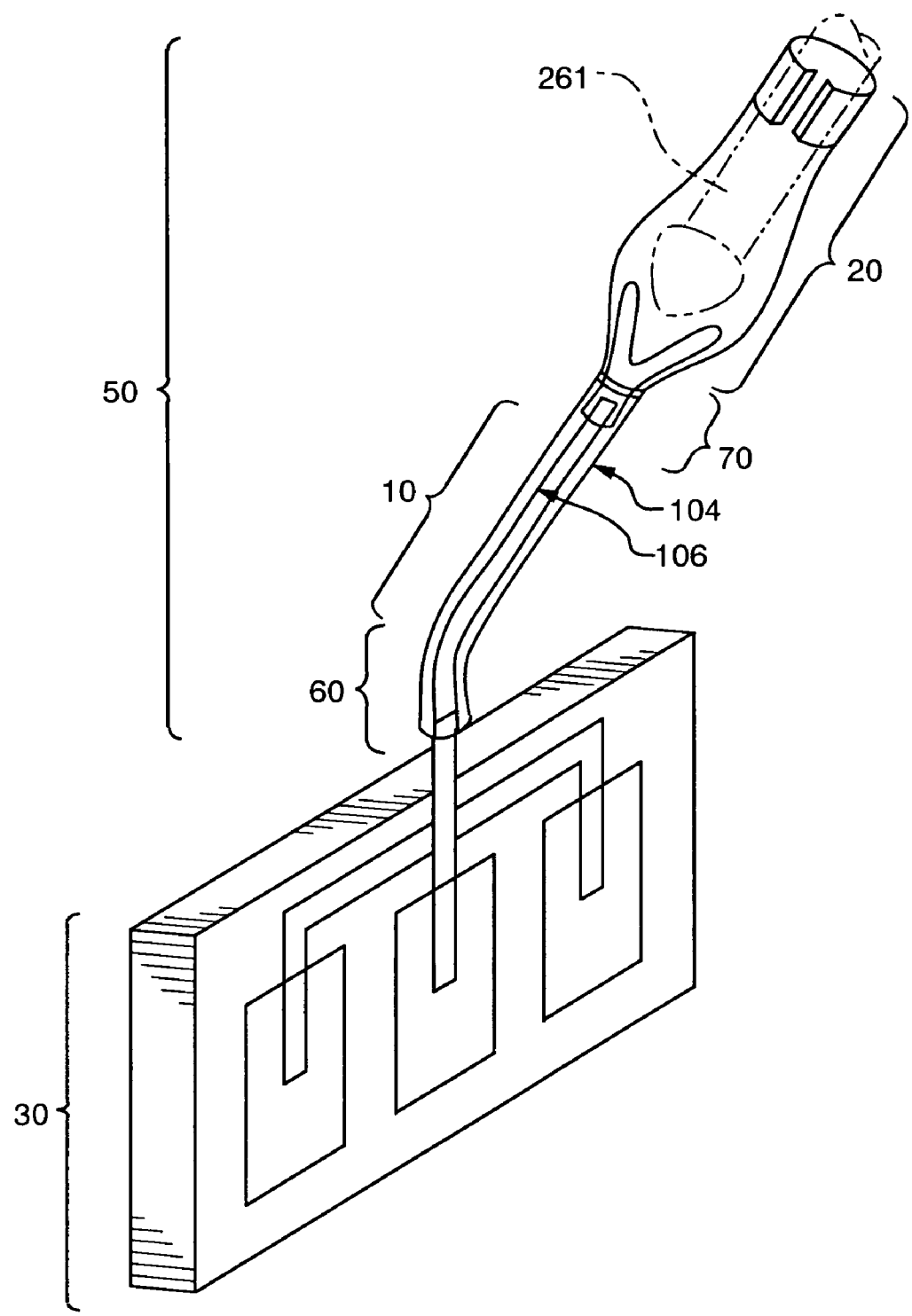
FIG. 1 is a semi-transparent, diagrammatic view of the major parts of the invention.
Figure 2C:
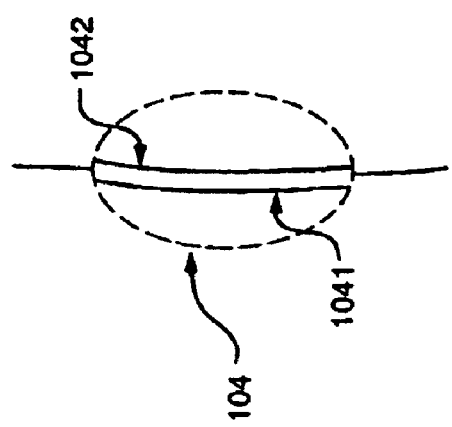

Referring to FIGS. 1, 2A and 2B, novel urine management system 50 comprises novel urine collection device 20 for human males that collects and transfers urine from penis 261 to a novel urine conveyance tube 10 that then conveys urine to a novel urine storage device 30 wherein urine is converted to and stored in immobilized form prior to disposal. All three components of urine management system 50 are serially connected as in FIGS. 1, 2A and 2B, i.e. urine collection device 20 is connected to urine conveyance tube 10 through second wicking interconnection 70, and urine conveyance tube 10 is connected to urine storage device 30 through first wicking interconnection 60.

In simplest form, connection of these novel components as urine management system 50 provides continuous collection of liquid urine from incontinence leakage into novel urine collection device 20, conveyance of that urine through novel urine conveyance tube 10 flowing under gravitational influence, and absorption and storage of the urine in immobilized form in novel urine storage device 30. When urine storage device 30 has become sufficiently filled with urine, it is replaced with a fresh unfilled storage device, and urine storage device 30 containing urine is disposed of as solid sanitary waste.

Incorporation of novel wicking spacer element 260, conveyance tube wicking spacer 106, and second wicking spacer continuous connection 340 within the aforementioned novel devices for collection, conveyance and storage of urine, in combination with wettable interior surfaces on wall of conduction tube 250 and tube film layer 104, and first and second wicking interconnections 60 and 70 between urine conveyance tube 10, urine collection device 20, and urine storage device 30, enable the creation of a novel continuous path for the wicking transport of urine within urine management system 50. Thus, in the preferred embodiment for ambulatory human males, and referring to FIGS. 1 and 10A–D, urine collection device 20 is removably affixed to urine conveyance tube 10 within second wicking interconnection 70 by means of the combination of collector-conveyance connector 290, and conveyance-collector connector 11. Urine conveyance tube 10 is connected to urine storage device 30 within first wicking interconnection 60 through the combination of conveyance-storage connector 12, and storage-conveyance connector 41. Urine collection device 20 contains wicking spacer element 260, urine conveyance tube 10 contains conveyance tube spacer wicking spacer 106, and urine storage device 30 contains second wicking spacer continuous connection 340. A first wicking spacer continuous connection 23 and a second wicking spacer continuous connection 340 provide contiguous wicking connections between collector wicking spacer element 260, conveyance tube wicking spacer 106, and second wicking spacer continuous connection 340. First wicking spacer continuous connection 23 and second wicking spacer continuous connection 340 also may be physical extensions of wicking spacer element 260 and second wicking spacer continuous connection 340.

Figure 11A:
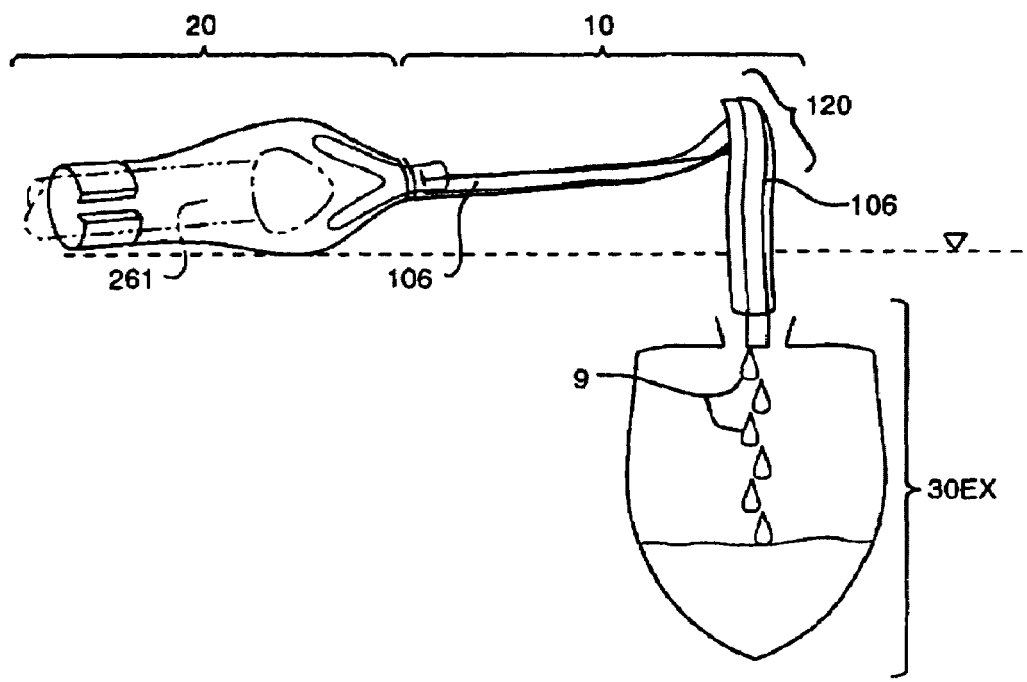
FIGS. 11A, 11B, and 11C illustrate the application of novel wicking flow system for enabling ascendant flow of urine over a high point in a gravity-driven flow path, for enabling flow of urine to a storage point that is at a higher location than the urine collection location, and for enabling removal of pools and drops of liquid urine from within the interior regions of a novel urine collection device for human males and novel urine conveyance tube.
Figure 11B:
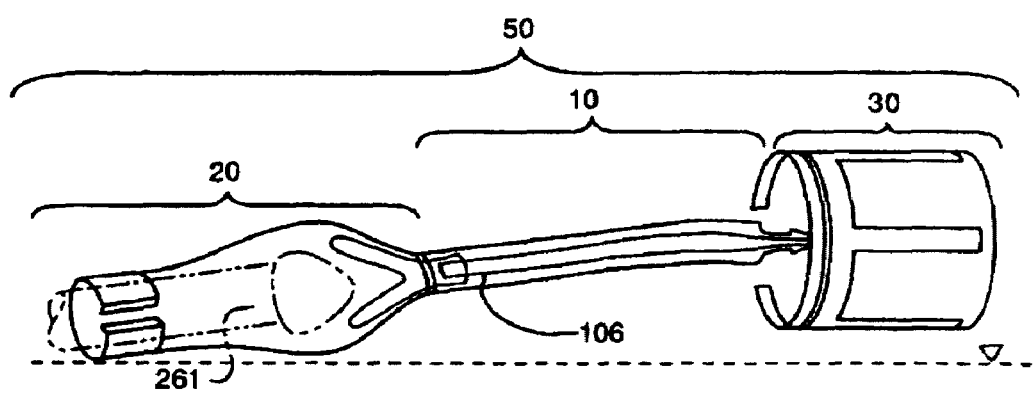
Figure 11C:
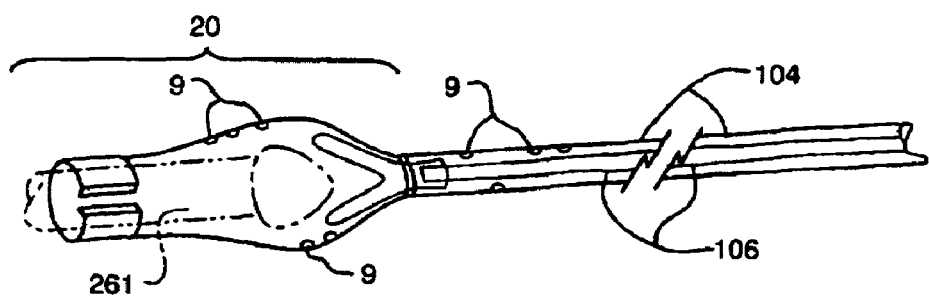

Referring now to FIGS. 11A–C, a continuous wicking path facilitates siphoning drainage over high point 120 as shown in FIG. 11A, enables storage of urine in urine storage device 30 that are higher than urine collection device 20 as shown in FIG. 11B, and, as shown in FIG. 11C, collects and removes to storage isolated residual pools and drops of liquid urine 9 that might otherwise remain in urine collection device 20 or in urine conveyance tube 10, and cause irritation and injury to the skin of penis 261 from the moisture and decomposition products of the urine.

It is also within the description of novel urine management system 50 that urine collection device 20, urine conveyance tube 10, and urine storage device 30 may be constructed and assembled as contiguous units or subassemblies comprising a plurality of novel devices in contiguous position within one or more continuous shells that provide the urine impervious barrier, and additionally may be constructed and assembled as a single, continuous unit wherein urine collection device 20, urine conveyance tube 10, and urine storage device 30 are in contiguous position within a continuous shell that provides the urine impervious barrier.

Additionally, urine collection device 20, urine conveyance tube 10, or urine storage device 30 also can be used to perform the functions of urine collection, conveyance or storage, in combination with one or more of the existent devices for collecting urine (e.g., condom catheters), conveying urine (e.g. rubber tubing), and storing urine (e.g., leg bags), none of which are equipped with means for the novel wicking transport of the instant invention. Connection of urine collection device 20, urine conveyance tube 10, and urine storage device 30 for such independent use can only be accomplished by replacing or supplementing connecting devices used in first wicking interconnection 60 and second wicking interconnection 70 with special connecting devices that are constructed to connect with aforementioned existent devices so as to avoid interference from or confounding of drainage action by the wicking or separating structures within urine collection device 20, urine conveyance tube 10, and urine storage device 30. It should also be clear that addition of wicking materials to such existent other devices for collecting, conveying, and storing urine, none of which are currently equipped for the novel wicking transport, will result in conversion of such devices to fall within the description of the novel devices for collection, conveyance and storage of urine of the instant invention.

Urine Collection

Figure 7B:
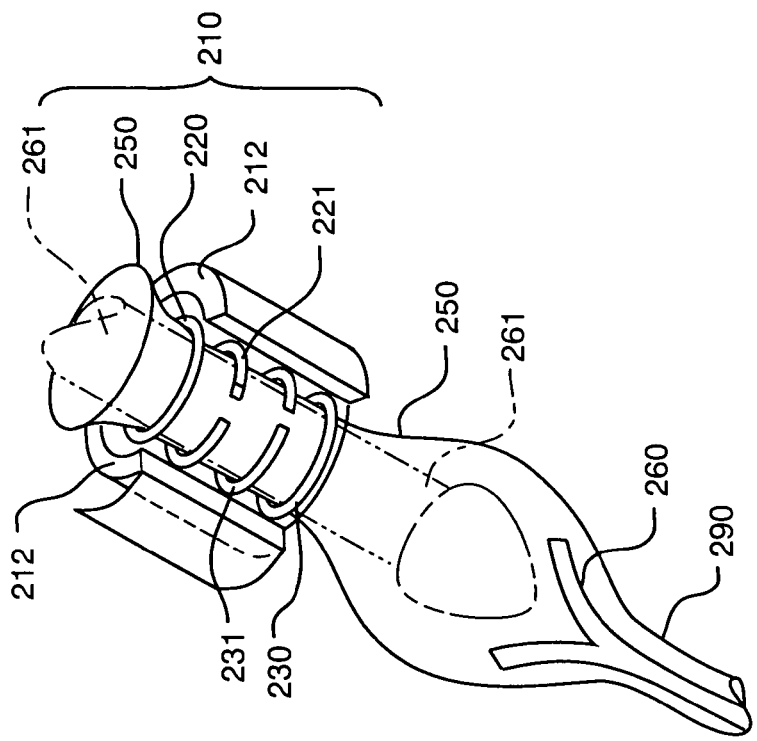
FIGS. 7A and 7B are cross-sectional views of two embodiments of the male collection device.
Figure 7A:
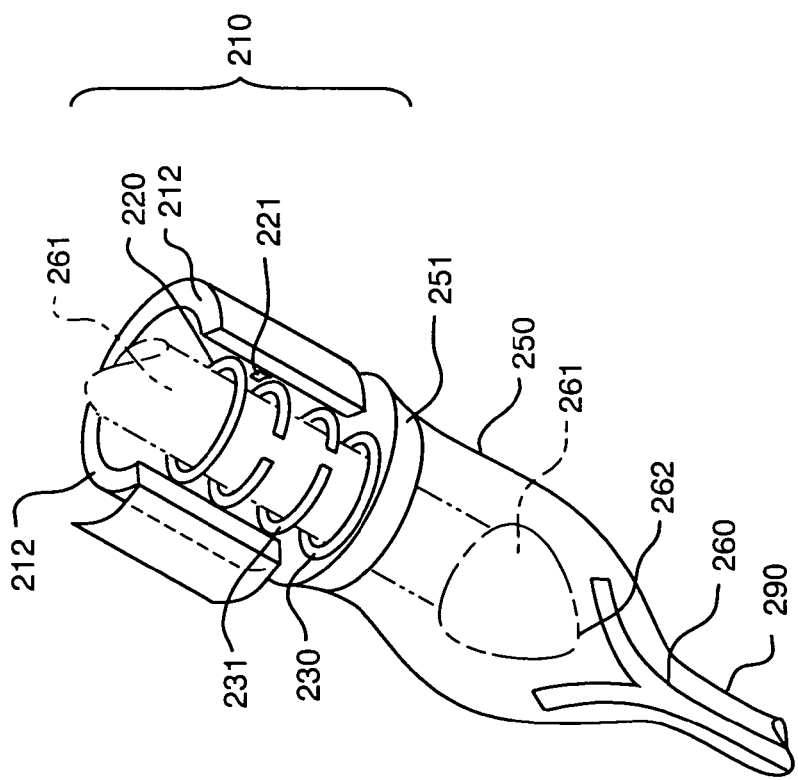

Referring now to FIGS. 7A–B, urine collection device 20 comprises a thin-wall conduction tube 250 of diameter sufficient to surround but not constrict penis tip 262 as well as any spacer or wicking spacer element 260, and compression tube 210, which can be attached to conduction tube 250, as illustrated in FIG. 7A, or can overlie conduction tube 250, as illustrated in FIG. 7B. Conduction tube 250 has collector-conveyance connector 290 at its distal end for connection to a urine conveyance tube. Conduction tube 250 may also contain spacer or wicking spacer element 260.

In the "attached" embodiment shown in FIG. 7A, compression tube 210 is sized to provide an area of radial compression contact on the penis shaft that is sufficient to minimize the slippage of compression tube 210 from its location on the penis 261, and to seal against leakage of liquid urine between the penis skin and compression tube 210. In the "underlying" embodiment shown in FIG. 7B, compression tube 210 is sized to minimize the analogous movement of or leakage past conduction tube 250.

Conduction tube 250 can be made from a rubbery polymer such as silicone rubber or latex rubber, from polyolefin or other flexible film materials, or from fabrics, including elastic and elasticized fabrics, that can be coated or treated if needed to minimize movement of compression tube 210 on the penis skin and the leakage of liquid or vapors. The wall thickness is selected to provide the physical flexibility and conformability to facilitate liquid sealing and frictional stability on the skin surface.

Compression tube 210 may be made of one or more layers of woven elastomeric fabric material, non-woven elastic fabric, elastic fiber-containing fabric, or elastomeric sheeting made from latex or silicone rubber. If a fabric material is used, appropriate areas of fabric can be treated with water-repellant materials such as silicone oils to render that part of the fabric structure water- and urine-repellent to prevent liquid urine from penetrating the fabric, or can be coated with a waterproof, elastomeric coating that will act as a barrier to liquid and vapors. When a fabric material is used to form compression tube 210, uncoated surface areas and open channels within the fabric weave will allow evaporation of water vapor from and penetration of atmospheric oxygen to skin surfaces that lie under the fabric.

In the "attached" embodiment, illustrated in FIG. 7A, conduction tube 250 is connected to compression tube 210 via mutual connection to collection device interface 251, these connections being made while compression tube 210 is in a radially-stretched condition in order to ensure a leak-free connection when compression tube 210 is in its stretched mode on a penis. Collection device interface 251 may be an independent piece or may be a part of conduction tube 250 or compression tube 210. Connection to collection device interface 251 can be made by joining methods suitable for materials that change dimension during use, such as bonding with elastomeric adhesives, or other techniques known to those skilled in the art.

If desired, portions of the skin contact surface of compression tube 210 can be coated with a material, such as a latex rubber, that will provide enhanced frictional ("antislip") characteristics against the skin surface of penis 261. FIG. 7A shows a ring 220 of frictional material coating on the inner surface of compression tube 210. Instead of applying ring 220 as a coating, one or more thin sheets of a frictional elastomeric material such as latex rubber, in the form of rings, strips, or other shapes, can be interposed between compression tube 210 and the skin of penis 261 to provide the desired frictional characteristics. These pieces of elastomeric sheet can be separate from or attached to compression tube 210. Such coatings or strips may appear as complete rings 220 around the internal circumference of compression tube 210 or as independent areas of materials at anti-slip material application locations 221.

Similarly, as a means to provide an enhanced liquid-sealing barrier against the skin of penis 261, portions of compression tube 210 can be coated with a material, such as a silicone rubber of low durometer or a foamed polymer having elastomeric properties, at liquid-sealing material application point 230, which is distal to anti-slip material application locations 221 of the anti-slip materials Alternatively, one or more strips of a sheet of a sealing material such as a silicone rubber of low durometer or a foamed polymer having elastomeric properties can be interposed between compression tube 210 and the skin of penis 261 at liquid-sealing material application point 230 to provide an enhanced liquid sealing capability. These separate strips of elastomeric sheet or foam can be separate from or attached to compression tube 210. Such coatings or strips may be applied as complete rings around the internal circumference of compression tube 210 or as independent areas of materials at additional liquid-sealing material application points 231.

As a further option or as an additional aid for providing liquid sealing capability, a layer of an appropriate urine resistant cream or jelly product may be coated onto the skin surface of penis 261 so as to form one or more circumferential rings around the penis shaft in the region where compression tube 210 will be applied, and distal to the anti-slip material application locations 221 of the frictional materials, thus forming one or more barriers to urine leakage along the skin surface in liquid-sealing material application point 230 and additional liquid-sealing material application points 231.

In the "underlying" embodiment, illustrated in FIG. 7B, conduction tube 250 is extended proximally along the shaft of penis 261 a distance sufficient such that compression tube 210 is completely underlain by a portion of conduction tube 250. Compression tube 210 is located at a position on penis 261 so as to provide compression onto conduction tube 250 and thence onto the underlying portion of penis 261 to enable frictional holding ("antislip") and leakage prevention actions analogous to those provided in the "attached" embodiment, which is described above, to be accomplished through conduction tubing 250. The materials used in conduction tube 250 may provide frictional and leak prevention characteristics.

If desired, portions of either or both of the surfaces of conduction tube 250 can be coated with a material, such as a latex rubber, that will provide enhanced frictional ("anti-slip") characteristics against the skin surface of penis 261 or against the inner surface of compression tube 210. FIG. 7B shows frictional material coated as a ring 220 and as separate anti-slip material application locations 221 on the surface of conduction tube 250. Instead of applying frictional material as a coating, one or more thin sheets of a frictional elastomeric material such as latex rubber, in the form of rings, strips, or other shapes, can be interposed between conduction tube 250 and the skin of penis 261 or between conduction tube 250 and compression tube 210 to provide the desired frictional characteristics. These pieces of elastomeric sheet can be separate from or attached to conduction tube 250.

Similarly, portions of either or both of the surfaces of conduction tube 250 can be coated with a material, such as a silicone rubber of low durometer, that will provide enhanced liquid-sealing barrier against the skin of penis 261 or against the inner surface of compression tube 210. FIG. 7B shows conduction tube 250 coated with liquid-sealing material as a ring at liquid-sealing material application point 230 and as separate spots at additional liquid-sealing material application points 231, liquid-sealing material application points 230 and additional liquid-sealing material application points 231 being distal to anti-slip material application locations 221 of the frictional materials.

Instead of applying liquid-sealing material as a coating, one or more thin sheets of a liquid-sealing elastomeric material such as a silicone rubber of low durometer or a foamed polymer having elastomeric properties, in the form of rings, strips, or other shapes, can be interposed between conduction tube 250 and the skin of penis 261, or between conduction tube 250 and the inner surface of compression tube 210 to provide the desired liquid-sealing characteristics at liquid-sealing material application point 230 and additional liquid-sealing material application points 231. These pieces of elastomeric sheet can be separate from or attached to conduction tube 250. FIG. 7B shows liquid-sealing sheet materials applied as a ring at liquid-sealing material application point 230 and as separate pieces at additional liquid-sealing material application points 231 on the surface of conduction tube 250.

As a further option or as an additional aid for providing liquid sealing capability, a layer of a urine resistant cream or jelly product, which is also compatible with the materials used in conduction tube 250, may be coated onto the skin surface of penis 261 so as to form one or more circumferential rings around the penis shaft in the region where compression will be applied, and distal to the anti-slip material application locations 221 of the frictional materials, thus forming one or more barriers to urine leakage along the skin surface at liquid-sealing material application point 230 and at additional liquid-sealing material application points 231.

Referring now to FIGS. 7A–B, 8A–E, and 9, in order to fit compression tube 210 over penis 261, especially when penis 261 is in the flaccid state, it is necessary to enlarge the area of the lumen of elastic compression tube 210 sufficiently so that penis 261 can be inserted into conduction tube 250 or so that conduction tube 250 may be pulled over penis 261. Enlargement action is required both for the attached embodiment illustrated in FIG. 7A and for the overlying embodiment illustrated in FIG. 7B. Enlargement action can be accomplished by applying outward tension forces to open compression tube 210 at the end that is intended for insertion of the penis.

Referring now to FIGS. 8A–E and 9, which illustrate the actions of compression tube 210 and the tube-spreading tools 280 used therewith, the direction of movement of parts and components is indicated by small arrows enclosed within parenthetical marks (→). In the attached embodiment, compression tube 210 is attached to conduction tube 250 and tensioning points 214, located around the circumference of compression tube 210, are formed when legs 281 of compression tube-spreading tool 280 are inserted into pockets or loops 212, which are located on the perimeter of compression tube 210. Legs 281 of tube-spreading tool 280 are in compressed span 282. The length of legs 281 is selected to be sufficient to enlarge the entire length of compression tube 210 so as to enable positioning of compression tube 210 on penis 261.

Figure 9:
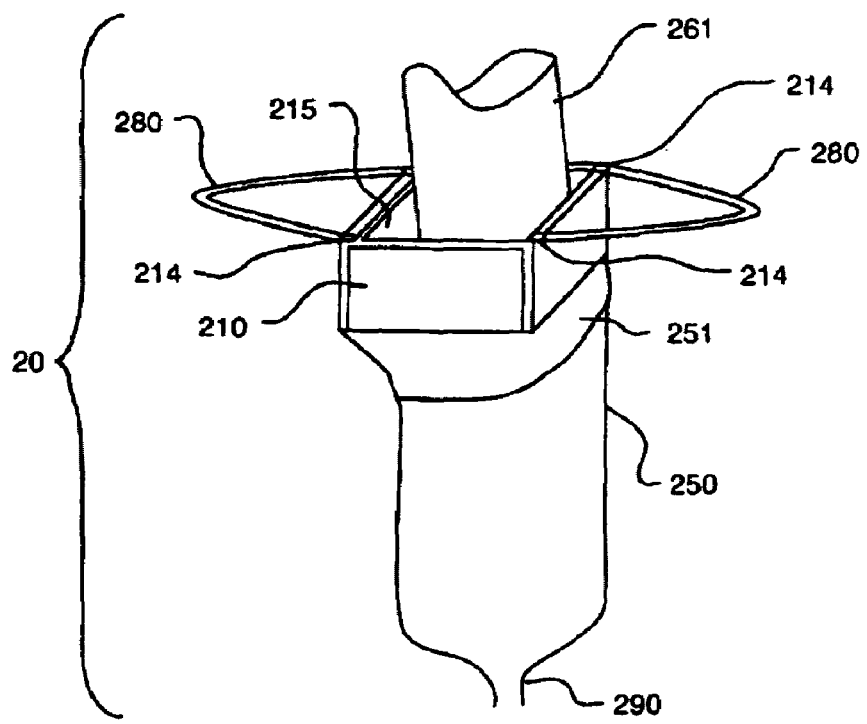
FIG. 9 is a perspective view of the male collection device in expanded state for insertion of penis.

Pockets or loops 212 are located along the circumference of compression tube 210 such that after insertion of legs 281 of two tube-spreading tools 280 into tensioning points 214 on opposite sides of compression tube 210, compressed span 282 between legs 281 to enlarged span 283 together with the act of pulling tube-spreading tools 280 away from each another will cause tensioning points 214 to become the corners of rectangular area 215. Tensioning forces are applied to an extent necessary to increase the dimensional size of rectangular area 215 formed by legs 281 so as to allow insertion of penis 261, as illustrated in FIG. 9.

In the case of use of three tensioning points comprising three equidistant pockets or one long pocket and one short pocket, the two-tipped tube-spreading tool is inserted into two of the equidistant pockets or the single long one, and a single tipped tool is inserted into the other empty pocket. The spreading actions will result in the tube lumen assuming a triangular shape.

Figure 8A:
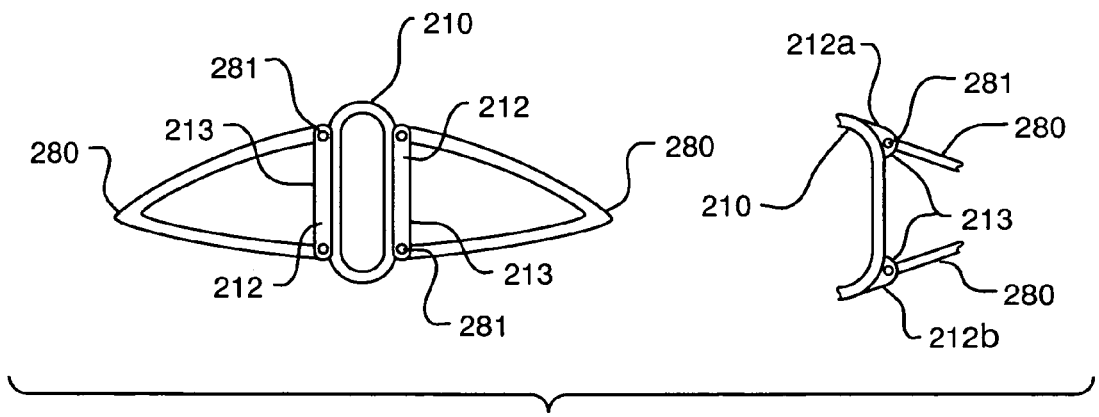
FIGS. 8A, 8B 8C, 8D, 8E, and 8F are views of embodiments of the male compression tube spreading tool and use of said tool.

Referring to FIG. 8A, pockets or loops 212 may be in the form of pockets having one or more openings into a chamber, or in the form of loops of fabric or fiber into which the tool tips are inserted. Legs 281 may be inserted into a long pockets or loops 212 or into adjacent first small pocket or loop 212A and second small pocket or loop 212B formed on the circumference of compression tube 210. Pockets or loops 212, or first small pocket or loop 212A and second small pocket or loop 212B, are formed by attachment of two or more walls 213 of flexible material(s), narrow strips of flexible materials, or one or more fibers of flexible materials onto the outside or the inside walls of compression tube 210. The position and depth of pockets or loops 212 is sufficient to cause the entire length of compression tube 210 to be expanded when a spreading tool leg 281 used is long enough to fill the depth of pockets or loops 212. FIG. 8A shows a top view of the preferred embodiment equipped with two spreading pockets or loops 212 on compression tube 210 having tube-spreading tools 280 inserted in compressed state, and also shows a partial top view of the same embodiment equipped with first small pocket or loop 212A and second small pocket or loop 212B.

Figure 8B:
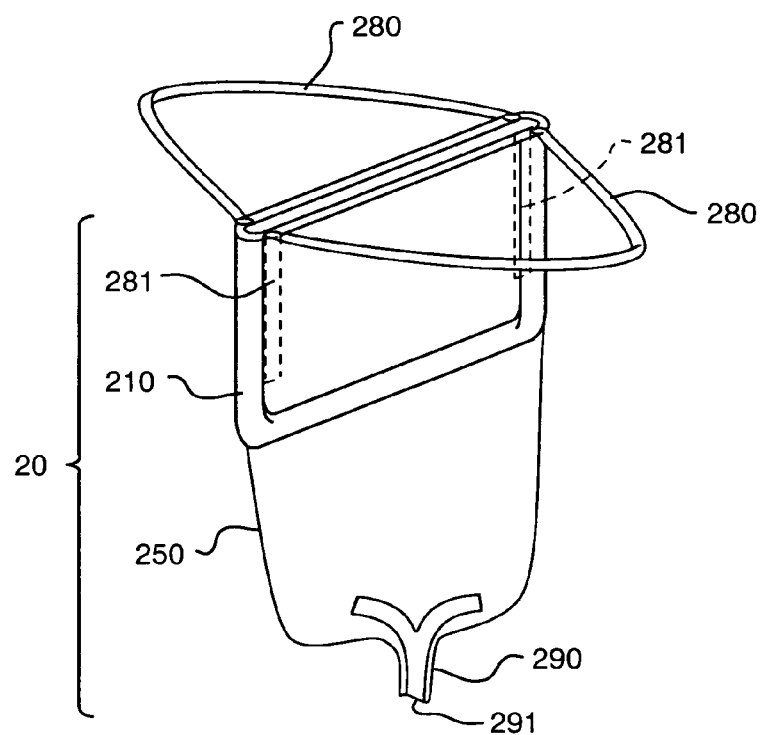

FIG. 8B shows a perspective view of urine collection device 20 that illustrates the action of tube-spreading tools 280, wherein two tube-spreading tools 280 in the form of spring-material spreaders in compressed span 282, are inserted into pockets or loops 212 and then allowed to revert to enlarged span 283 thereby resulting in the stretching of the lumen of compression tube 210 in one dimension. In FIG. 8B, collector-conveyance connector 290 is shown with conduction tube interface 291.

Figure 8C:
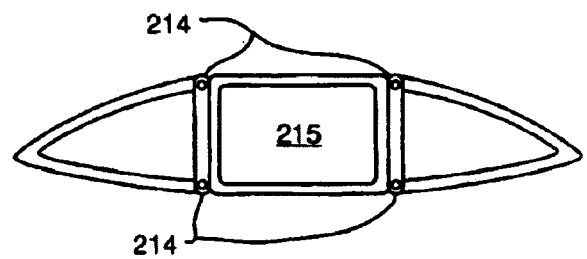

As illustrated in FIG. 8C, two tube-spreading tools 280 are then pulled away from one another to form a rectangular opening with tensioning points 214 at the corners.

Figure 8D:
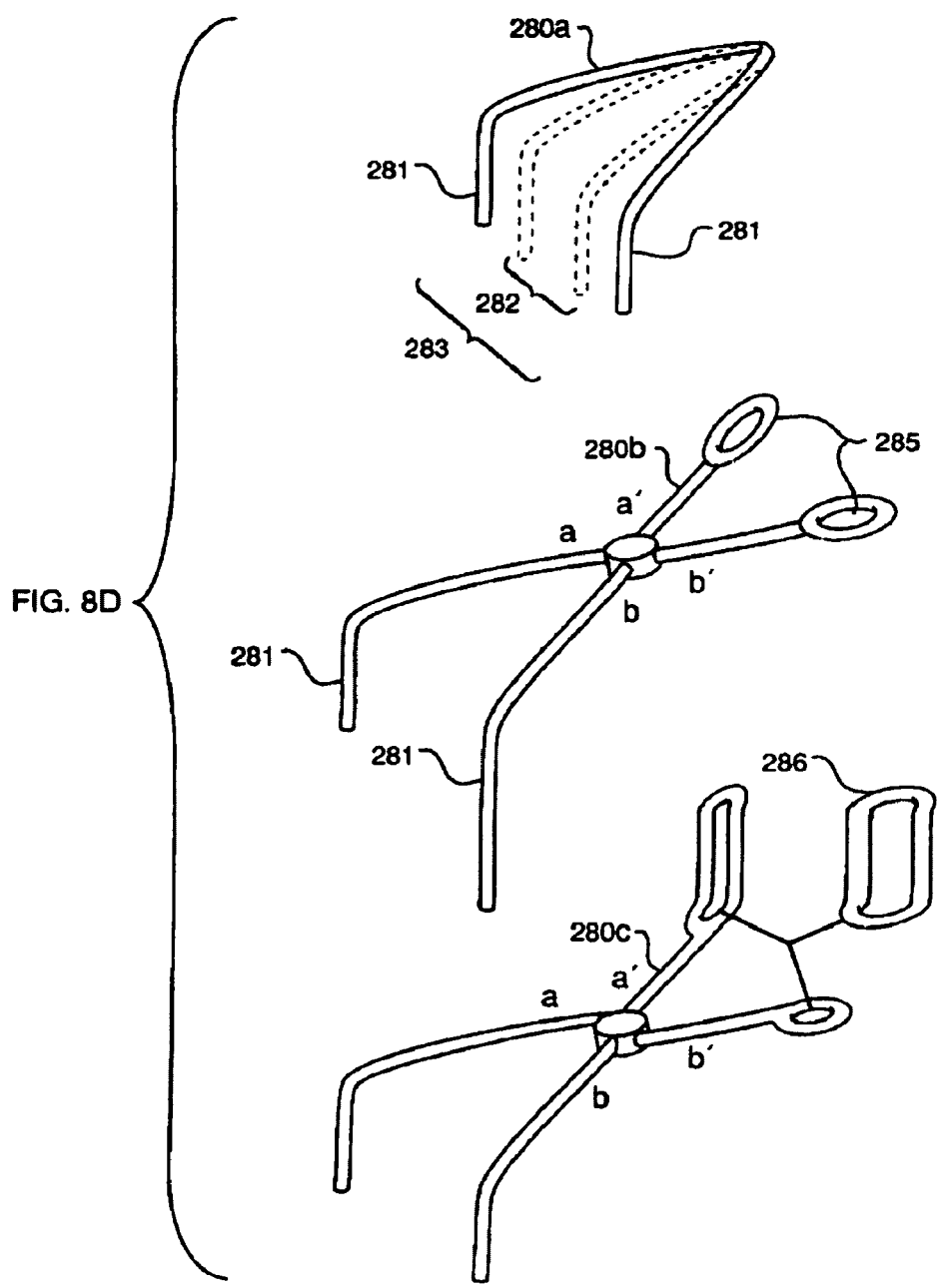
Figure 8E:
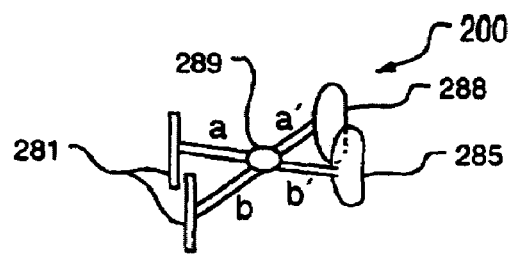
Figure 8F:
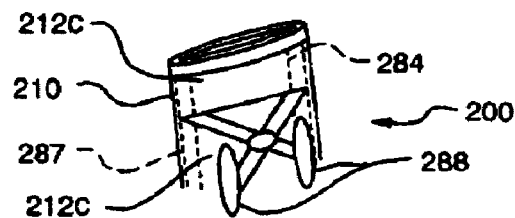

It should be understood that various means for providing expansion forces for tube-spreading tools 280, such as are illustrated in FIGS. 8D and 8E, may be used, including but not limited to: spring-material spreaders 280A; expansion pincers 280B in which at least one of the arms (aa' and bb') that connect the handles to legs is not linear and in which compression of the handles 285 causes the legs 281 to move away from rather than towards each other, and devices such as tensile translation device 280C that translate tensile forces on pull point 286 to lateral spreading movement in legs 281, as well as other such devices familiar to those knowledgeable in the art.

Tube-spreading tool 200, when made in shapes and of materials that are sufficiently small and lightweight, may be incorporated or inserted as a component into the overall structure of the compression tube itself, and allowed to remain more or less permanently in place after incorporation or insertion, thus avoiding the need for finding, inserting and removing special tools each time the compression tube 210 is to be expanded. One embodiment of tube-spreading tool 200 is illustrated in FIG. 8E, in which small expansion pincers 289 have finger tabs 288 and lower tips 287 and upper tips 284 that point in both directions. Tube-spreading tool 200 is used in conjunction with a alternate embodiment pocket 212C comprised of two or more pockets or loops, one located a small distance above the other, and having the openings for tool insertion facing each other. Two such sets of pockets or loops, are located on opposite sides of compression tube 210. Lower tips and upper tips 284 of tube-spreading tool 200 are incorporated into the overall compression tube 210 structure during manufacture or are inserted into alternate embodiment pockets 212C prior to use. Tube-spreading tool 200 is held in place in alternate embodiment pockets 212C by lower tips 287. Squeezing two pairs of finger tabs 288 together between thumb and finger of two hands will provide a lateral movement of lower tips 287 stretching compression tube 210 in one dimension, while pulling pairs of squeezed finger tabs 288 apart will provide a longitudinal stretching of compression tube 210.

Once compression tube 210 has been expanded to dimensions adequate for admission of penis 261, penis 261 is positioned within lumen opening to provide adequate holding and sealing actions, as illustrated in FIG. 9, and the expansion forces enlarging the lumen are released at a rate such that unpleasant sensations and/or injury to penis 261 from contraction of compression tube 210 do not occur.

The key actions of this aspect of the instant invention are: (1) the temporary enlargement of the opening of compression tube 210 by mechanical stretching so as to allow passage of a penis 261 into the lumen of expanded compression tube 210, and (2) subsequent release of the expansion forces so as to allow compression tube 210 to radially compress penis 261. Such stretching can be accomplished by many types of mechanical devices familiar to those skilled in the art and the examples cited are not meant to limit the means used.

Figure 13A:
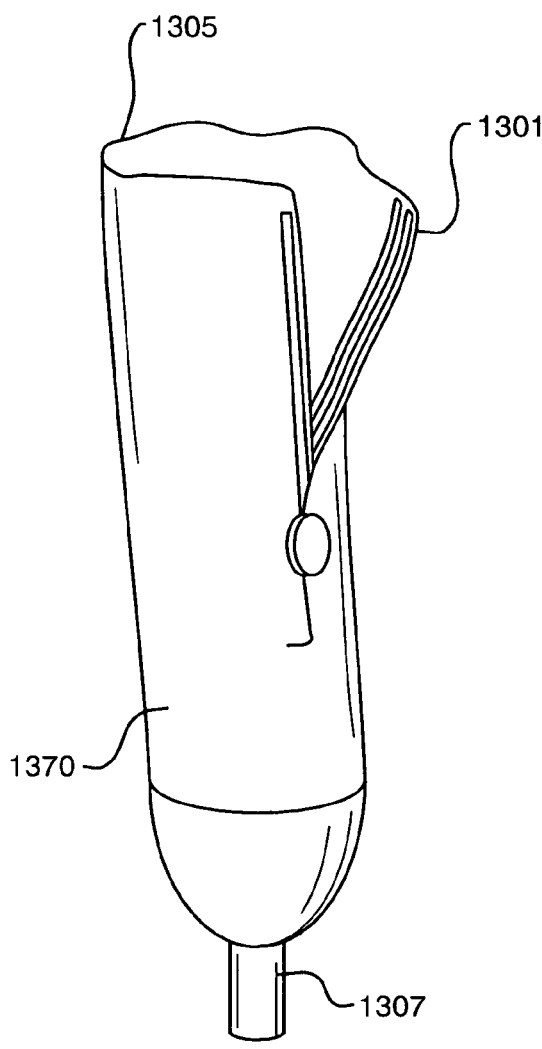
FIG. 13 illustrates a second alternate embodiment of the sheath collection device with slitted application and zip-lock-type fastening.
Figure 13B:

Referring now to FIG. 12, tubular sheath 1220 is shown fully extended with cavity 1207 ready to accept the penis for urine collection, and tubular sheath connection 1209 ready to receive collected urine. Tubular sheath 1220 is open at slit 1203, which is disposed with multiple hook-and-loop fasteners 1201. When tubular sheath 1220 is in place on the penis, hook-and-loop fasteners 1201 are used to close slit 1203, shown as closed slit 1205. Similarly, and now referring to FIG. 13, zip-lock sheath 1320 connected to zip-lock sheath connector 1307 is disposed with zip-lock slit 1301 which is brought together by zip-lock-like fasteners 1303 around the penis which sits in zip-lock sheath cavity 1305.

Figure 14:
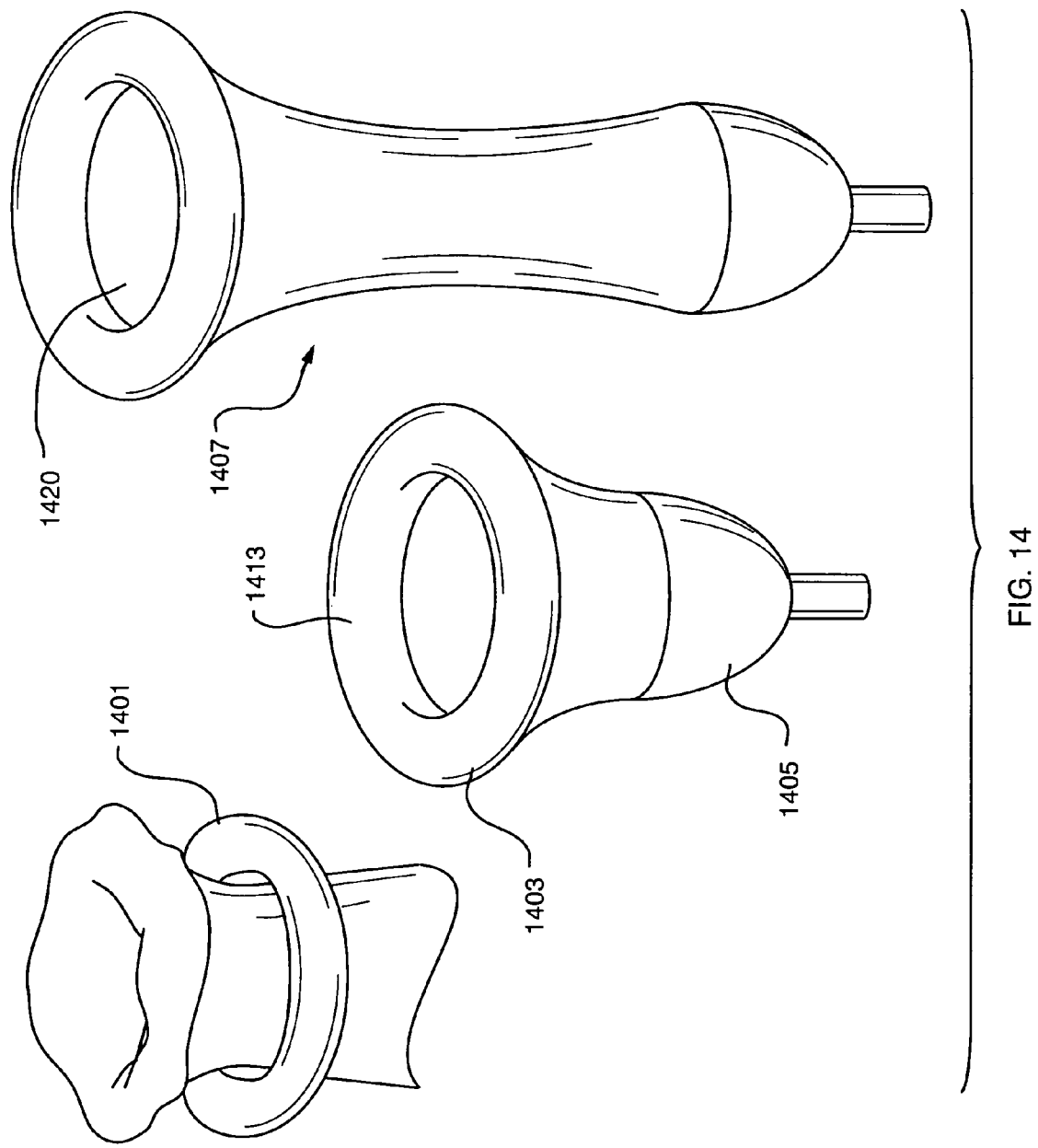
FIG. 14 shows a perspective view of an elastic tube application method for the collection device.
Figure 15:
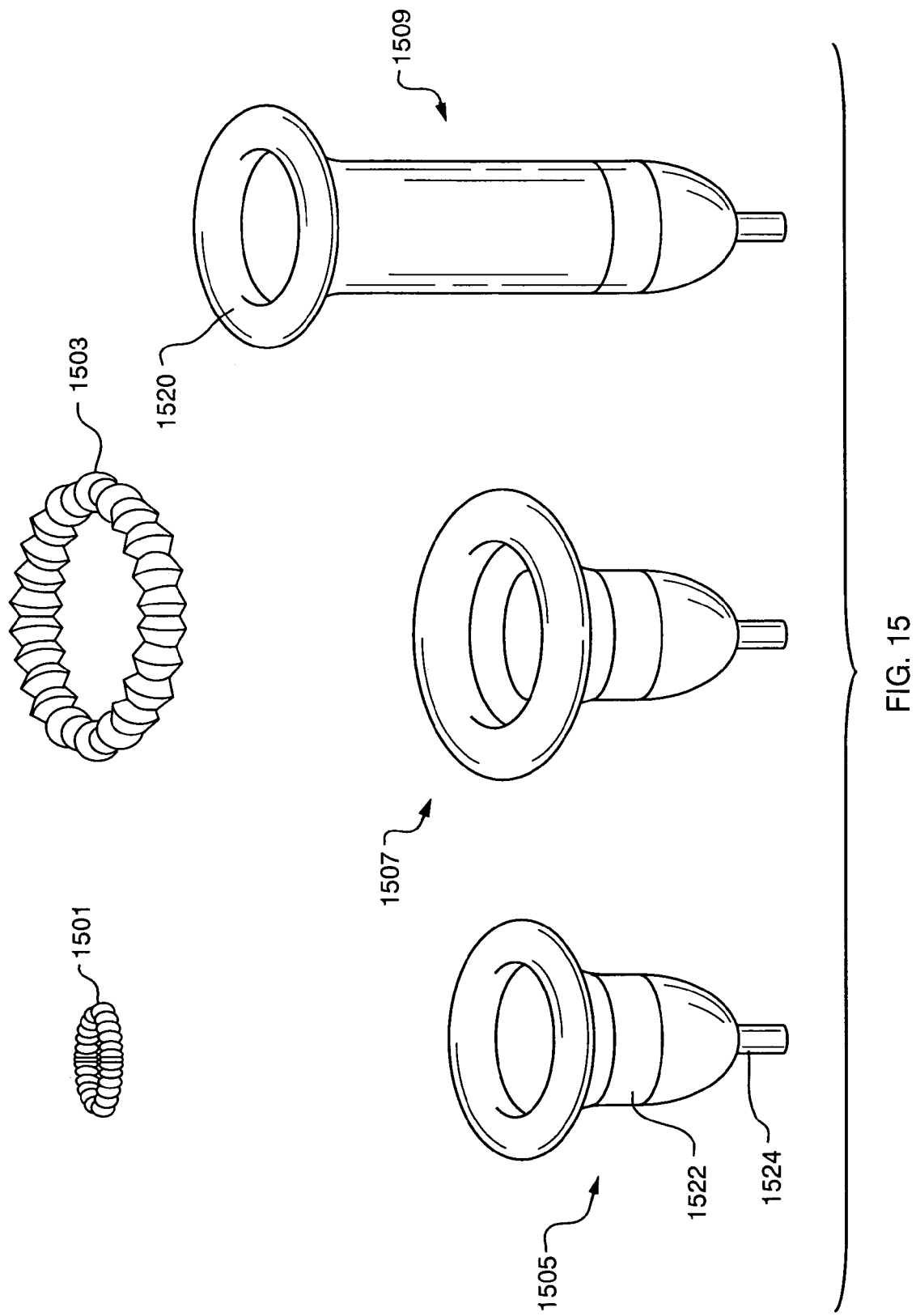
FIG. 15 shows a perspective view of a rigid plastic bellows application method for the collection device.
Figure 16:
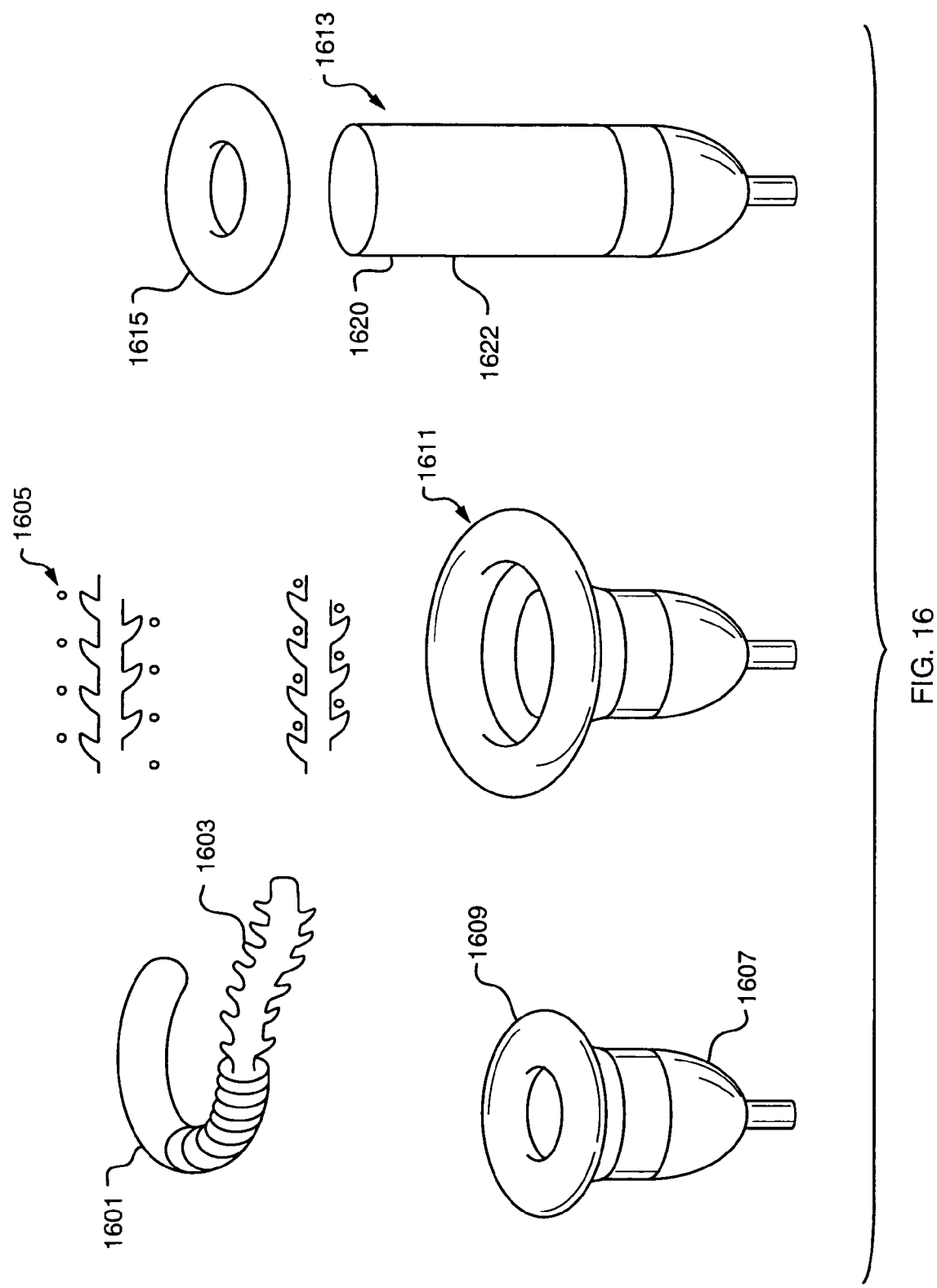
FIG. 16 shows a perspective view of a spring containing a toothed plastic strap application method for the collection device.

Referring now to FIGS. 14, 15, and 16, devices that enable users to apply elastic tubing sheath 1407, expanded length sheath 1509, and unrolled ring and sheath 1613 onto a penis are disclosed. Elastic tubing 1401 is fixedly connected to sheath top 1403 in preparation for rolling elastic tubing sheath 1407 downwards longitudinally from penis entry elastic tubing cavity 1420 to elastic tubing connector 1405. The user unrolls rolled sheath 1413 upwards along the shaft of the penis until elastic tubing sheath 1407 is fully extended. Elastic tubing 1401 helps elastic tubing sheath 1407 to grip and to maintain its position on the penis.

Referring now to FIGS. 15 and 16, for sheaths that can maintain their positions through their own elastic or other frictional properties without the aid of elastic tubing 1401, hook-and-loop fasteners 1201, or zip-lock-type fasteners 1303, reversibly expandable rings such as rigid plastic bellows ring 1501 can be employed. Rigid plastic bellows ring 1501 is removably attached in its unexpanded state to bellows ring sheath top 1520, and co-rolled sheath with attached bellows ring 1505 can be rolled down towards bellows ring connector 1524. In use, the user pulls rolled sheath and attached bellows ring 1505 to expand the rolled diameter 1507 at short length sheath 1522, and unrolls the expanded length sheath 1509 upwards longitudinally along the penis shaft. As expanded length sheath 1509 unrolls and is removed from close proximity to expanded bellows ring 1503, expanded length sheath 1509 shrinks in diameter and grips the penis. When expanded length sheath 1509 is nearly completely extended, expanded bellows ring 1503 and the remaining sheath can be compressed and unrolled to a point where compressed rigid plastic bellows ring 1501 can be detached from the sheath. Detached rigid plastic bellows ring 1501 can then be pulled to expanded bellows ring 1503, removed from the penis, and discarded. Expanded length sheath 1509 can maintain its position on the penis shaft through its own elasticity. Along the same lines, and referring now to FIG. 16, spring coil ring 1615 comprising spring coil 1601 and contained toothed plastic strap 1603 shown in state change 1605 proceeding from exposed state to confined state within spring coil 1601, is removably attached to the cavity perimeter 1620 of lengthened spring coil sheath 1622 and rolled down longitudinally, lengthened spring coil sheath 1622 and spring coil ring 1615 together, towards spring coil sheath connector 1607. Spring coil ring 1615 is completely enclosed by lengthened spring coil sheath 1622. Before use, the user pulls on the co-rolled sheath and attached spring coil ring 1609 to expand the diameter of the co-rolled ring and sheath 1611, places the open end over the penis, and unrolls co-rolled ring and sheath 1611 along the shaft of the penis away from the penis tip until unrolled ring and sheath 1613 is fully extended. As it unrolls and is removed from close proximity to the expanded spring ring, elastic lengthened spring coil sheath 1622 shrinks in diameter and grips the penis. When lengthened spring coil sheath 1622 is completely extended, spring coil 1601 is detached from cavity perimeter 1620 of lengthened spring coil sheath 1622, which retracts elastically to grip the penis. Sping coil ring 1615 is removed from the penis and discarded.

Figure 17:
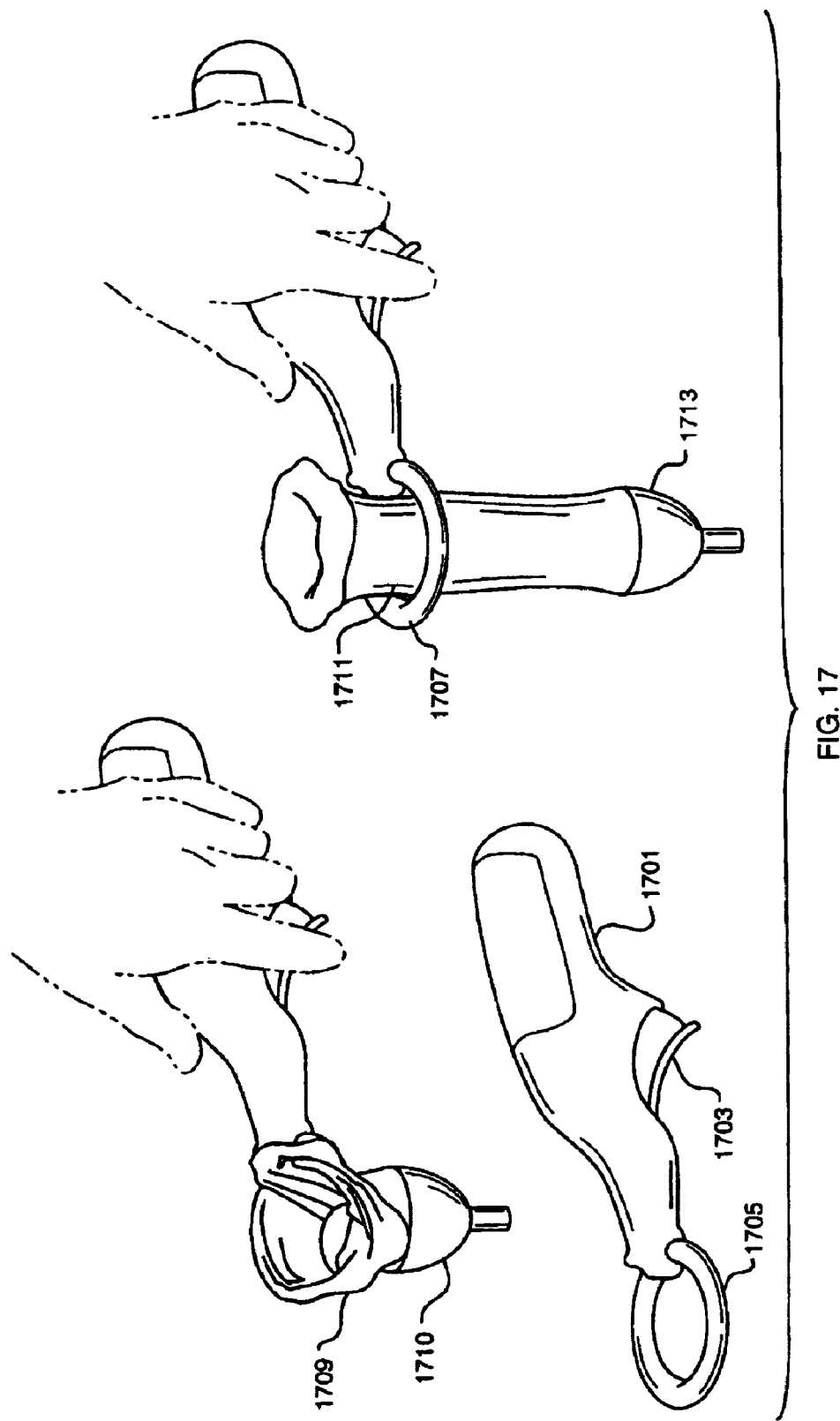
FIG. 17 shows a hand-held application device for the collection device.

Referring now to FIG. 17, hand-held jaw ring expander 1701 for extending the sheath over the penis is disclosed. The user compresses device lever 1703, which causes expansion ring 1705 to open. In use, the end of expansion ring sheath 1711 that is attached to expansion ring connector 1713 is inserted into the expansion ring 1705, in its inactivated compressed state, and penis entry end 1720 of draped sheath 1709 over expansion ring 1705. Then device lever 1703 is compressed, causing expansion ring 1705 and surrounding draped sheath 1709 to increase in diameter. Expanded ring 1707 and expansion ring sheath 1711 are then moved longitudinally up the shaft of the penis. When expansion ring sheath 1711 is nearly fully extended, device lever 1703 is released, allowing expanded ring 1707 and expanded expansion ring sheath 1711 to contract. Any remaining expansion ring sheath 1711 is then unrolled onto the penis leaving expansion ring sheath 1711 self-secured on the penis through its own elasticity. Device lever 1703 is again compressed, which enlarges in-place ring 1707 and allows it to be removed from the penis.

Referring now to FIGS. 1, 2A–B, and 7A–B, in the preferred embodiment for novel urine collection device 20, a wicking spacer element 260 is located within conduction tube 250 between penis tip 262 and collector-conveyance connector 290. Wicking spacer element 260 acts as a wicking flow channel for liquid urine and also serves to prevent complete closure of conduction tube 250 lumen and blockage of flow of free liquid urine when either conduction tube 250 or collector-conveyance connector 290 becomes crimped or folded. Wicking spacer element 260 may be forked or split near to penis tip 262 of penis 261 to enable more effective contact with the inner surface of conduction tube 250.

Referring to FIGS. 1, 2A–B, and 7A–B, all of or selected areas of the interior surface of conduction tube 250 are rendered wettable by urine by any one of several methods known to those skilled in the art, including but not limited to: coating the surface with a wettable coating such as a skin-compatible, nonionic or anionic surfactant that is also compatible with the surface; subjecting the surface to a treatment with charged particles, such as from a high-voltage corona discharge, to render the surface water-wettable; or forming conduction tube 250 from a multi-layer film material in which the interior film layer is more wettable than the outer wall material When the areas of interior walls of conduction tube 250 that are rendered urine-wettable are in contiguous contact with wicking spacer element 260, wicking transfer of urine between wall and spacer element is enabled. Thus, any drops or pools of urine that contact the urine-wettable interior wall areas of conduction tube 250 will be caused to wet and spread out on the wettable surfaces until the spreading liquid urine makes contact with wicking spacer element 260 which will wick up urine, removing it from the interior wall of conduction tube 250 and conveying it to collector-conveyance connector 290.

In order to enable effective connection of novel urine collection device 20 to existent art tubes for conveying urine, and referring now to FIGS. 2A–B, 7A–B, and 10C, collector-conveyance connector 290 attached to conduction tube 250 may be connected through adapter fitting 24 that will cause wicking spacer element 260 and first wicking spacer continuous connection 23 to be located in a region within the connection that will not interfere with gravitational flow of urine into connected existent art urine tube 10EX.

It should be clear that addition of wicking materials to such prior art sheath catheters, none of which are currently equipped for such novel wicking transport, will result in conversion of such catheter devices to fall within the description of the novel conduction tube devices for collection of urine of the instant invention.

Urine Conveyance

Figure 10B:
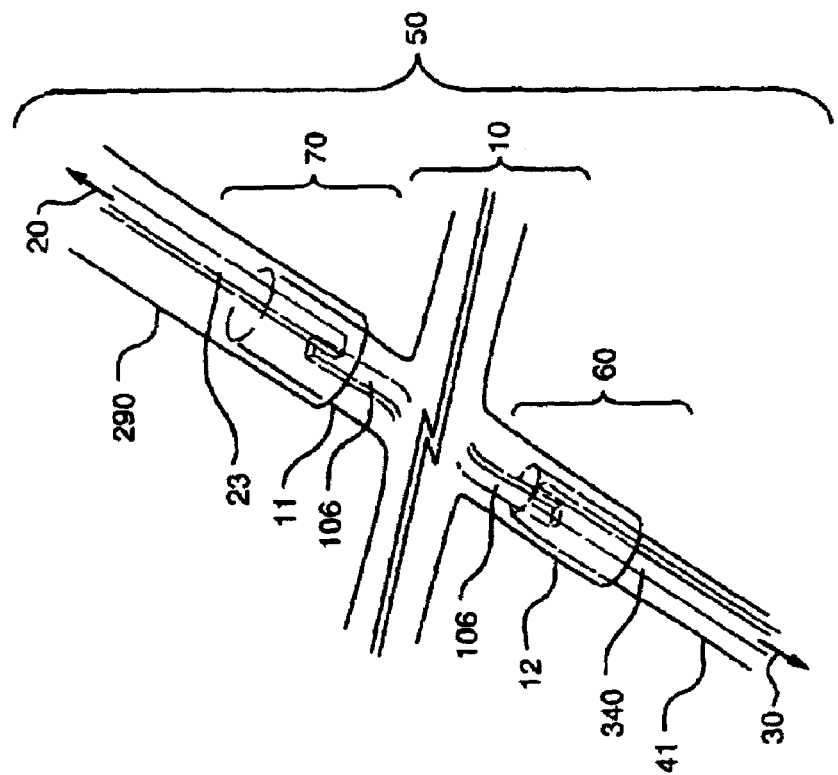
FIGS. 10A, 10B, 10C, and 10D are semi-transparent views of connection and liquid transfer mechanisms used in collection-conveyance and conveyance-storage connections among novel and existent devices.
Figure 10A:
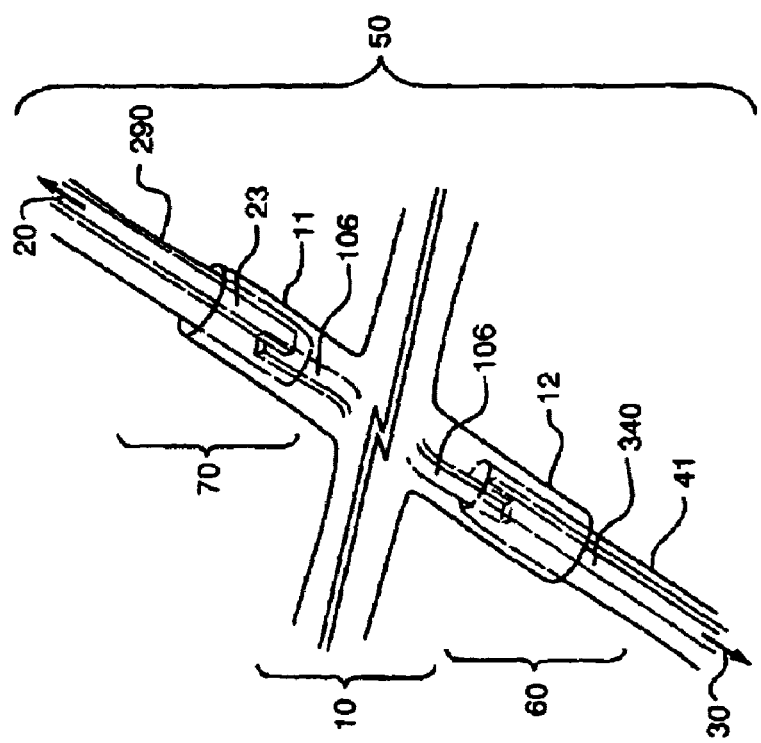

As shown in FIG. 1, novel urine conveyance tube 10 of the instant invention conveys urine from urine collection device 20 to novel urine storage device 30. Referring now to FIGS. 10A, 10B, 11A, and 11B, second wicking interconnection 70 and first wicking interconnection 60 between the urine collection device 20, urine conveyance tube 10, and urine storage device 30 contain contiguously-located, wicking-continuous connections first wicking spacer continuous connection 23 and conveyance tube wicking spacer 106, and conveyance tube wicking spacer 106 and second wicking spacer continuous connection 340, which enable bridging flow of urine between devices. Bridging urine flow, in combination with conveyance tube wicking spacer 106 and urine-wettable lumen surfaces of tube film layer 104 within urine conveyance tube 10, enable the creation of a continuous path of wicking transport within urine management system 50. As shown in FIGS. 10A and B, while the second wicking interconnection 70 may differ dependent upon the relative sizes of collector-conveyance connection 290 from urine collection device 20 and conveyance-collector connector 11 for urine conveyance tube 10, the wicking-contiguous connection between first wicking spacer continuous connection 23 and conveyance tube wicking spacer 106 is accomplished by the combination of second wicking interconnection 70, collector-conveyance connector 290, and conveyance-collector connector 11.

Such continuous paths of wicking transport facilitate siphoning drainage of urine over high point 120 located higher than urine collection device 20 (FIG. 11A), enable storage of urine in urine storage device 30 at locations higher than the collection source (FIG. 11B), and collect and remove to storage those isolated residual pools and drops of urine 9 (FIG. 11C) that might otherwise remain in urine conveyance tube 10 to cause health and skin problems for the user. Wicking-continuous connection with similar means for wicking within urine collection device 20 also enables the wicking actions of urine conveyance tube 10 to aid in removal isolated pools and drops of liquid urine 9 on the inner surfaces of urine collection device 20, It is also within the intent of the instant invention and the relationship of novel urine conveyance tube 10 to the description and intent of novel urine management system 50 that urine conveyance tube 10, urine collection device 20, and urine storage device 30 may be constructed and assembled as contiguous units or subassemblies comprising a plurality of devices in contiguous position within one or more continuous shells that are impervious to urine, and also as a single, continuous unit wherein urine conveyance tube 10, urine collection device 20, and urine storage device 30 are in contiguous position within a continuous shell that is impervious to urine.

Figure 10D:
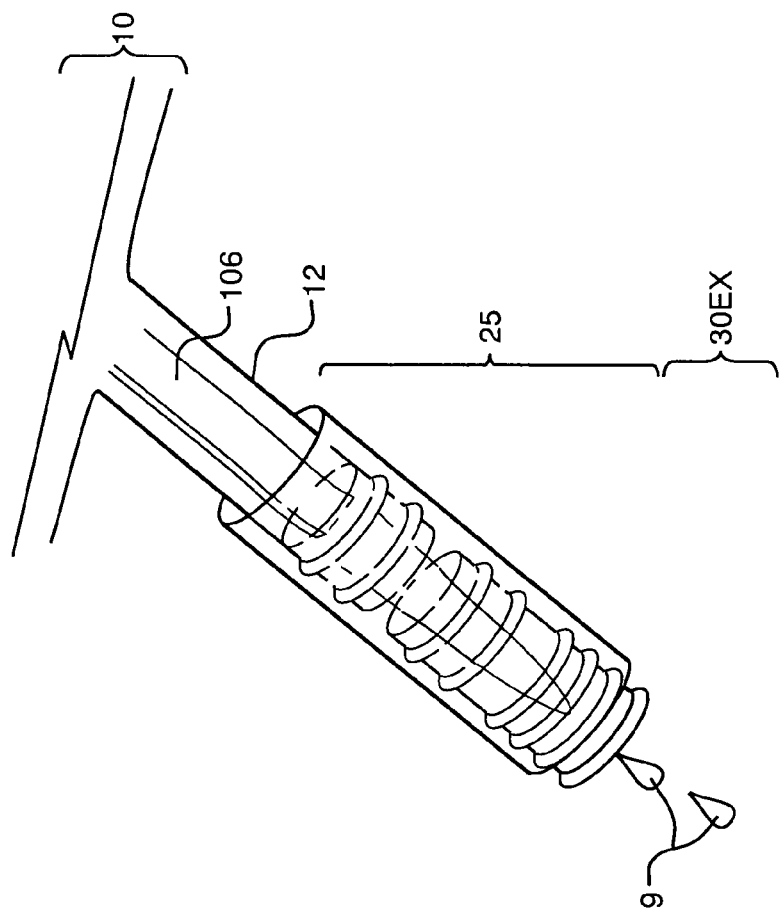
Figure 10C:
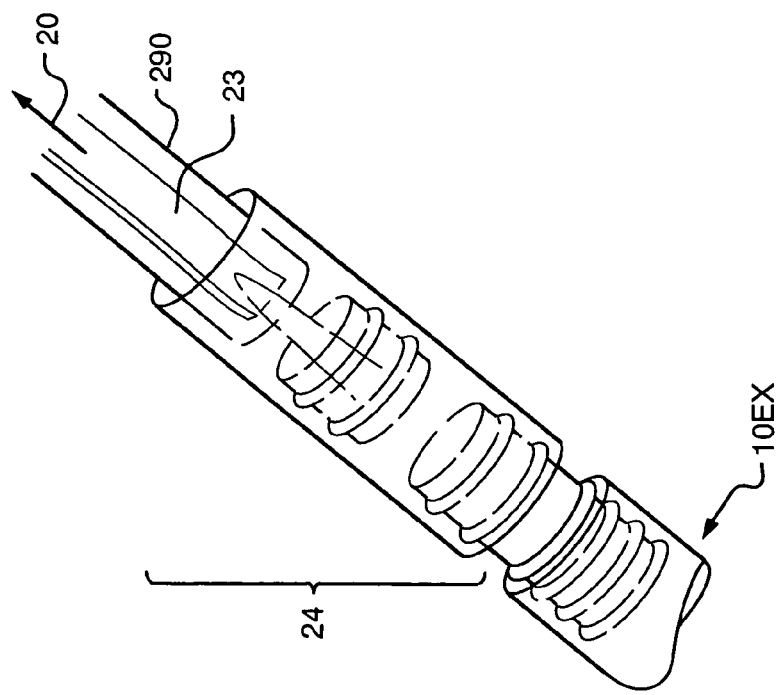

Novel urine conveyance tube 10, also can be used independent of urine management system 50 to perform the function of conveyance in combination with one or more of the existent other devices for collecting urine (e.g., condom catheters) and storing urine (e.g., leg bags), none of which are equipped with means for the novel wicking transport of this invention. Connection of urine conveyance tube 10 for such independent use can be accomplished by replacing connecting devices used in first wicking interconnection 60 and second wicking interconnection 70 with special connecting devices that are dimensioned to connect directly with existent devices to facilitate formation and transport of drops or streams of liquid urine 9 that can be handled by the existent devices. FIGS. 10A and 10B show different configurations for conveyance-collector connector 11 connecting with collector-conveyance connector 290 from either a novel or an existent art collection device. In FIGS. 10D and 11A, an existent art leg bag collection device 30EX is shown connected to novel urine conveyance tube 10 (which is itself connected to novel urine collection device 20) via a second conveyance-collector connector 25 and receiving drops of liquid urine 9 that are being formed at a drip point that is part of second conveyance-collector connector 25 and that is physically located lower than the urine source.

Figure 3B:
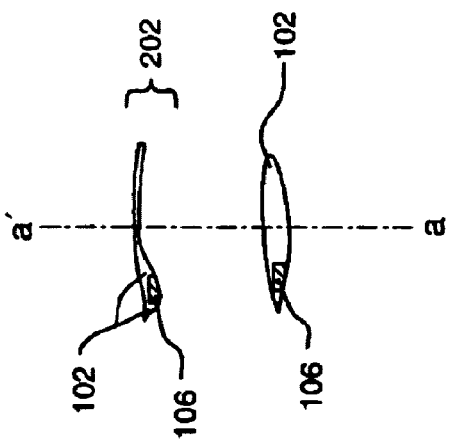
FIGS. 3A and 3B illustrate perspective and cross-sectional views of the conveyance tube which may be thin-walled with spacer in normal and kinked condition.
Figure 3A:
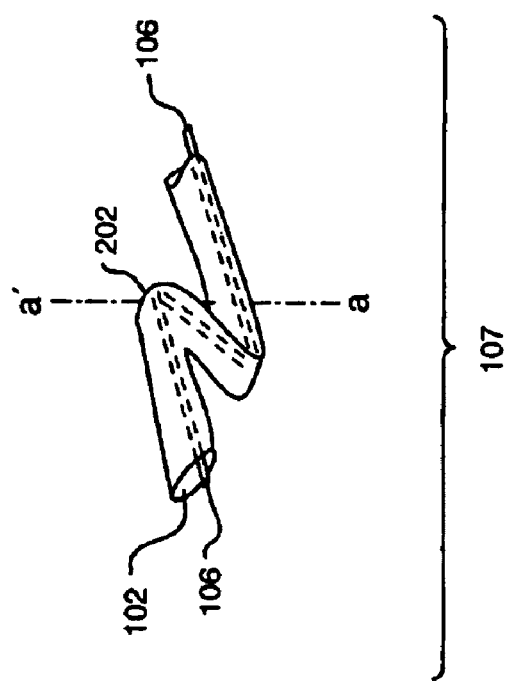

Referring now to FIGS. 2A, 2B, 3A, and 3B, urine conveyance tube 10 comprises waterproof conveyance tube film layer 104 that can easily conform to varied and changing contours and shapes, and can be made from thin-walled plastic film, e.g. 2-mil polyethylene, the inner thin wall and outer thin wall, 1041 and 1042 respectively, of which are illustrated in FIG. 2B. In the preferred embodiment, conveyance tube wicking spacer 106 spans continuously along its length the lumen of urine conveyance tube 10 to prevent urine conveyance tube 10 from becoming blocked when pressed together in a crimping or kink 202 by an external force, as illustrated in FIG. 3A, which would prevent flow through the tube. Presence of conveyance tube wicking spacer 106 prevents full and complete closure of internal wall surfaces of urine conveyance tube 10 leaving enough tube lumen 102 to allow the expected fluid flow to pass. Conveyance tube wicking spacer 106 provides an effectively continuous barrier to wall sealing along the length of urine conveyance tube 10, and may have the same or a variety of different cross-sectional shapes along that length. In the preferred embodiment, conveyance tube wicking spacer 106 is constructed of as flexible a material as possible, is of low density so as not to add substantial weight to the tube structure, has an open, porous internal structure or a high external surface roughness that will result in a porous leaky seal even when pressed against the internal surfaces of urine conveyance tube 10, and is relatively more wettable by water than polyolefins, so as to enable aqueous fluids to wet the surface and interstices.

Conveyance tube wicking spacer 106 may be made in several forms and from a variety of materials: from aggregates of fibrous materials that derive their physical stability from the aggregation (for example, single component or blended fibers of wool, cotton, rayon, nylon, polyester, etc, in the forms of yarns, woven fabrics, mats or felts); from open-cell foamed polymers and elastomers that are wetted by aqueous fluids and that derive their physical stability from the polymer network (for example, polyurethane foams); from open-mesh materials that derive their physical stability from the strength of the individual bound fibers (for example, copper and steel "wools" and meshes and "fiber pads" of synthetic polymers such as polypropylene, and nylon); or from flexible solids (for example, rubbery polymers such as latex and silicone rubbers).

In the preferred embodiment, conveyance tube wicking spacer 106 is made of material with wicking properties, and is capable of conveying and guiding the flow of liquids such as urine that wet those materials and fill the capillary spaces between the fibers or foam cell walls. Thus, in one embodiment, conveyance tube wicking spacer 106 is constructed of rayon felts with a width from approximately 15 to 50 mm (0.6 to 2 inch) and a thickness from approximately 2.54 to 5.08 mm (0.1 to 0.2 inch), while in another embodiment, conveyance tube wicking spacer 106 is constructed of bonded cellulose acetate fiber bundles. In yet another embodiment, conveyance tube wicking spacer 106 is constructed of nylon mesh in different thicknesses or of polyethylene films in 3- to 10-mil thickness. Also in the preferred embodiment, the surface of conveyance tube film layer 104 is either formed from wettable materials or has been subjected to surface treatments to render that surface wettable for holding liquid.

Description of Urine Storage Means

Referring to FIGS. 4A–C, 5A–B, and 6, urine storage device 30 comprises urine wicking and wicking conduit 341, barrier wall 330, and urine absorption/storage element 350, all enclosed within first and second urine-impervious outer walls 310 and 320.

First and second urine-impervious outer walls 310 and 320 are sealed together by thermal or adhesive bonding seals 311 around their perimeter except at first wicking interconnection 60. First and second urine-impervious outer walls 310 and 320 may also be formed from a single sheet of wall material by folding along one edge of perimeter and sealedly attaching the others.

Figure 4A:
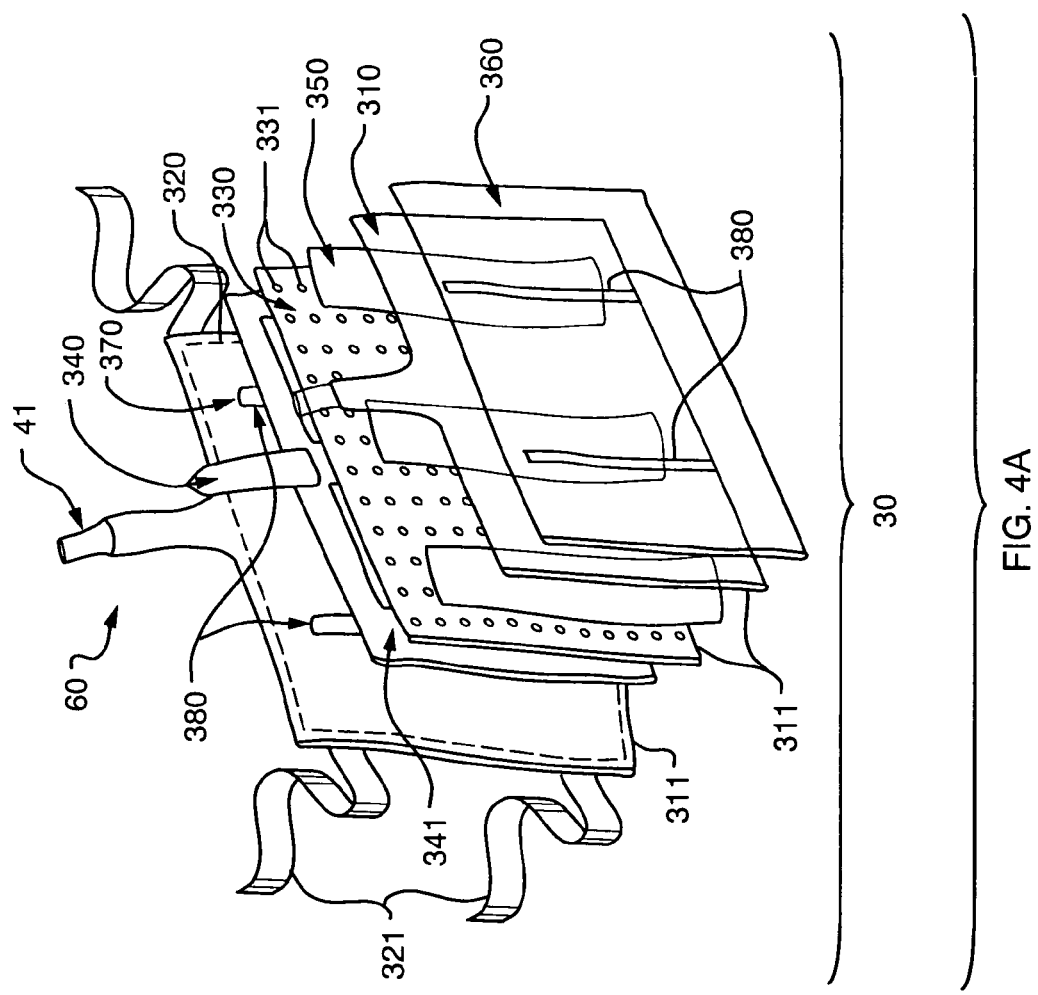
FIGS. 4A, 4B, and 4C present the parts of the storage container in relative position with respect to each other.

Referring to FIG. 4A, barrier wall 330 and first urine-impervious outer wall 310 may also be sealed together along compartment defining lines 380 which cause the absorption/storage region to be divided into contiguous compartments that are interconnected near the top. Second urine-impervious outer wall 320 may also be sealed to first urine-impervious outer wall 310 and barrier wall 330 during formation of compartment-defining lines.

Figure 5A:
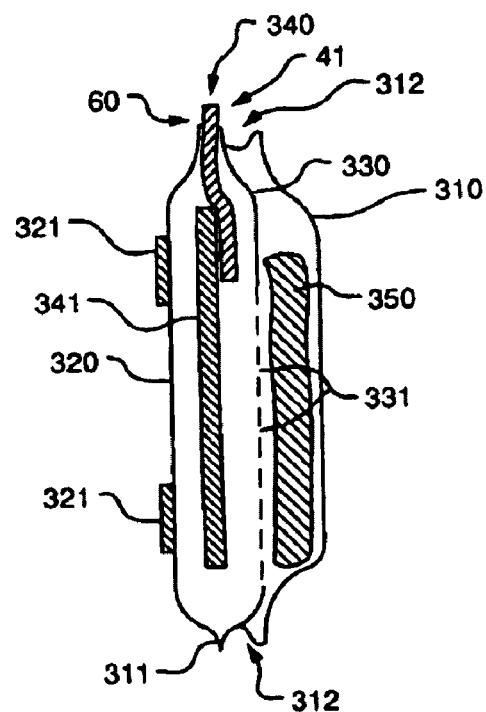
FIGS. 5A and 5B present side views of the storage container.
Figure 5B:
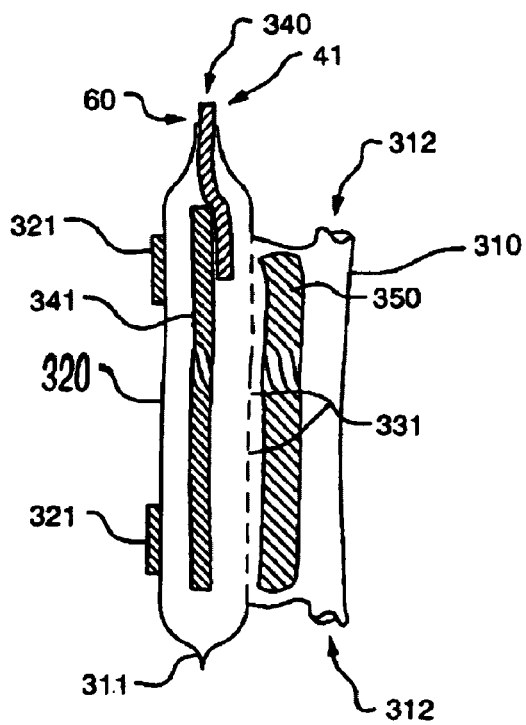

In other embodiments of the device, second urine-impervious outer wall 320 and first urine-impervious outer wall 310 may be of unequal area, being joined with barrier wall 330 along lines such that the distribution and the absorption/storage regions are unequal in areal size, as illustrated in FIG. 5B where first urine-impervious outer wall 310 is attached to barrier wall 330 and the absorption/storage region is smaller.

Referring to FIGS. 5A and B, first urine-impervious outer wall 310 may also incorporate additional wall materials 312, for example into peripheral edges in the vicinity of adhesive bonding seals 311, for example by pleating and folding of the wall material during fabrication, to enable the unused device to have a small volume while allowing for swelling expansion of storage compartment volume when liquid absorption occurs.

First and second urine-impervious outer walls 310 and 320, and barrier wall 330 can be fabricated from any flexible urine-impervious materials such as thin polymer films, e.g., 2-mil polyethylene, coated fabrics, or non-woven fabrics made from non-wetting fibers.

Urine storage device 30 can be attached to the leg of the user by means of attachment straps 321. In the preferred embodiment shown in FIGS. 4A–C, attachment straps 321 are attached to second urine-impervious outer wall 320, however, attachment straps 321 can also be attached to first urine-impervious outer wall 310.

Referring to FIG. 4A, urine storage device 30 may also include first and second additional wall structures 360 and 370 that are exterior to the first urine-impervious outer wall 310 and second urine-impervious outer wall 320, respectively, and that are added for purposes such as improving skin contact comfort or providing added resistance to tearing or puncturing of urine-impermeable front and back walls. Since first and second additional wall structures 360 and 370 do not contact the conveyed or stored urine, there is no requirement that they have a liquid-tight seal in attachment to urine-impervious front and back walls.

Referring to FIGS. 10A and B, within first wicking interconnection 60 which connects urine conveyance tube 10 with urine storage device 30, second wicking spacer continuous connection 340 forms a liquid continuous wicking pathway between conveyance tube wicking spacer 106 and second wicking spacer continuous connection 340 from the conveyance tube wicking spacer 106 which leads to wicking conduit 341.

Figure 4C:
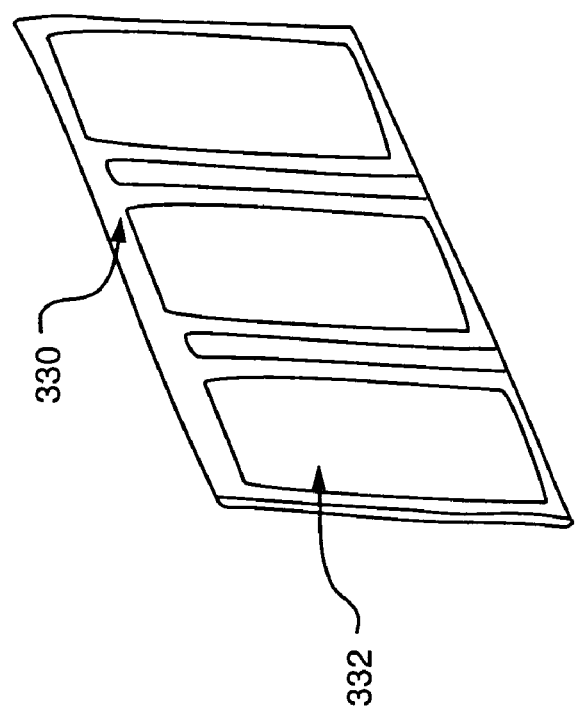
Figure 4B:
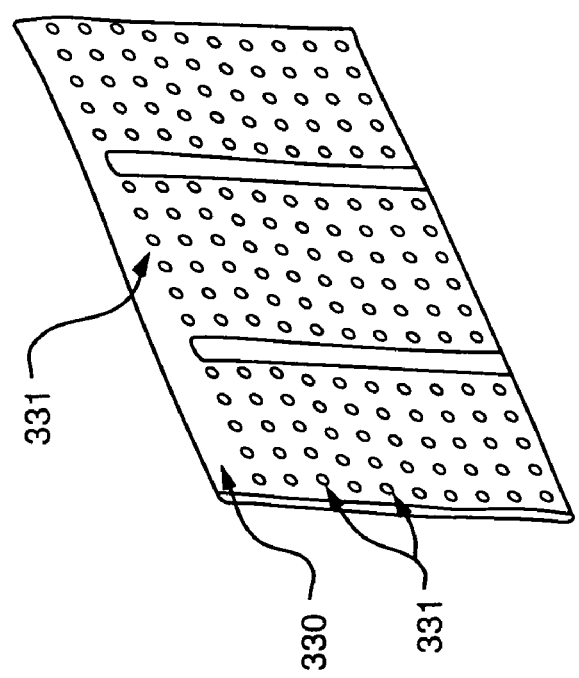

The purpose and function of barrier wall 330 is to limit the volumetric flow rate of urine entering the absorption/storage area in order to avoid the presence of fluid urine in excess of the capacity of the absorbent material. Referring to FIGS. 4A–C, urine flow through barrier wall 330 can be limited by the size, shape, and patterns of barrier passages 331 through the wall material as shown in FIGS. 4A and 4B, or by insertion of one or more panels of urine-permeable material 332 into the wall as shown in FIG. 4C.

Only free liquid urine or water vapor can pass through the flow limiting perforations or urine-permeable regions in the barrier wall 330. Urine present within the interior of wicking conduit 341 will only have access to the barrier passages 331 through liquid-continuous connection to external free liquid. Thus, free liquid urine must be present on the surface of the wicking conduit 341 or be in contact with a urine-wettable surface which itself is in contact with the perforated or permeable area in order for transfer of urine to take place.

Urine that passes through the perforations or through the permeable areas will appear as free liquid on the other side of barrier wall 330, and can be imbibed and absorbed by the absorbent present in absorption/storage element 350. Imbibing liquid urine causes many absorbents (e.g., superabsorbent polymers) to swell in volume. As urine is imbibed into an absorption/storage element 350 that contains such a swelling absorbent, the region of absorbent element nearest to the liquid urine entry point (perforate hole or permeable region) will swell in volume and when confined in a volume that is less than the volume that would be occupied by absorbent in a completely swollen condition, will eventually swell to an extent such that the swollen absorbent will offer resistance to entry of additional urine through that entry perforation or permeable location. Since liquid flow will seek the path of least resistance, the liquid urine will then enter through other perforations or permeable regions where the absorbent is not yet swollen. The overall effect will be to promote distribution of the urine to those regions in the absorption/storage element 350 that are incompletely filled until all regions have been filled to capacity. Capacity is governed by the volume of absorption/storage element 350, the distribution of barrier passages 331, and total amount of absorbent in absorption/storage elements 350.

Figure 6:
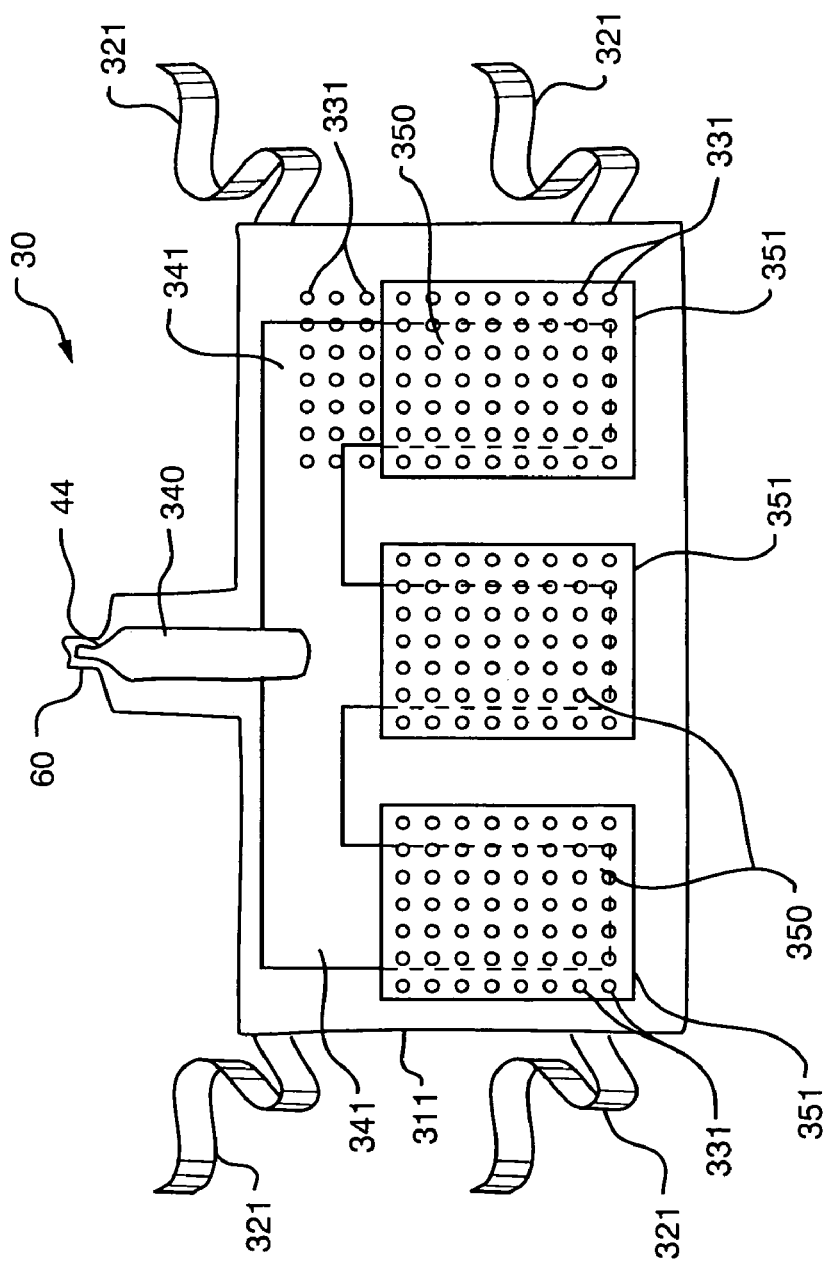
FIG. 6 presents a transparent front view of the interior of the storage container.

Referring to FIGS. 2A–B, urine will arrive at first wicking interconnection 60 either via wicking flow through conveyance tube wicking spacer 106 or as a free-flowing liquid through tube lumen 102. Referring now to FIGS. 5A–B and 6, at first wicking interconnection 60, wicked urine and free liquid urine will be imbibed by second wicking spacer continuous connection 340 and wicking conduit 341 or directed as free liquid into the single or multiple compartments in urine storage device 30, thence directed toward the perforation or barrier passages 331. The rate of absorption and capacity of urine absorbents have finite limits for each type of absorbent. To control passage of urine into the absorption area, storage device barrier wall 330 is perforated with an array of barrier passages 331 of sufficient size and number to afford the desired flow of urine through the barrier in a pattern that results in a more or less uniform wetting of absorption/storage element 350.

Wicking conduit 341 is a capillary wicking material located between second urine-impervious outer wall 320 and barrier wall 330. Thus, a liquid-continuous path of wick material is present from first wicking interconnection 60 to lower edges of absorption/storage element 350.

Absorption/storage element 350 is located in each of the one or more separate compartments in urine storage device 30 in order to provide for uniform distribution of absorbed urine. Absorption/storage element 350 can be fixedly or removably attached to urine storage device 30 compartment walls. Absorption/storage element 350 may include any of a variety of commercially available products: gel-forming resins (for example, polyacrylamide, polyacrylic acid or its Na+ salt, polyacrylic acid grafted onto starch or its Na+ salt), a paper-like matrix of cellulose or other fibers that may contain fine particles of such gel-forming resins, needle-punched felt fiber pads, absorbent paper, or inorganic absorbents (for example, silica gel) that may be in combination with other aforementioned absorbents. Absorbent materials may also include physical adsorbents such as capillary wicking materials that attract and hold liquids in their interstitial volume.

For attachment to the human body, urine storage device 30 is folded around the contour of, for example, the calf, and attachment straps 321 are used to effect attachment via adhesive, hook and loop or other means.

Description of Urine Wicking Means and its Effects

Each of the devices contains a wicking spacer component throughout the working length of the lumen of the device— wicking spacer element 260 in the collection device, conveyance tube wicking spacer 106 in the conveyance device, and second wicking spacer continuous connection 340 in the storage device. When urine conveyance tube 10, urine collection device 20, and urine storage device 30 are serially connected as shown in FIG. 1, then the respective wicking spacers are brought into contiguous contact by the coupling of collector-conveyance connector 290 and conveyance-collector connector 11 to form the collection contiguous wick connection 13 between the wicking spacers in the collector and conveyance device, and by coupling of conveyance-storage connector 12 and storage-conveyance connector 41 to form the contiguous wick connection 121 between the wicking spacers in the conveyance device and the storage device. Contiguous wick connections 13 and 121 are of sufficient size so that the resistance to flow across each of those contiguous contacts is not a flow-limiting point along the urine flow path. With good contiguous contact, urine that is traveling along a wick will easily bridge the gap between wicks and thus continue to move in the series-connected wicks in the same manner as if the connected ones were a single wick.

By using a material that is easily wetted by urine as the inner layer or coating on the inner layer of collector conduction tube 250 or conveyance tube film layer 104, separate pools or drops of liquid urine 9 will, upon contact with wettable surfaces, immediately wet the wettable surfaces and spread across them. If such wettable surfaces are themselves in contact with a wicking spacer, then the separate pools or drops of urine will be transferred to the wicking system and conveyed to the storage device, thereby causing the location(s) of the pools or drops of liquid urine 9 to become essentially free of liquid urine. It should be noted that the skin of penis 261 also constitutes a urine-wettable surface.

In hydraulically connected systems, fluid flows from regions of higher to lower pressure. In a gravity-driven system, flow is from a higher physical point (i.e. higher pressure from height×density×gravitational constant) to a lower physical point (i.e., lower pressure from height×density×gravitational constant). In urine-imbibing materials such as incompletely saturated wicks and absorbents, the relative fluid pressure is influenced by the physical and chemical forces that hold the urine; the stronger those forces, the lower the relative fluid pressure. Thus, under some conditions where the wicking and absorbent materials have absorbed only a portion of their capacity, urine can flow in an ascending path to be imbibed by the partially saturated absorbent. In the contiguously-connected urine wicking system of the instant invention, the direction and rate of flow of urine within series-connected wicking spacer element 260, conveyance tube wicking spacer 106, and second wicking spacer continuous connection 340 will be driven by the relative fluid pressure of the hydraulically-connected streams and pockets of urine in wicks and their associated contacting areas including the inner surfaces of conduction tube 250 in the immediate vicinity of penis 261, the surfaces of conveyance tube film layer 104 where excess liquid urine flows, and absorption/storage element 350 in the storage pack. Thus, free liquid urine can be wicked away from the vicinity of penis 261 and internal surfaces of conduction tube 250, conveyance tube film layer 104, and storage-conveyance connector 41. In addition, of the urine present in the wicking spacers, any excess liquid urine (e.g., urine not held within capillary spaces) will be subject to hydraulically induced flow from the wicks into the lower pressure regions in absorption/storage element 350 within urine storage device 30. Thus, any freshly-emitted incontinence leakage reaching the walls of conduction tube 250 will be induced to flow away from the penis region, leaving the skin of penis 261 generally in a much drier state than would be experienced with prior art collection devices.

Removal of the excess liquid urine from the skin of penis 261 and from surfaces in urine collection device and urine conveyance tube, 20 and 10 respectively, also reduces the volume of nutrients and fluid urine available to the various microbiological organisms that can grow and flourish in stale, standing urine. These microorganisms are frequently the source of urine decomposition products (e.g. ammonia)

that are detrimental to the moist penis skin. Since the wick remains wetted with urine, the possibility exists that microorganisms may grow and thus become transferable back to the user. As a means to limit the growth of undesirable microorganisms in the urine within the wick, antibacterial materials can be applied to the wick substrate as surface coatings or treatments, or can be compounded into fibers, formed into similar wicking materials and attached in contiguous contact with the wicking spacer. There are commercially-available antibacterial materials whose properties are appropriate for the human contact use and that are effective against the organisms of concern for the situation (e.g., Escherichia coli, Pseudomonas aeruginosa); for example, Surfacine®, a silver-based antibacterial coating material from Surfacine Development Company, Tewksbury, Mass. is reported to be effective. To prevent growth of bacteria, wicking spacer element 260 and conveyance tube wicking spacer 106 are coated with antibacterial substances. The coating process would be expected to cover all external and internal surfaces of the wick body in the region treated. The size of the treatment region is determined by the residence time required to achieve the desired limitation and control of the target microorganisms.

The connections between devices may be fabricated so that they are permanent or are attachable/detachable to enable periodic replacement. In the preferred embodiment, nested fittings in upstream collector-conveyance connector 290 and conveyance-storage connector 12 are the inner fittings and conveyance-collector connector 11 and storage-conveyance connector 41 are the outer fittings. Other embodiments include combinations of permanent and detachable connections among the three devices: all devices detachably connected; collector device permanently connected to conveyance device that is detachably connected to storage device; and all devices permanently connected.

The following examples serve to substantiate the validity and novelty of the instant invention, but do not serve to limit the invention's scope as described and claimed herein.

EXAMPLE 1

Device Enabling Intermittent Conveyance of Urine Over a Point Higher than the Source Test 1) A 10-cm long×1.0-cm wide×0.30-cm thick piece of a commercial rayon acetate needled felting (basis weight=220-g/sq meter (7.2 oz/sq yd); water holding capacity 2.6-g water/3.0-cu cm volume) was held suspended lengthwise above the surface of 0.9-wt % NaCl solution with the bottom edge of the felt strip immersed ca 1.0-cm beneath the surface. The felt was rapidly wetted by the solution and more solution was added as needed to maintain the liquid level. The wetted front, which showed the point to which the felt was filled with solution, was observed to rise to an upper limit ca 7.5- to 8-cm above the solution's surface Test 2) An 18-cm×1.0 strip of the same felt was pulled through a 15-cm long×5-cm inflated diameter piece of thin-wall polyethylene (PE) "lay flat" (i.e. flattened and rolled immediately after forming) tubing (0.005-cm wall; 3.5 cm wide when flattened) so that the bottom 2.0 cm of felt was uncovered. The bottom 1.0 cm of uncovered felt was suspended in the solution as in Test 1, and the liquid level again rose 7.5 to 8 cm above the liquid surface. The outer surface of the wetted felt was seen to have visible liquid on it.

Test 3) A second 18-cm×1-cm piece of felt, enclosed within a like piece of the same thin-wall PE lay flat tubing, was draped over an 0.5 cm diameter metal rod at a point about 8 cm above the bottom edge of the tubing. When the bottom 1 cm of the felt was dipped into the solution, solution rose in the felt until it passed over the rod and then passed down the felt to the other ("top") end of the felt. The "top" end of the felt was above the level of solution in the reservoir, and no liquid dripped from the top end.

Test 4) At the conclusion of Test 3, when no solution had dripped from the "top" end of the felt, a 5 cm length of the same felt was attached to the "top" end by overlapping the two pieces of felt over a 1 cm distance and fastening on the fresh piece with a paper clip to achieve good contact between the felts. The unattached end of the added felt strip was allowed to hang outside of the solution reservoir, and was seen to be below the level of the solution surface in the reservoir. Solution then passed from the outside surfaces of the "top" end of the original felts strip into the added 5 cm strip, and continued to flow down this added strip until reaching the lower end, at which point solution dripped from the lower end. The liquid level in the reservoir was observed to drop as dripping continued, indicating that solution was being siphoned out of the reservoir.

Test 5) At the conclusion of Test 4, additional solution was added to the reservoir to again submerge the bottom 1 cm under solution, and solution was observed to be dripping from the added strip. The bottom felt was then lifted sufficiently to bring the bottom tip above the surface, and solution dripping was observed to stop quickly. When the bottom felt was re-submerged under the solution surface, dripping from the added felt resumed. This stop and start action could be repeated with stop periods of several hours as long as sufficient solution remained to wet the bottom felt. Hence, siphoning through a wetted will remove solution that appears only intermittently.

EXAMPLE 2

Device Enabling Intermittent Conveyance and Storage of Urine at a Location Higher than the Source Test 1) An 18 cm×1 cm piece of the same rayon acetate felt as used in Ex 1, enclosed within a like piece of the same PE lay flat tubing, was draped over an 0.5-cm diameter metal rod at a point ca 8-cm from the bottom edge of the tubing. The section of the felt strip above the metal rod was then led horizontally to a solution absorption pack which comprised a 10 cm long×2.5 cm wide×1 cm thick pouch made from a polyester non-woven scrim (87 g/sq M), containing 1.0-gram of sodium polyacrylate (Salsorb CL15, Allied Colloids, Suffolk Va.) and having edges sealed with double-faced acrylic adhesive tape. The non-woven pouch material was easily wetted by the saline solution. When the bottom 1-cm of the felt was dipped into the solution, solution rose in the felt, passed over the rod and traveled through the horizontal section to the "top" end of the felt. Solution, which was visible on the surface of the felt, quickly wicked to the polyester non-woven pack at contact points and then wicked along the non-woven until it contacted sodium polyacrylate solids which quickly absorbed all solution liquid transported to it.

Test 2) Test 1 above was repeated but with a layer of polyethylene film 0.010 cm thick perforated with 0.08 cm diameter holes on 1.0 cm centers (paper clip hole punch) imposed between the solution-wetted felt and the polyester solution absorbent pack. Layers in the resulting "sandwich" were held in close contact with two #1 paper clips. With a dry absorption "sandwich" which had not yet been wetted through, when the bottom end of felt strip was placed in the solution, solution wicked to the upper end of the strip, but did not pass through the perforated PE film barrier.

Test 3) When the felt and "dry" absorption pack "sandwich" used in Test 2 above was placed at a position lower than the surface of solution in the reservoir, solution wicked into the felt and emerged from the felt surface, as the siphoning action progressed, until solution bridged across the space to the perforated film. As additional solution emerged and collected in the gap, it began to penetrate the perforations. Solution passing through a perforation emerged as a droplet on the other side of the barrier wall. When a droplet had expanded to the point that it contacted a portion of the non-woven polyester, it wetted the polyester and began to wick along the fibers without breaking off from the stream passing through the perforation, thus forming a continuous wicking channel from the felt to the absorbent pack. Once wicking channels through the perforations had been established, the absorbent pack "sandwich" could again be placed at the location higher than the source, albeit not higher than the wicking capability of the felt as demonstrated in Example 1, and the wicking action would lift and store solution at a point higher than the surface of the reservoir. The capacity of the absorbent for storage at locations higher than the source is less than when the storage location is on the same level as or lower than the source as indicated by the appearance of the absorbent bed in the higher location; beds loaded at higher locations appeared visibly less wetted when they ceased taking up additional solution than beds that were loaded at lower locations.

Test 4) During wicking to a higher location as in Test 3, when the bottom of the felt strip was removed from the solution, solution transfer into the absorbent pack was observed to slow and stop, and some of the wicking streams passing through the barrier film perforations broke off. When the bottom felt was re-submerged under the solution surface, solution flow through the intact perforation streams, and take up in the absorbent material, resumed.

This stop and start action could be repeated with stop periods of several minutes as long as some of the wicking stream contacts through the barrier perforations remained. Flow through the other barrier perforations could be restarted by lowering the absorbent bed as in Test 3.

EXAMPLE 3

System Enabling Removal of Drops or Pools of Liquid Urine from Walls of Thin-Wall Non-Wetted Tubing Test 1) A 30-cm length of thin-wall PE "lay-flat" tubing, which had a 1.0-cm wide×0.3-cm thick strip of rayon felt throughout the entire length of its lumen, was subjected to a flow of 200-cucm of aqueous 0.9% NaCl solution which passed through the tube during a 5–7 second time interval as a continuous stream which caused the tube walls to open up to an oval shape during passage of the liquid volume. After the liquid had passed, the tube walls reverted to their flattened shape in which the walls were nearly touching. Any liquid drops that were in contact with the felt were wicked away, and only a few drops of liquid, which were isolated from the felt wicking, remained along the inner wall surfaces.

Test 2) A 10-cm length of thin-wall PE lay-flat tubing was cut open on one edge and the surface that had been the interior was lightly but completely wiped with a piece of the rayon felt that had been wetted well with commercially-available liquid cleaner material. The wiped surface was allowed to dry for one hour in ambient room atmosphere. Clean strips of the same rayon felt were placed along one edge of the wiped surface, and on an edge of an upwiped interior surface of the same PE tubing. Then drops of 0.9% NaCl aqueous solution were applied to each of the PE film surfaces at several locations not in direct contact with the fresh felt strip. On untreated film the drops of solution sat immobile with a high contact angle unable to wet the film surface. However, on the cleaner-treated PE film the drops wetted the surface and spread out eventually coalescing and flowing to lower points until the flow reached a point of contact with the felt, at which point the solution stream was taken up by the felt.

A similar test was performed on the interior surfaces of 10-cm intact segments of the same thin-wall PE lay-flat tube. The tube segments were inflated with air before being used in order to break the wall-to-wall adhesion that existed in the unused tubing. In these tube tests, the interior surface was wiped with the cleaner-wetted felt, and a strip of unused felt was placed along one edge of the tube. A 50-cucm volume of aqueous 0.9% NaCl solution was then passed through each tube during a 5-sec time period. After the NaCl solution had passed, residual drops remained in the untreated tube, while any residual liquid that was visible in the treated tube quickly disappeared from view being visibly wicked away and taken up by the felt strip.

Other means for rendering the surface of PE films wettable by water, such as corona discharge or flame treatment that degrade and etch the PE surface thereby rendering it hydrophilic, will also provide a degree of enhanced wettability that will enable coalescence and wicking away of residual aqueous solutions.

EXAMPLE 4

Use of Separate Spacer in the Lumen of Thin-Wall Urine Conveyance Tube to Prevent Flow Stoppage Due to Squeezing or Crimping of the Tube Test 1) A 30-cm length of the same PE flat tube (0.005-cm wall thickness) was crimped by folding at the midpoint to give a 5-cm long folded region that was then folded on itself to give four (4) layers of tubing, and the second fold was secured across the width of the folds by clamping with a spring steel paper binder clip. The jaws of the clip were covered with a thin layer of foamed PE to deliver uniform pressure on the folded tube; jaw pressure was approximately 16-psi.

Prior to folding, one end of the flat tube was connected via a flexible PE tube to a reservoir of water in a flexible bag while the other end was closed by heat-sealing. In the non-folded tube, raising the reservoir level to 0.5-cm above the tube was sufficient to cause rapid flow of water from the reservoir into the tube.

When the tube was folded to four thicknesses and clamped as described above, raising the reservoir to give a pressure head of 12-cm of water above the crimp point did not give any perceptible flow of water into the tube over a 60 minute test time. Thus, under these test conditions, a four-fold crimp in the tube will completely shut off water flow through the tube. Measured thickness of single layer of tube was 0.010-cm.

Test 2) The crimp and pressure procedure of Test 1 was repeated on a length of the same thin-wall PE tubing into which a 2.5-cm wide strip of a lightweight polyester non-woven material (23-g/sqM) had been inserted as a spacer through the length of its lumen. Measured thickness of single layer of tube and spacer was 0.015-cm. A water head pressure of 10-cm above the crimp resulted in a flow rate of approximately 3-cucm/hour.

Test 3) The crimp and pressure procedure of Test 1 was repeated on a length of the same thin-wall PE tubing into which a 2.5-cm wide strip of a cellulose-polyester non-woven material (58-g/sqM) had been inserted as a spacer through the length of its lumen. Measured thickness of single layer of tube and spacer was 0.030-cm. A water head pressure of 9.5-cm above the crimp resulted in a flow rate of approximately 6-cucm/hour.

Test 4) The crimp and pressure procedure of Test 1 was repeated on a length of the same thin-wall PE tubing into which a 2.5-cm wide strip of a cellulose-polyester non-woven material (77-g/sqM) had been inserted as a spacer through the length of its lumen. Measured thickness of single layer of tube and spacer was 0.043-cm. A water head pressure of 9.7-cm above the crimp resulted in a flow of approximately 10-cucm/hour.

Test 5) The crimp and pressure procedure of Test 1 was repeated on a length of the same thin-wall PE tubing into which a 2.5-cm wide strip of a rayon acetate needled felt (250-g/sqM) had been inserted as a spacer through the length of its lumen. Measured thickness of single layer of tube and spacer was 0.086-cm. A water head pressure of 4.3-cm above the crimp resulted in a flow of approximately 140-cucm/hour.

EXAMPLE 5

Use of a Barrier with Flow-Limiting Passages to Control Flow of Urine to Solid Absorbent in Device for Storage of Immobilized Urine Test 1) Example 2, Test 1 showed that an absorbent polymer, when enclosed in a pouch made from a light-weight, flexible, wettable fabric, will rapidly absorb aqueous solution at points of contact with channels bearing those aqueous solutions such wetted felts.

Test 2) Repeated Test 1 with additional pouches containing absorbent polymer in which the polymer solids were either collected as a single "pile" in a corner or along an edge of the pouch, were distributed in a more-or-less uniform layer over the entire interior area of the pouch, or were confined, before being wetted, within a lightweight cellulose-fiber non-woven sheet that was held in place within the pouch. In order to provide adequate room for expansion, the ratio of polymer to pouch volume was maintained at approximately 1-g solids/50-cucm of pouch volume (12-cm×4-cm×1-cm).

When the absorbent polymer was in a relatively thick "pile", parts of the outer layer would be easily wetted at the wick contact regions and would quickly swell. While the wetted regions would act as a channel for inflow of additional solution, bypassing regions where contact had not been established, the swelling polymer particle appeared to act as a barrier to free passage of solution to underlying regions. Excess free liquid would accumulate in some outer regions until slowly absorbed by the mass. This uneven solution distribution could be remedied quickly by mechanical mixing of the polymer, but re-distribution of excess solution without mixing, i.e. by purely diffusional and surfacial flow transport, generally required a 1–4 hour time period.

When the absorbent polymer solids were distributed uniformly over the pouch area, which resulted in a relatively thin layer of solids, then the entire depth of the layer would be wetted before the top particles swelled sufficiently to block inward flow.

Test 3) Example 2, Test 3 showed that when a layer of thin PE film with periodic perforations is placed between a strip of felt wetted with aqueous solution and a pouch made from a wettable fabric containing an solution-absorbing polymer, excess solution will emerge from the felt and begin to fill the region between the felt and the barrier film until pressure in that region forces some solution to pass through some of the perforations. Under the influence of gravitational forces, solution initially filled and penetrated perforations in the lower region of the test configuration. Unrestrained polymer particles also were free to accumulate at the bottom of the pouch.

As polymer at the bottom of the pouch began to swell, is expanded to fill that region continuing to expand until it clogged the lower perforations. As the flow impedance in the lower perforations increased, solution flow was observed to become diverted to higher perforations, which also eventually clogged. Thus, flow was diverted from regions filled with swollen polymer to those where less solution had been taken up. This diversion provided an improved means to ensure that solution uptake was as rapid and uniform as possible in an unmixed system.

EXAMPLE 6

Use of Radial Compression Tube for Stabilizing (Securing) Location and Providing Liquid Seal in Urine Collection Device Test 1) A single-layer tube 2.5-cm in diameter and 6-cm long was fabricated from a spandex fabric (polyester; 250-g/sqM;) by sewing along the longitudinal line. This tube could be expanded in diameter over 100% by gripping the sides with fingertips. The expanded tube could be fitted over a 3-cm diameter×10-cm long cylinder of rubber foam simulating a penis. When in place, the spandex fabric tube easily conformed to shape differences on parts of the rubber foam cylinder.

Areas on the interior surface of the spandex fabric tube were lightly coated with a fluid rubber cement and allowed to dry. Those areas that had received the coating provided a surface of noticeably higher frictional force on the skin of the back of a hand, showing that a friction-enhancing coating will enable the tube to remain in place on a somewhat slippery skin surface.

Other areas coated with fluid rubber cement were bonded to a thin sheet of latex rubber from latex glove and allowed to dry. Water drops placed on the fabric side wetted the spandex fabric and flowed along it while not penetrating the latex layer. In addition, when a strip of rayon acetate felt was placed in contact with the wetted spandex fabric, the rayon felt would take up free water. When additional water was placed on the wetted regions of the spandex fabric, the added water could be seen to flow across the wetted regions and to be taken up by the rayon felt.

Other areas of the interior surface of the tube were coated with a commercial silicone-containing waterproofing fluid, which left a coating on the threads, but not bridging between them. Water easily penetrated untreated areas of fabric, but remained as drops on the surface of the treated areas. Water vapor was easily able to penetrate and evaporate through the open fabric mesh.

EXAMPLE 7

Characteristics of Thin-Wall Flat Tube that Enable a Profile Shape

Test 1) The PE tubing remained essentially in its flattened form except where the felt was present, or when a volume of solution was passed through or held in the tube. When felt solid or solution was removed from the tube lumen, the tube flattened out again to a point where the walls were almost touching.

Test 2) When a finite volume of aqueous solution was passed through the flattened thin-wall tubing, the lumen would rapidly and easily expand to oval or round shape to accommodate the volume, and then return to its flattened configuration. Thus a 5.0-cm inside diameter thin-wall tube has a configuration of 3.5-cm×0.1-cm flattened (lumen capacity of 0.35-cucm/cm length) when flattened and a configuration of a 5-cm diameter cylinder (lumen capacity of 15.7-cucm/cm length) when fully expanded. This reversible wall expansion permits the thin-wall flattened tube to conduct a relatively large volume periodically without being burdened by a permanent, relatively large shape such as is obtained when using a rigid-wall tube of equivalent volume-handling capacity.

Test 3) The flexibility for expansion and collapse of the thin-walled tube enables volumes of solution and gas to pass by in countercurrent flow within the tube without suffering from bubble or pocket blockage in the tube such as is experienced with relatively rigid tubing. A 30-cm length of the thin-wall PE tubing, as described in Test 2 above, was used to connect two 450-cucm flexible urine collection bags, one of which was filled with water while the other was left empty, but partially expanded with air. When the bags were raised or lowered relative to one another the water easily flowed from the upper one to the lower.

When the same two bags were connected by 0.64-cm id×0.16-cm wall latex rubber tubing which does not easily flex, and the water transfer test repeated, this.

EXAMPLE 8

Characteristics of Wicking Materials that Enable Continuous and Intermittent Wicking Performance Test 1) In woven or non-woven structures made from fibers such as rayon acetate or cellulose whose surfaces are easily wetted by aqueous solutions, solution is drawn into the narrow capillary spaces between the fibers. When a strip of rayon acetate felt (used in Ex 1, Test 1; 220 g/sq Meter) was wetted by dipping the bottom into 0.9% NaCl solution, as in Ex 1—Test 1, the open voids in the felt structure filled with solution and the top of the solution-filled region rose to a reproducible height above the solution surface and then ceased rising. The maximum wicking height differs for various materials, and among structures of the same materials, differs among structures of different densities. The voids below the liquid "front" remained filled with solution, and the surface of the felt in the wetted region remained "wet" to the touch even when the system was allowed to stand for a long period of time during which the aqueous solution evaporated from the surface of the structure. Evaporation from the felt was evidenced by observing that the liquid level in an identical reservoir that did not have such a felt dipping into it dropped at a much slower rate than did the reservoir with the felt.

Test 2) When a second piece of dry felt was placed in contact with the wet region of a liquid-saturated felt from Test 1 at a point below the top of the liquid front, then solution on the outer surface which contacted the dry felt would wet that dry felt and then be absorbed by or "wicked" into the dry felt. Solution would wick along any pathway that did not exceed the maximum height above the liquid surface for that material; thus solution would travel along the felt wicking conduit along horizontal paths or along downward paths. Furthermore, attaching three 0.5–0 cm wide×wide×5-cm long lengths of dry felting oriented downward by stapling them at 4-cm intervals along the length of a 2-cm wide horizontal wicking conduit resulted in observation that solution traveled down and dripped from each strip showing that an excess of solution was available on each strip.

Test 3) When the supply of aqueous solution was interrupted either by lifting the bottom of the original strip above the surface of the solution in the reservoir or by disrupting the contact between the first and second pieces of felt, then flow through the wetted felt conduit would cease very quickly as judged by the stoppage of dripping from a downward pointing end.

When the supply of aqueous solution was restored, even after interruptions of several hours, then flow through the conduit would resume as observed from the resumption of dripping from downward pointing ends, albeit a brief delay in dripping was seen when the interruption was long enough to require some refilling of the conduit before dripping resumed.

It is thought that the present invention and many of its attendant advantages are understood from the foregoing description. It will be apparent that various changes may be made in the form, construction and arrangement of the parts thereof without departing from the spirit and scope of the invention or sacrificing all of its material advantages, the from hereinbefore described being merely a preferred or exemplary embodiment thereof.

We claim:

1. A system for collecting conveying, and storing urine discharged from a penis of a human male comprising
    means for collection of the urine from the human male comprising proximal and distal ends and outer and inner surfaces;
    means for storage of the urine before disposal of the urine comprising proximal and distal ends and outer and inner surfaces;
    means for conveying the urine from said means for collection of the urine to said means for storage of the urine comprising proximal and distal ends and outer and inner surfaces;
    means for wicking the urine away from the penis wherein said means for wicking moves the urine counter-gravitationally and gravitationally away from the penis through said means for collection and said means for conveying, and deposits the urine in said means for storage, said means for wicking including a first wicking spacer disposed within said means for collection, said means for wicking further including a second wicking spacer disposed within said means for conveying, said means for wicking further including a third wicking spacer disposed within said means for storage of the urine, said means for wicking further including a first wicking spacer piece forming contiguous wicking connection between said first wicking spacer and said second wicking spacer, said means for wicking further including a second wicking spacer piece forming contiguous wicking connections between said second wicking spacer and said third wicking spacer, wherein said first wicking spacer, said first wicking spacer piece, said second wicking spacer, said second wicking spacer piece, and said third wicking spacer collectively form a complete wicking path from said means for collection to said means for storage, said first wicking spacer comprises comprising a y-shape having a tail and two legs such that said legs of said y-shape lie in proximity to said inner surface of said means for collection.

* * * * *